US012697410B2

(12) United States Patent
Jenkins

(10) Patent No.: US 12,697,410 B2
(45) Date of Patent: Aug. 4, 2026

(54) SYSTEM AND METHOD FOR INDOOR AIR PURIFICATION

(71) Applicant: Bancroft Holding Corporation, Elk Grove Village, IL (US)

(72) Inventor: Paul Jenkins, Chicago, IL (US)

(73) Assignee: Geo. Bancroft Engineering, LLC, Mount Prospect, IL (US)

( * ) Notice: Subject to any disclaimer, the term of this patent is extended or adjusted under 35 U.S.C. 154(b) by 71 days.

(21) Appl. No.: 17/366,876

(22) Filed: Jul. 2, 2021

(65) Prior Publication Data

US 2022/0008606 A1     Jan. 13, 2022

Related U.S. Application Data

(60) Provisional application No. 63/048,519, filed on Jul. 6, 2020.

(51) Int. Cl.
A61L 9/20        (2006.01)

(52) U.S. Cl.
CPC ............ A61L 9/20 (2013.01); *A61L 2209/111* (2013.01); *A61L 2209/134* (2013.01)

(58) Field of Classification Search
None
See application file for complete search history.

(56) References Cited

U.S. PATENT DOCUMENTS

| | | |
|---|---|---|
| 5,954,577 A | 9/1999 | Meckler |
| 9,205,218 B1 | 12/2015 | Bachan et al. |

| | | | |
|---|---|---|---|
| 2002/0031460 A1 | 3/2002 | Kulp | |
| 2005/0069465 A1* | 3/2005 | McEllen ................. A61L 9/015 |
| | | | 422/4 |
| 2008/0201119 A1 | 8/2008 | Ahrens | |
| 2019/0240370 A1 | 8/2019 | Benedek et al. | |
| 2022/0243947 A1 | 8/2022 | Dushane | |

FOREIGN PATENT DOCUMENTS

| | | | | | |
|---|---|---|---|---|---|
| CN | 205145205 U | * | 4/2016 | | |
| CN | 205579772 | | 9/2016 | | |
| FR | 2282178 A | * | 4/1976 | | |
| JP | H0741795 B2 | | 5/1995 | | |
| KR | 200323010 Y1 | * | 8/2003 | ............... | A61L 9/20 |
| KR | 20150070004 A | * | 6/2015 | ............... | G01N 1/24 |
| TW | 1687631 B | | 3/2020 | | |
| WO | WO-2005082486 A1 | * | 9/2005 | ............... | A61L 9/20 |

OTHER PUBLICATIONS

International Search Report and Written Opinion, PCT/US2021/040335, Dec. 1, 2021.

* cited by examiner

*Primary Examiner* — Andrew Smyth

(74) *Attorney, Agent, or Firm* — Akerman LLP

(57)        ABSTRACT

A system and method for sanitizing air is disclosed. Atmospheric air is drawn into the system by a fan. The air is passed through a series of baffles to mix the air and reduce speed. The air is exposed to an emitter, such as UV-C light, to sanitize contaminants and then exhausted. The sanitized air drawn into the system and exhausted to the atmosphere without exposing UV-C light to the atmosphere.

20 Claims, 89 Drawing Sheets

505

513

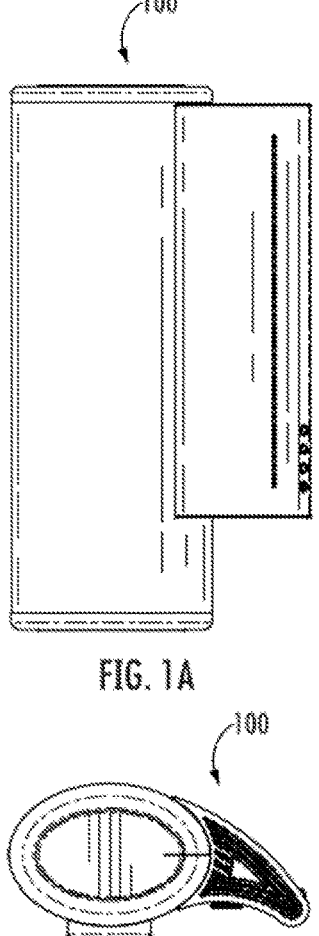
FIG. 1A
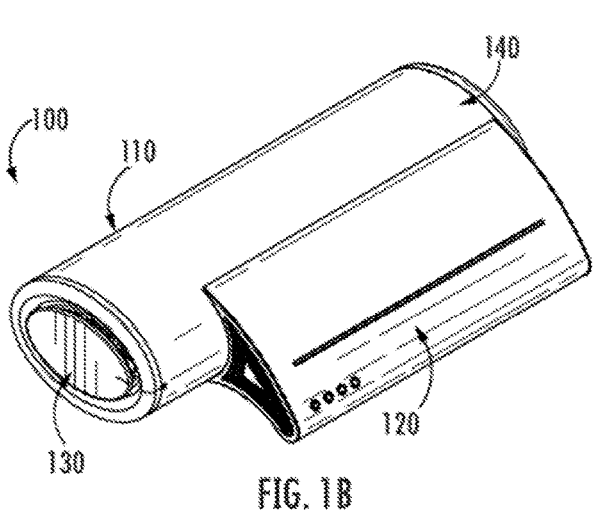
FIG. 1B
FIG. 1C
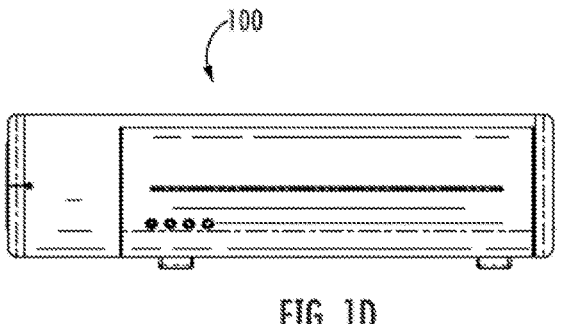
FIG. 1D

150

150

150

150

152

152

152

152

153

160
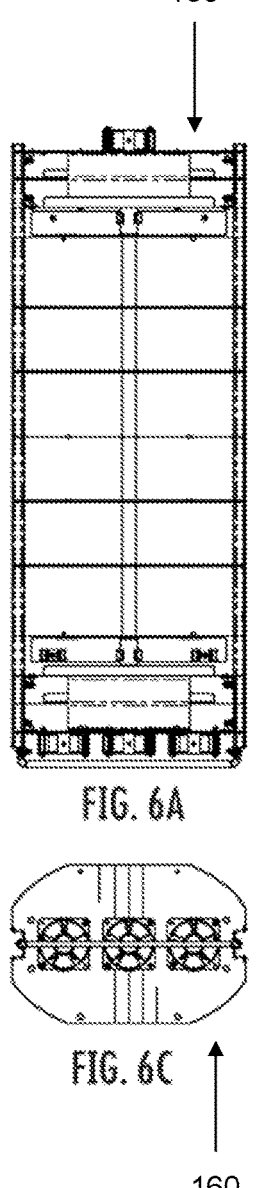
FIG. 6A
FIG. 6C
160
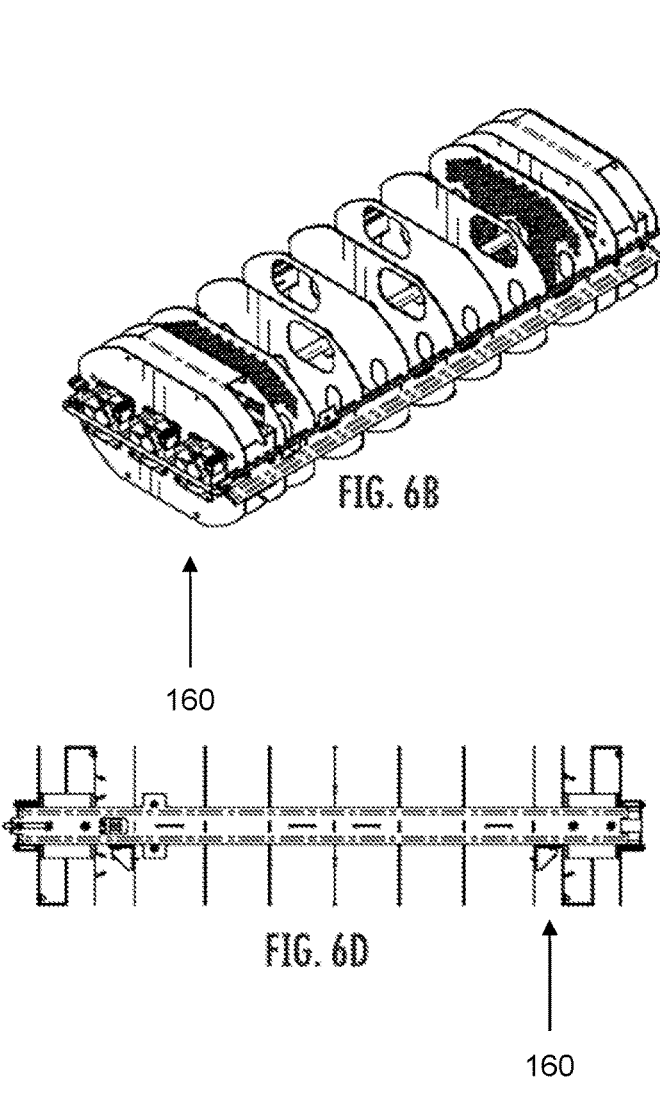
FIG. 6B
160
FIG. 6D
160

168

168

168

168

161

161

161

161

161

161

161

161

161

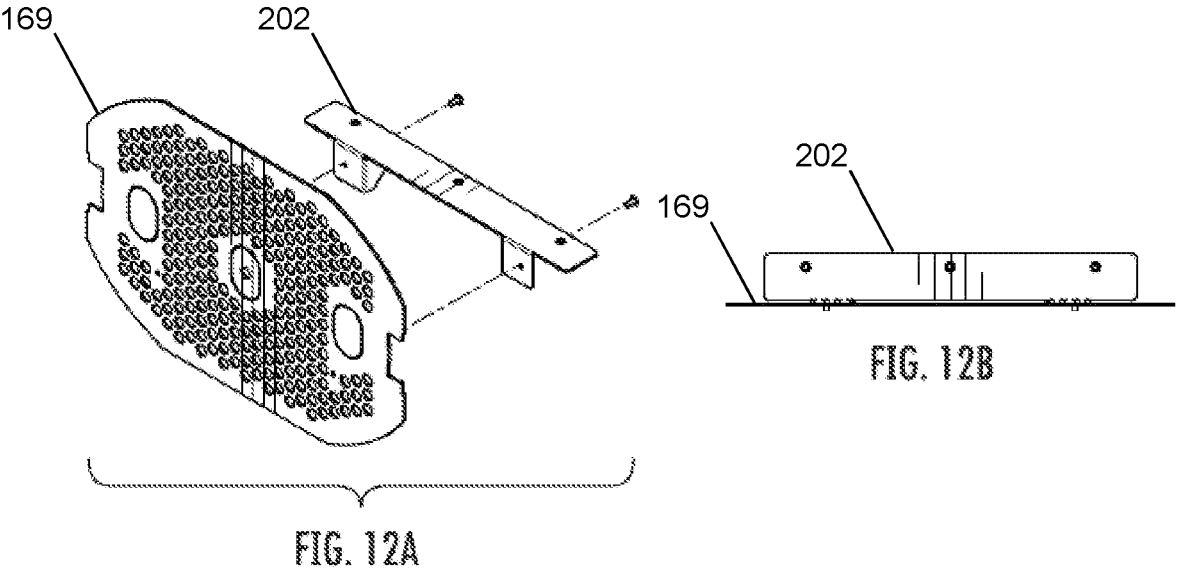
FIG. 12A
FIG. 12B
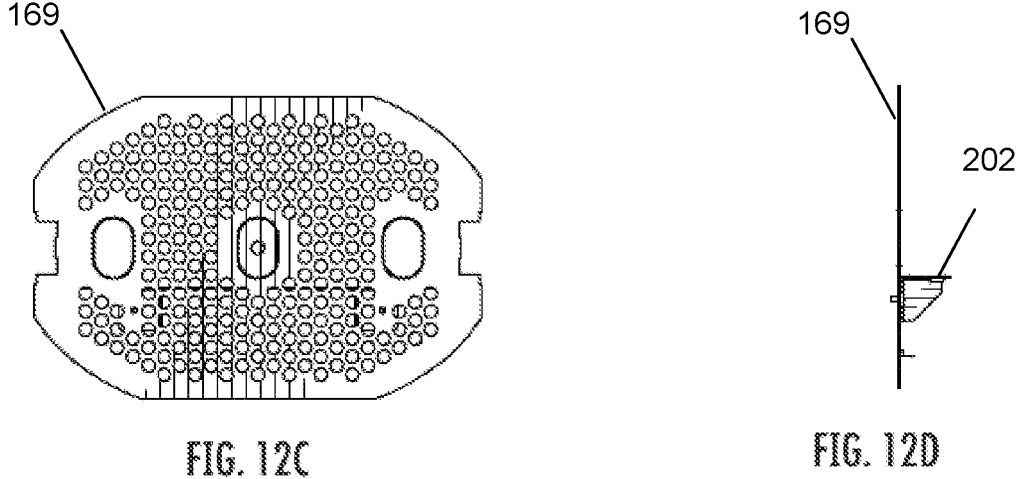
FIG. 12C
FIG. 12D

169

169

169

169

169

202
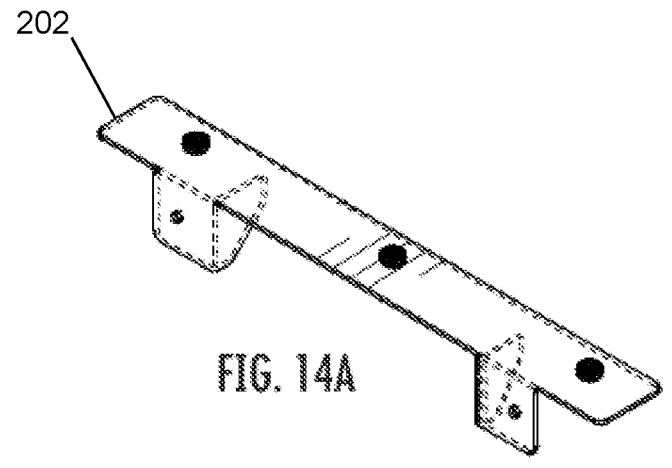
FIG. 14A
202
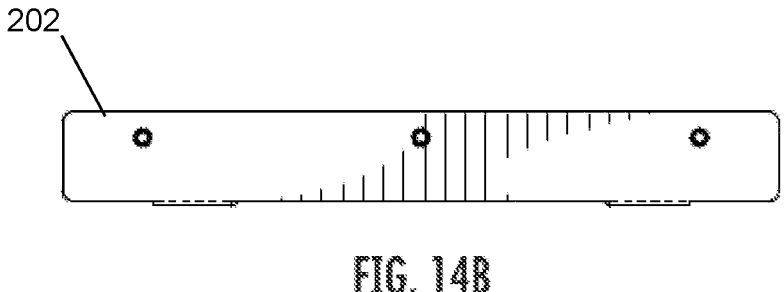
FIG. 14B
202
202
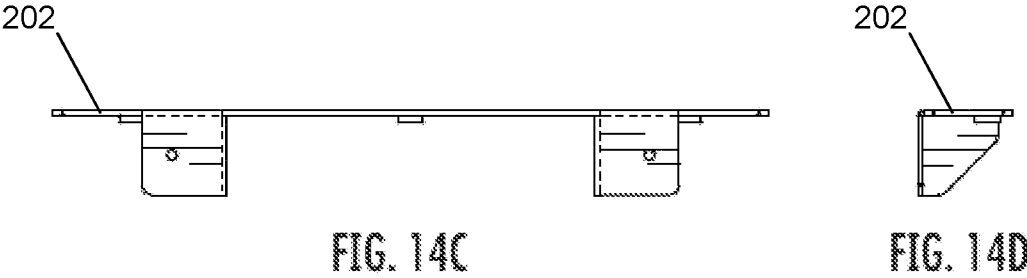
FIG. 14C                    FIG. 14D

202

202

202

202

165

165

165

64          62

165

165

165

66    67

65

61    63

165

61

61

61

61

61

61

61

61

65
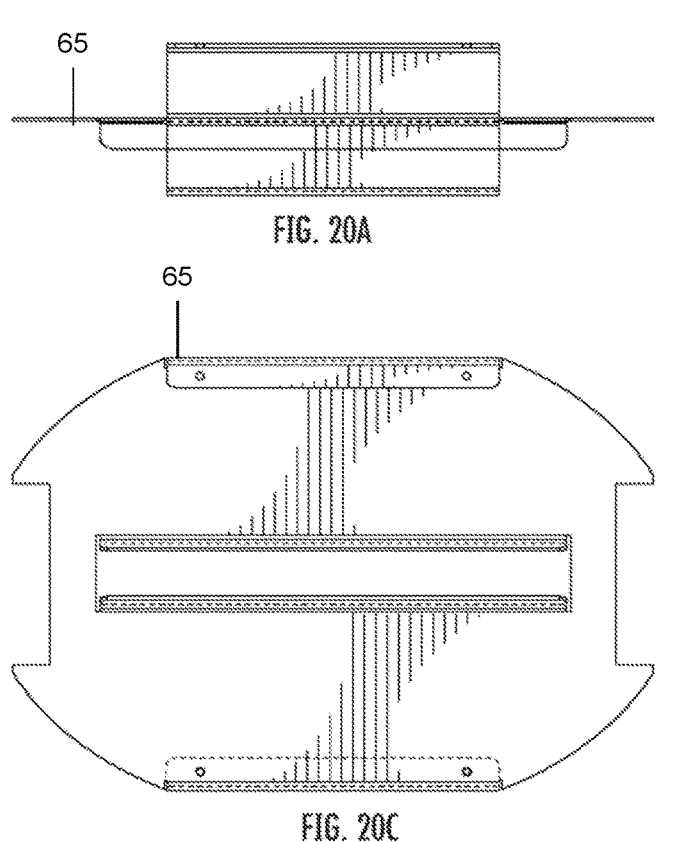
FIG. 20A
FIG. 20C
65
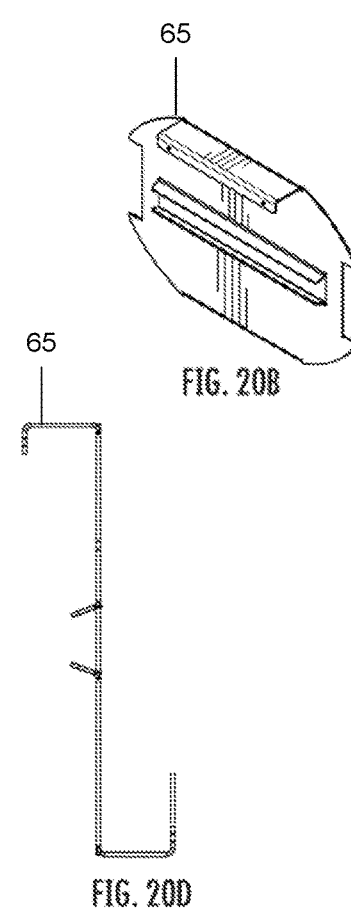
65
FIG. 20B
65
FIG. 20D

66

66

66

66

66

63

63

63

63

63

63

63

63

166

166

76

77

166

75

75

75

75

76

76

76

76

76

73

73

73

73

73
FIG. 29A
73
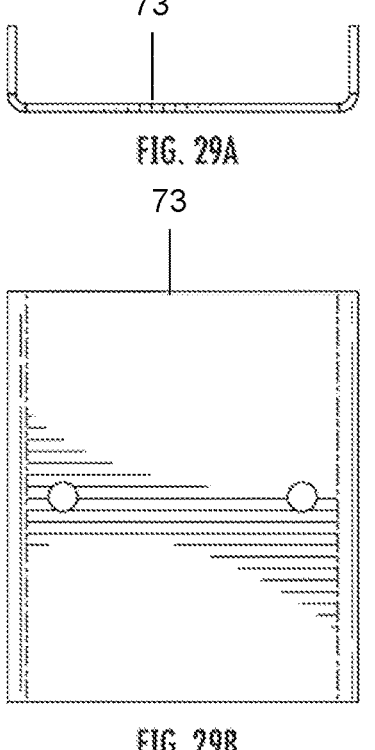
FIG. 29B
73
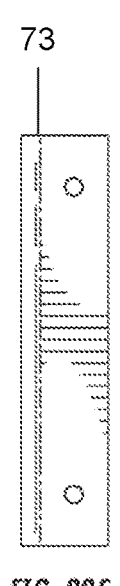
FIG. 29C
73
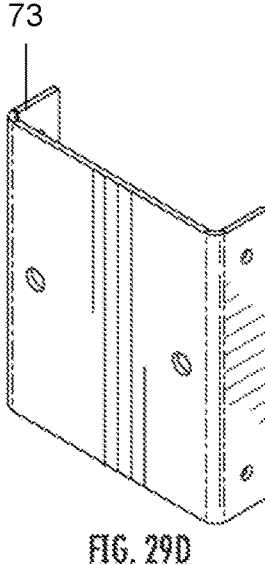
FIG. 29D

167

167

167

167

170

172

174

170

170

172

172

172

172

172

174

174

174

174

174

SECTION B-B

SECTION C-C

SECTION A-A

82
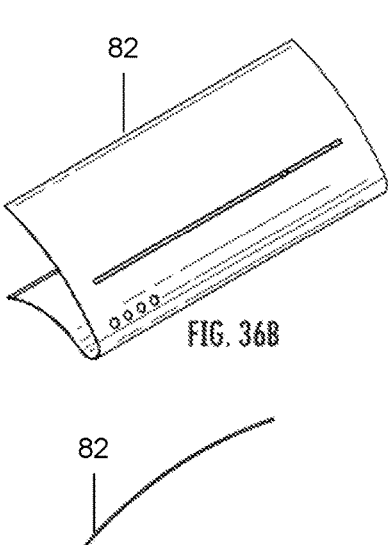
FIG. 36B
82
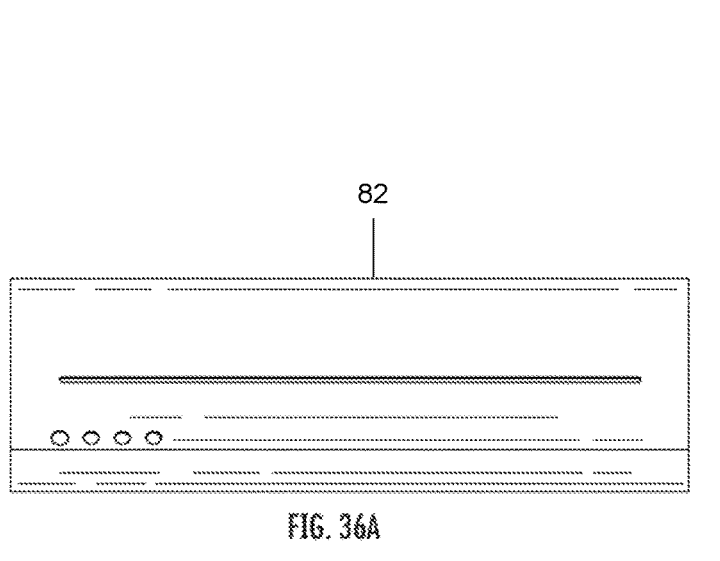
FIG. 36A
82
FIG. 36C

82

82

82

181

181

181

181

182

182

182

182

83

83

83

83

SECTION A-A

84

84

84

84

84

91

91

91

91

91

91

91

91

SECTION A-A

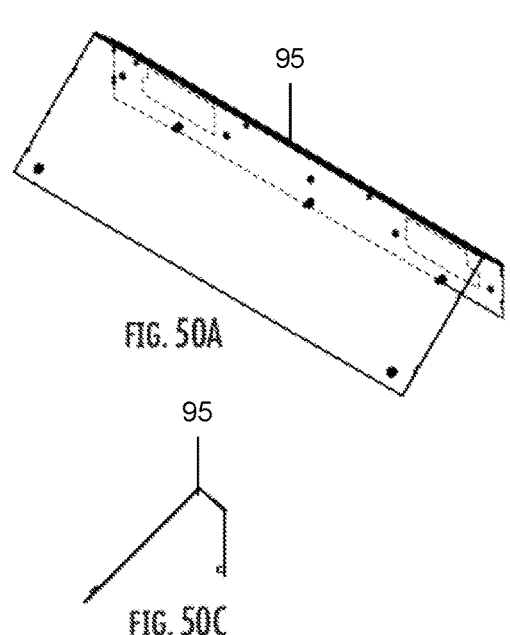
FIG. 50A
FIG. 50B
FIG. 50C
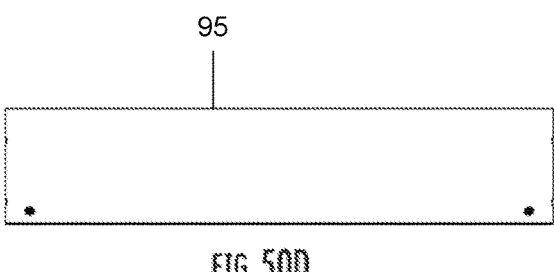
FIG. 50D

95

SECTION A-A

95

95

95

A

A

95

96

96

VIEW A-A

96

96

96

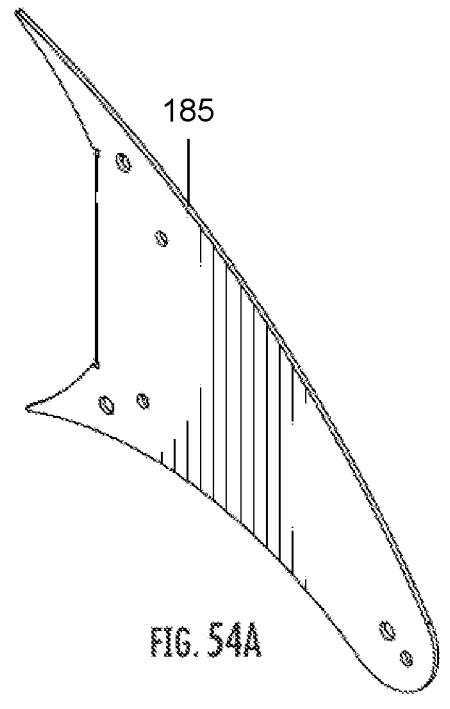
185
FIG. 54A
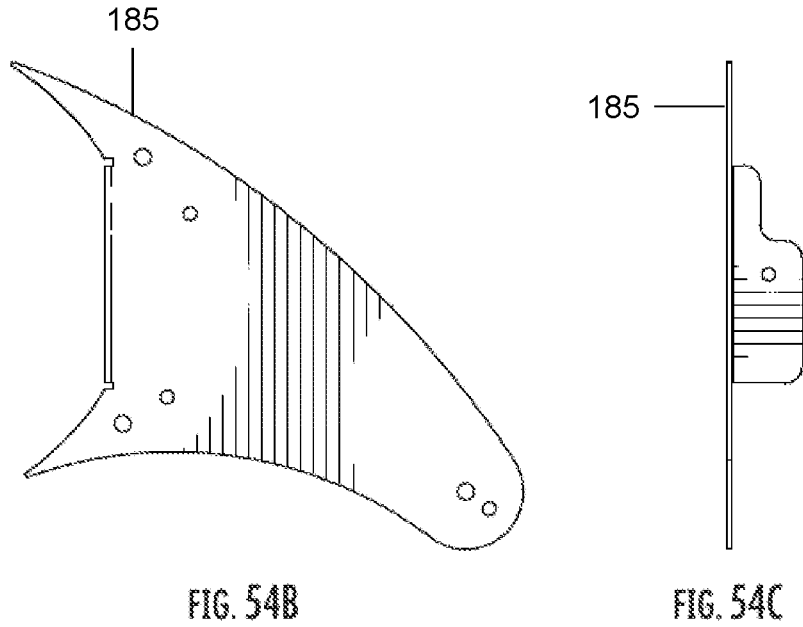
185
FIG. 54B
185
FIG. 54C

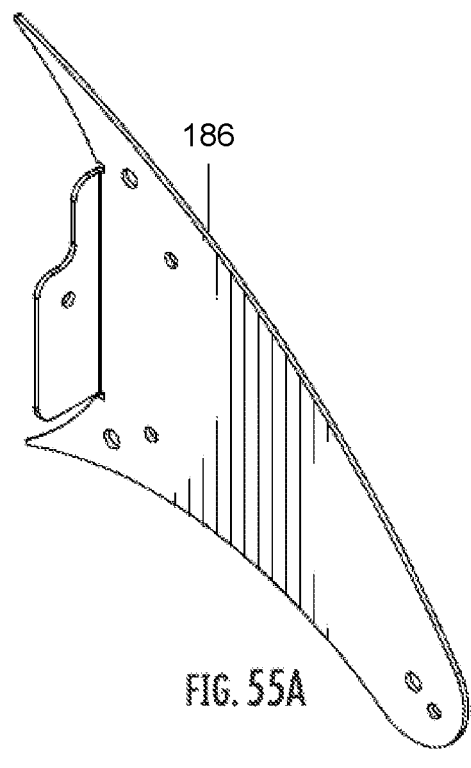
186
FIG. 55A
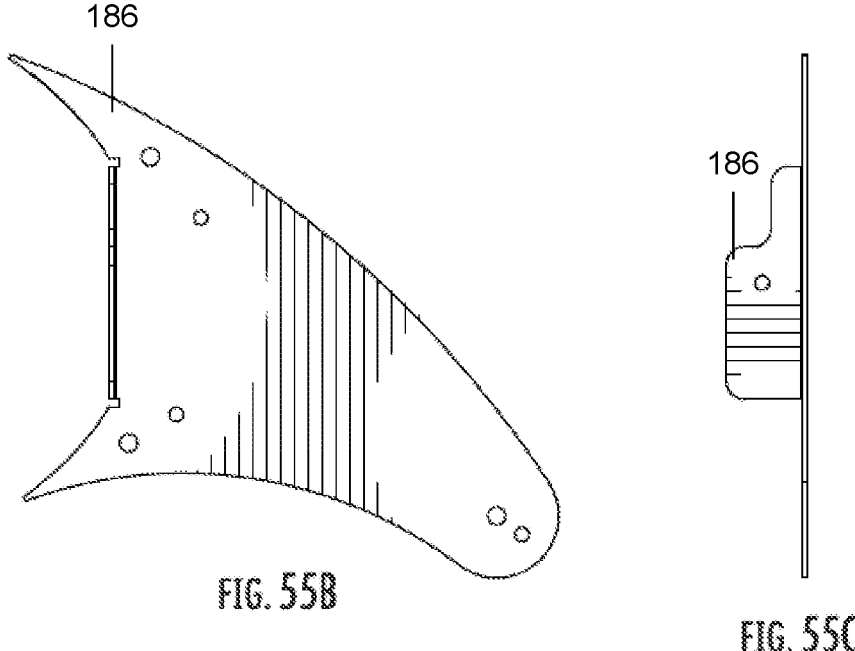
186
FIG. 55B
186
FIG. 55C

504

511

504

515

504

504

SECTION C-C

506

517

506

506

513

513

513

513

505

505

505

513

505

505

506

506

517

506

507

507

507

507

507

SECTION B-B

504

504

504

504

506

506

506

506

512

512

512

517

517

517

518

518

518

518

518

513

513

513

513

519

519

519

519

512

512

512

520

520

520

520

521

521

522

522

522

522

523

523

523

524

524

524

524

524

525

525

525

525

526

526

526

526

526

527

527

527

528

528

528

529

529

529

529

531

531

531

531

531

532

532

532

533

533

533

534
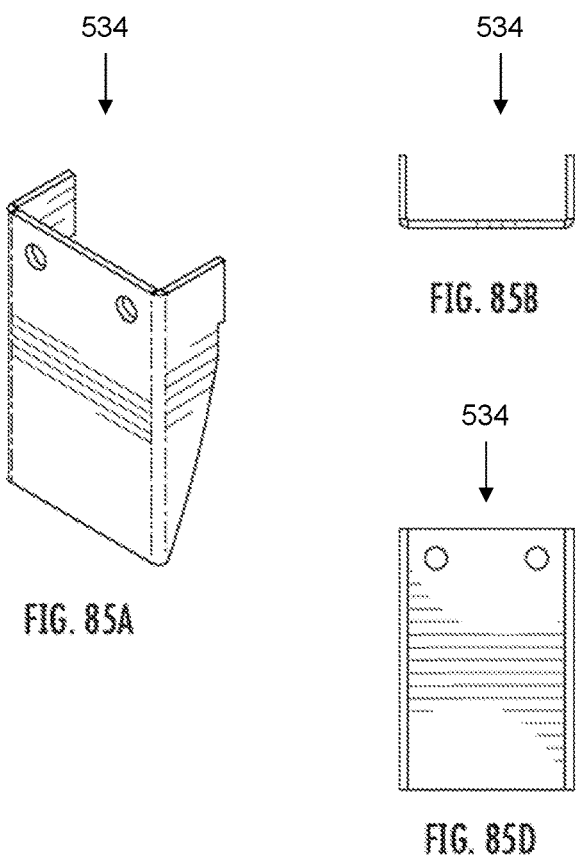
FIG. 85A
534
FIG. 85B
534
FIG. 85D
534
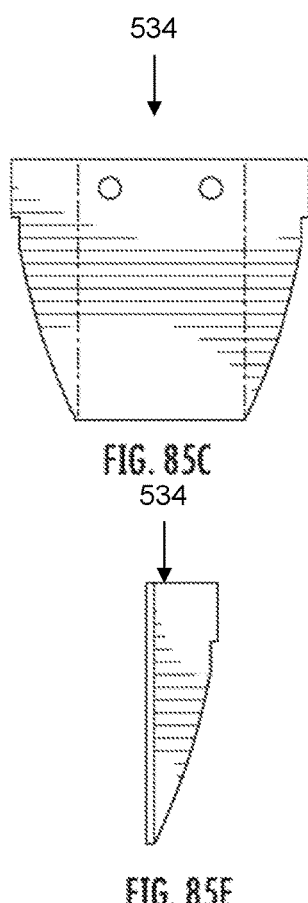
FIG. 85C
534
FIG. 85E

8800

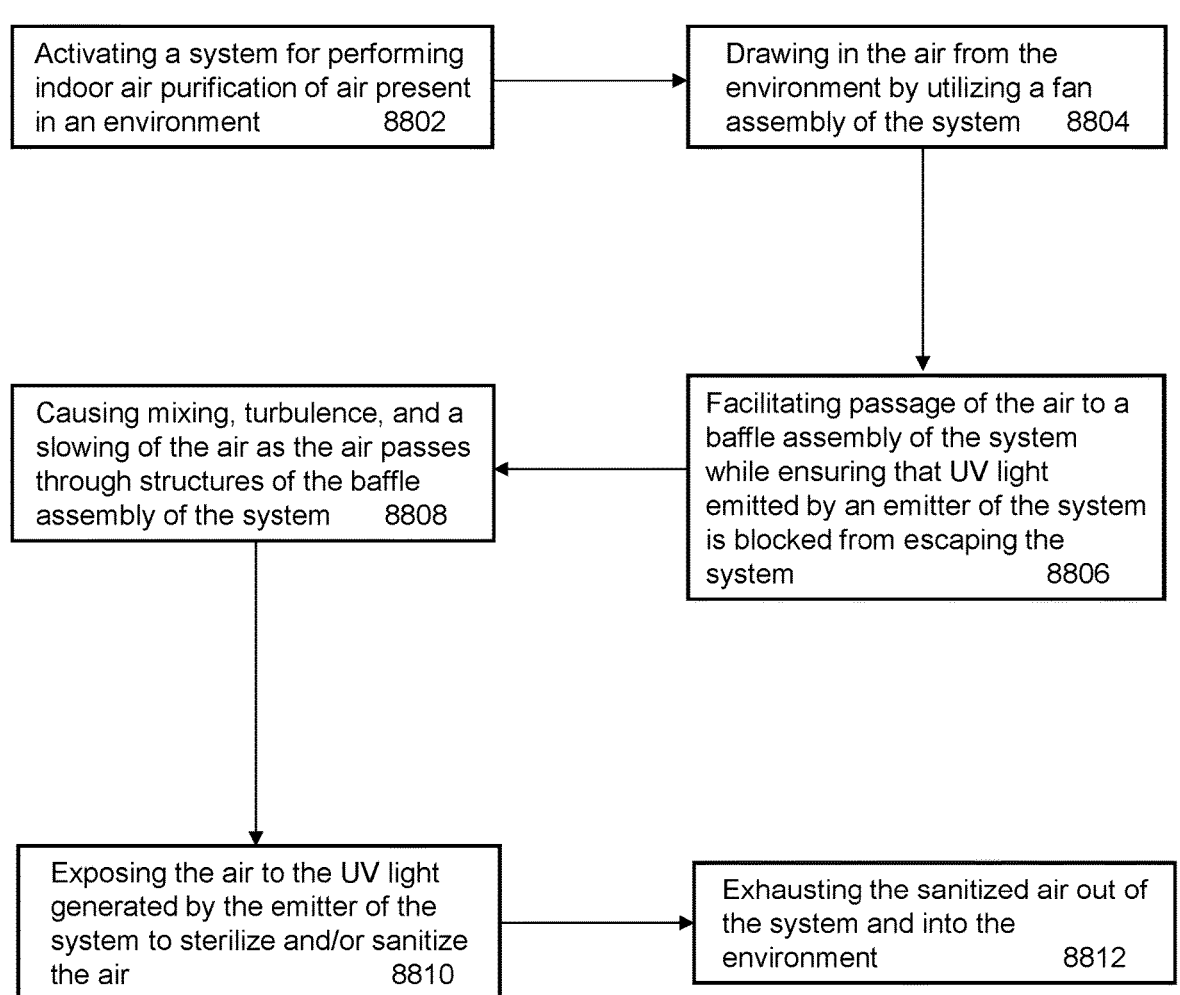

| | |
|---|---|
| Activating a system for performing indoor air purification of air present in an environment        8802 | Drawing in the air from the environment by utilizing a fan assembly of the system      8804 |
| Causing mixing, turbulence, and a slowing of the air as the air passes through structures of the baffle assembly of the system        8808 | Facilitating passage of the air to a baffle assembly of the system while ensuring that UV light emitted by an emitter of the system is blocked from escaping the system                8806 |
| Exposing the air to the UV light generated by the emitter of the system to sterilize and/or sanitize the air        8810 | Exhausting the sanitized air out of the system and into the environment              8812 |

FIG. 88

SYSTEM AND METHOD FOR INDOOR AIR PURIFICATION

CROSS-REFERENCE TO RELATED APPLICATIONS

This application claims priority to and the benefit of U.S. Provisional Application No. 63/048,519, filed on Jul. 6, 2020, the disclosure of which is hereby incorporated by reference in its entirety.

FIELD OF THE INVENTION

The present invention relates to a system and method for purifying air, and in particular a system and method for eradicating viral, fungal and bacterial bioburden using baffling and an emitter to purify the air via ultraviolet (UV) light exposure.

BACKGROUND

Human exposure to viruses, fungi, bacteria, pathogens, and microorganisms often create a risk of negative health effects. Such contaminants may be present in substantial and often surprising quantities in the air and on the objects existing in an environment. Additionally, recent worldwide events related to Covid-19 demonstrate that there is great concern worldwide about virus contraction and transmission through the air and about the importance of air quality. As a result, having effective technologies and processes for reducing or eliminating such contaminants from an environment has become increasingly important in today's society.

To that end, various systems and methods for treating and/or sanitizing indoor air have been implemented to reduce the transmission of viruses, bacteria, and other pathogens. For example, these systems and methods include standalone units as well as devices designed for integration with central air handling systems, such as heating, ventilation and air conditioning (HVAC). Other systems and methods involve utilizing various types of aerosol-based disinfectants, air purifiers, chemical and/or physical disinfectant devices, sterilizers, and other similar devices. Notably, however, such systems, devices and methods have many shortcomings including, but not limited to, inefficiencies, difficulty of use, ineffectiveness, long sterilization and/or sanitization times, high expense, limited sanitization capabilities, among other shortcomings. For example, various types of filters have been used to remove particulate matter and air pollutants from indoor air. However, filters may lose effectiveness between replacement intervals and as particulate matter and air pollutants become trapped within the filters. Radiation sources such as ultraviolet lamps have been used, however, effectiveness may be limited based on radiation exposure and airflow conditions. As a result, there is a need for improved technologies and processes to treat and purify indoor air. Based on the foregoing, current air purification technologies and processes may be improved and enhanced to provide for more effective pathogen sterilization, longer-lasting sterilization capabilities, reduced costs, and increased customer satisfaction.

SUMMARY

The present invention relates to a system and method for sanitizing air, and, in particular, a system and method for eradicating viral, fungal and bacterial bioburden using baffling and an emitter, for example, through the use of UV light exposure. In one embodiment, a system for sanitizing air is disclosed. The system may include a main body and a control housing assembly. The main body may include a baffle assembly. The baffle assembly may include a front fan assembly, a rear fan assembly, at least one inner baffle plate, at least one end baffle plate, and at least one emitter, for example a UV-C light source. The front fan assembly and rear fan assembly may include a mid-baffle and internal baffle to block the UV-C light source. Air may be drawn into the system through the front fan assembly. As air passes through the end baffle plate and inner baffle plate, air speed may be reduced and turbulence may be increased, thereby increasing the efficacy for the UV-C light to sanitize the air. Viruses, bacteria, microorganisms, fungi, and/or pathogens present in the air may be killed or at least prevented from replicating based on their exposure to the UV-C light. For example, when such organisms are exposed to UV-C light generated by the system, cells of the organisms may rupture in response to absorbing the UV-C light. In certain instances, the UV-C light may be absorbed by DNA or RNA of the organisms, which may cause the formation of dimers that disrupt the replication of the organisms' cells. Once the air is sanitized by the system, the sanitized air may be exhausted from the rear fan assembly and out into the environment.

In another embodiment, a system for sanitizing air is disclosed. The system may include a housing. In certain embodiments, the housing may include a front fan, a plurality of dividers, an air baffle assembly, an end cap assembly, and at least one emitter, such as a UV-C light source. The dividers and end cap assembly include structure to allow air flow through the system, while blocking the UV-C light source. Air may be drawn into the system through the front fan. As air passes through the baffle assembly, the air may be mixed and turbulence may be generated, thereby increasing the efficacy for the UV-C light to sanitize the air. Sanitized air may then be exhausted from the end cap assembly and into the surrounding environment.

In another embodiment, a method for sanitizing air by utilizing a system is disclosed. The method may include a first step of having the system take in air from the atmosphere or an environment. Additionally, the method may include a second step of mixing the air by passing the air through baffles of the system. Furthermore, the method may include a third step of exposing the mixed air to an emitter, for example a UV-C light to sanitize the air. Moreover, the method may include a fourth step of exhausting the sanitized air to the atmosphere or the environment.

These and other features of the systems and methods for sanitizing air are described in the following detailed description, drawings, and appended claims.

BRIEF DESCRIPTION OF THE DRAWINGS

FIG. 1A illustrates a top view of a system 100.

FIG. 1B illustrates an angled perspective view of the system 100.

FIG. 1C illustrates an end view of the system 100.

FIG. 1D illustrates a side view of the system 100.

FIG. 6A illustrates a top view of a baffle assembly 160 of the system 100.

FIG. 6B illustrates an angled perspective view of the baffle assembly 160 of the system 100.

FIG. 6C illustrates an end view of the baffle assembly 160 of the system 100.

FIG. 6D illustrates a front view of the baffle assembly 160 of the system 100.

FIG. 12A illustrates an angled perspective view of an end baffle plate 169 of the system 100.

FIG. 12B illustrates a top view of an end baffle plate 169 of the system 100.

FIG. 12C illustrates a front view of an end baffle plate 169 of the system 100.

FIG. 12D illustrates a side view of an end baffle plate 169 of the system 100.

FIG. 14A illustrates an angled perspective view of a bulb mount bracketing for lighting tubes to be held within the baffle assembly 160 of the system 100.

FIG. 14B illustrates a top view of a bulb mount bracketing for lighting tubes to be held within the baffle assembly 160 of the system 100.

FIG. 14C illustrates a front view of a bulb mount bracketing for lighting tubes to be held within the baffle assembly 160 of the system 100.

FIG. 14D illustrates a side view of a bulb mount bracketing for lighting tubes to be held within the baffle assembly 160 of the system 100.

FIG. 20A illustrates a top view of the front fan mid-baffle 65 of the system 100.

FIG. 20B illustrates an angled perspective view of the front fan mid-baffle 65 of the system 100.

FIG. 20C illustrates a front view of the front fan mid-baffle 65 of the system 100.

FIG. 20D illustrates a side view of the front fan mid-baffle 65 of the system 100.

FIG. 29A illustrates a top view of the rear fan bracket 73 of the system 100.

FIG. 29B illustrates a front view of the rear fan bracket 73 of the system 100.

FIG. 29C illustrates a side view of the rear fan bracket 73 of the system 100.

FIG. 29D illustrates an angled perspective view of the rear fan bracket 73 of the system 100.

FIG. 30D illustrates a side view of the handle 167 of the system 100.

FIG. 31A illustrates a front view of the main side cap 170 of the system 100.

FIG. 31B illustrates an angled perspective view of the main side cap 170 of the system 100.

FIG. 31C illustrates a side view of the main side cap 170 of the system 100.

FIG. 31D illustrates a front view of the main side cap 170 of the system 100.

FIG. 32A illustrates the main side cap 170 of the system 100.

FIG. 32B illustrates the main side cap 170 of the system 100.

FIG. 32C illustrates the main side cap 170 of the system 100.

FIG. 32D illustrates the main side cap 170 of the system 100.

FIG. 32E illustrates the main side cap 170 of the system 100.

FIG. 33A illustrates the main side cap 170 of the system 100.

FIG. 33B illustrates the main side cap 170 of the system 100.

Figures 33A, 33B, 33C, 33D, 33E:
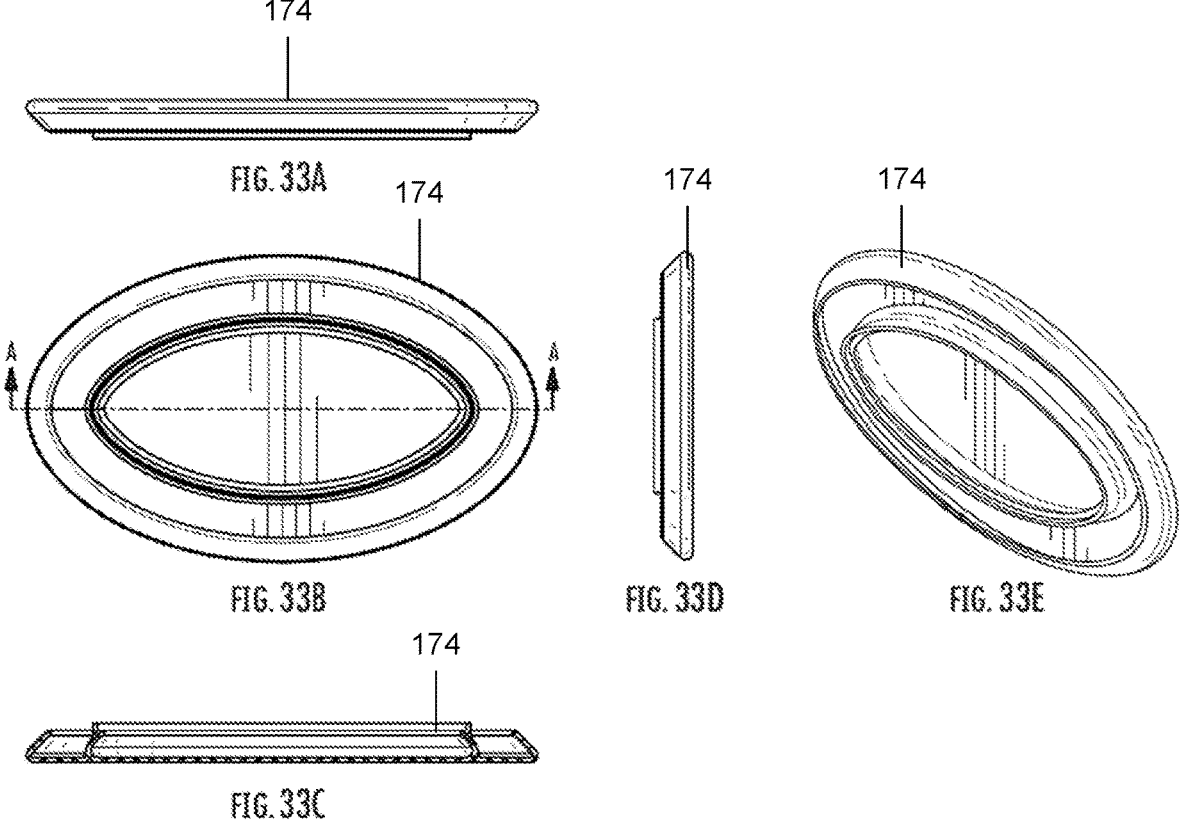

FIG. 33C illustrates the main side cap 170 of the system 100.

FIG. 33D illustrates the main side cap 170 of the system 100.

FIG. 33E illustrates the main side cap 170 of the system 100.

Figures 34A, 34B, 34C:
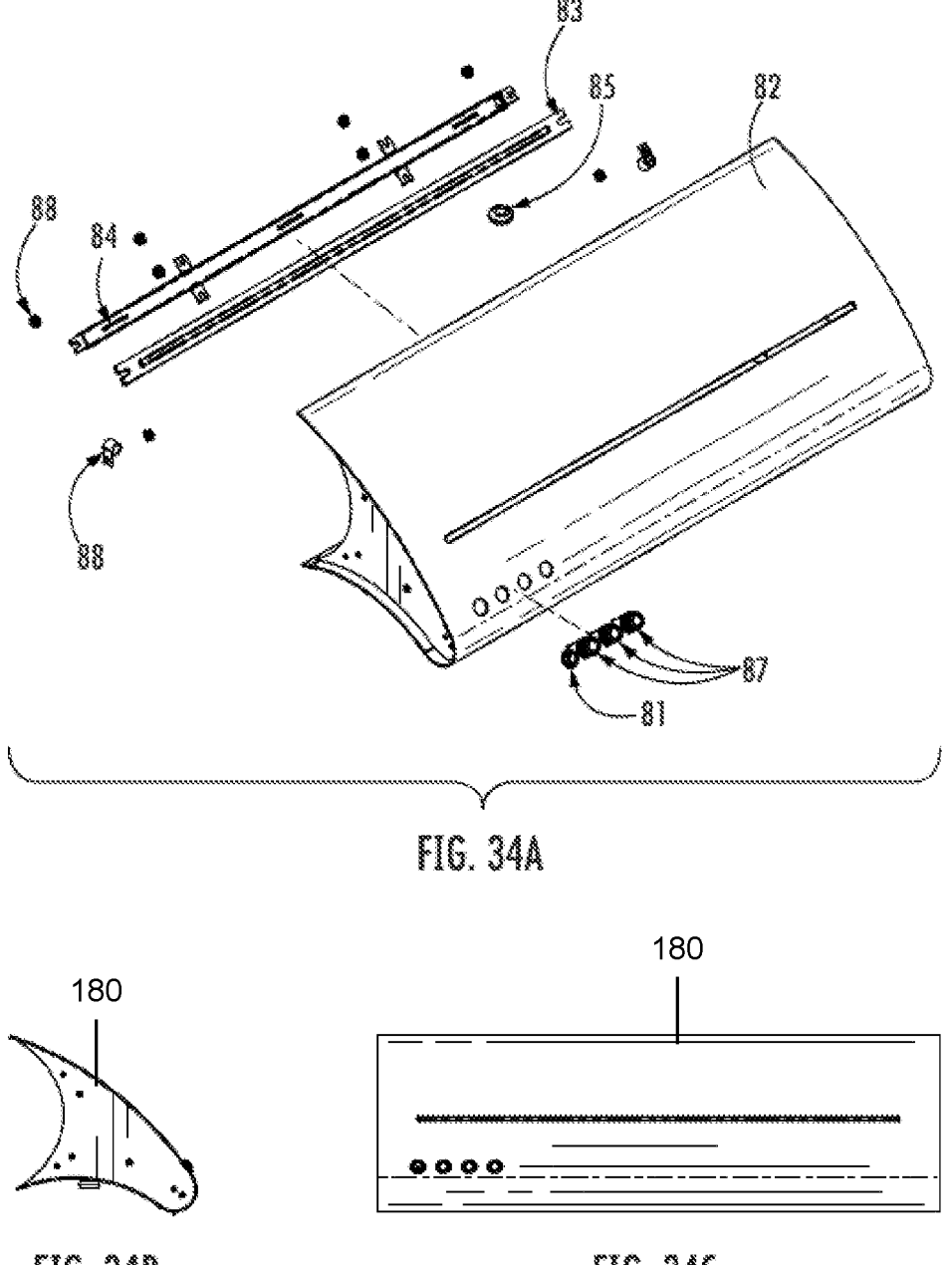

FIG. 34A illustrates the control housing assembly 180 of the system 100.

FIG. 34B illustrates the control housing assembly 180 of the system 100.

FIG. 34C illustrates the control housing assembly 180 of the system 100.

Figures 35A, 35B, 35C, 35D, 35E, 35F, 35G:
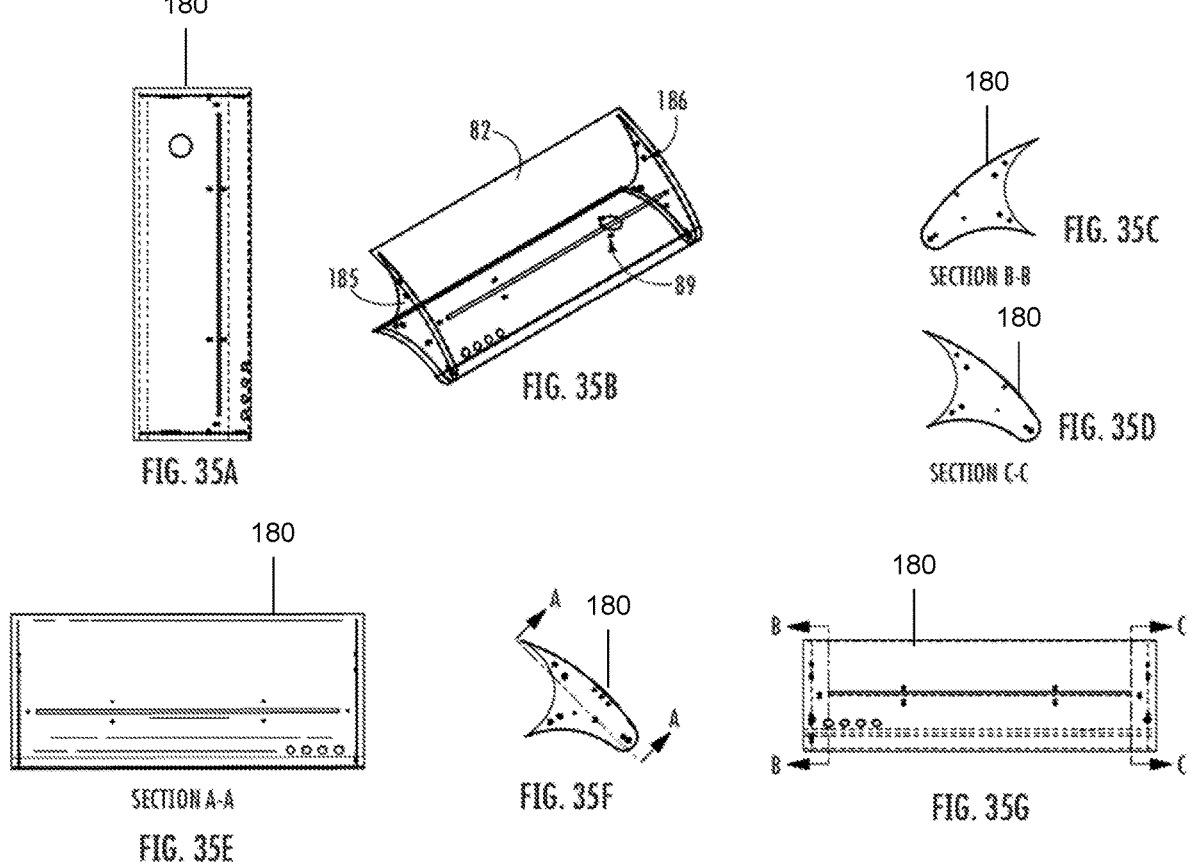

FIG. 35A illustrates the control housing assembly 180 of the system 100.

FIG. 35B illustrates the control housing assembly 180 of the system 100.

FIG. 35C illustrates components of the control housing assembly 180 of the system 100.

FIG. 35D illustrates components of the control housing assembly 180 of the system 100.

FIG. 35E illustrates the control housing assembly 180 of the system 100.

FIG. 35F illustrates components of the control housing assembly 180 of the system 100.

FIG. 35G illustrates the control housing assembly 180 of the system 100.

FIG. 36A illustrates components of the control housing assembly 180 of the system 100.

FIG. 36B illustrates components of the control housing assembly 180 of the system 100.

FIG. 36C illustrates components of the control housing assembly 180 of the system 100.

Figure 37A:
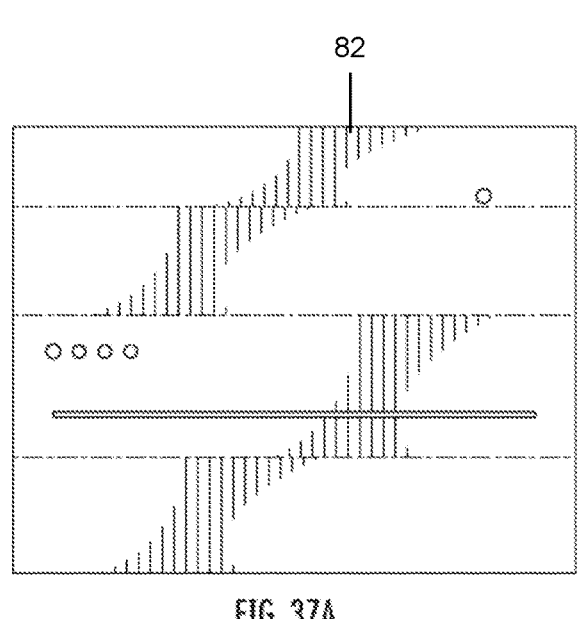

FIG. 37A illustrates the control housing assembly 180 of the system 100.

Figure 37B:
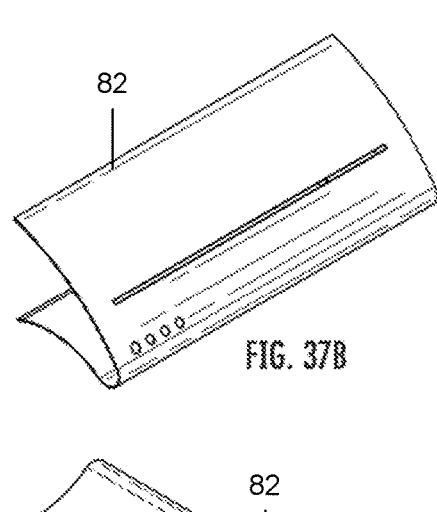

FIG. 37B illustrates the control housing assembly 180 of the system 100.

Figure 37C:
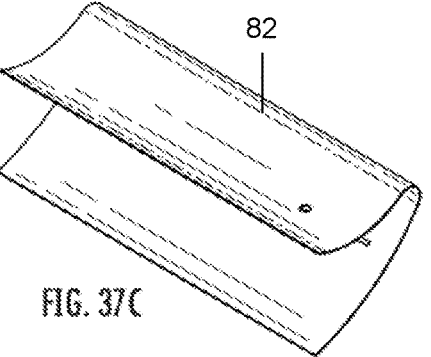

FIG. 37C illustrates the control housing assembly 180 of the system 100.

Figure 38A:
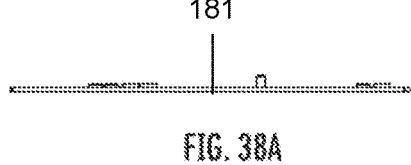

FIG. 38A illustrates the first control side cap 181 of the system 100.

Figure 38B:
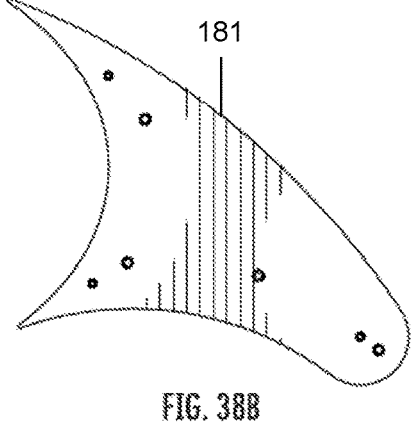

FIG. 38B illustrates the first control side cap 181 of the system 100.

Figure 38C:
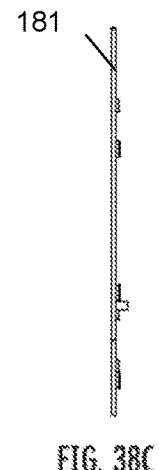

FIG. 38C illustrates the first control side cap 181 of the system 100.

Figure 38D:
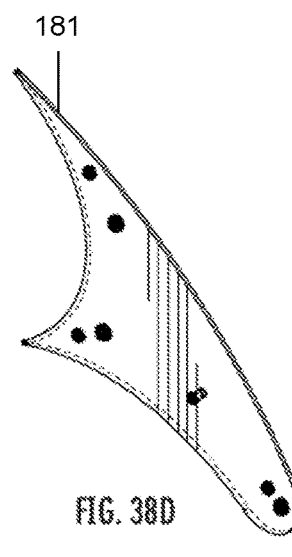

FIG. 38D illustrates the first control side cap 181 of the system 100.

Figures 39A, 39B, 39C:
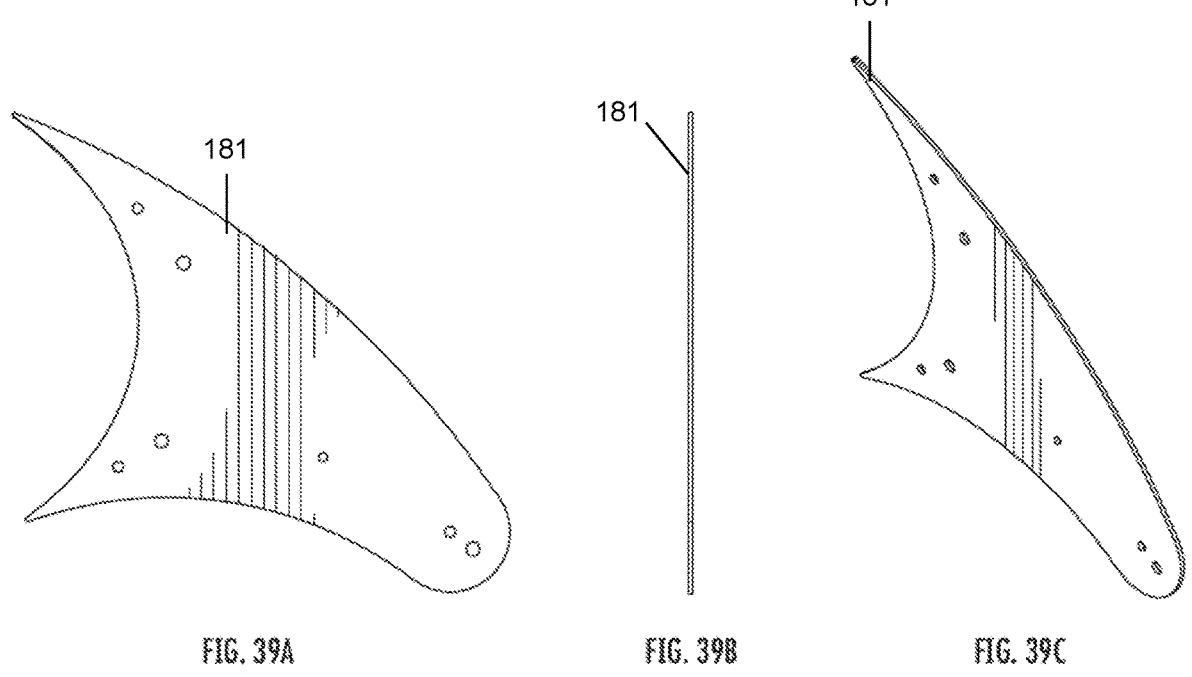

FIG. 39A illustrates the first control side cap 181 of the system 100.

FIG. 39B illustrates the first control side cap 181 of the system 100.

FIG. 39C illustrates the first control side cap 181 of the system 100.

Figure 40A:
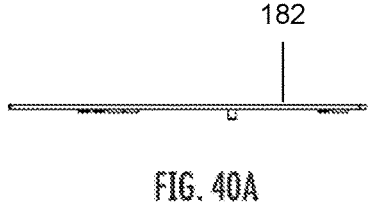

FIG. 40A illustrates the second control side cap 182 of the system 100.

Figure 40B:
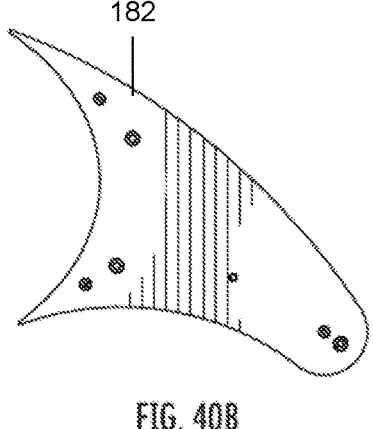

FIG. 40B illustrates the second control side cap 182 of the system 100.

Figure 40C:
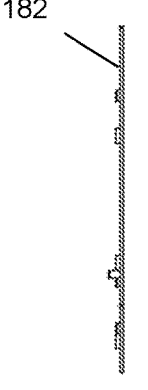

FIG. 40C illustrates the second control side cap 182 of the system 100.

Figure 40D:
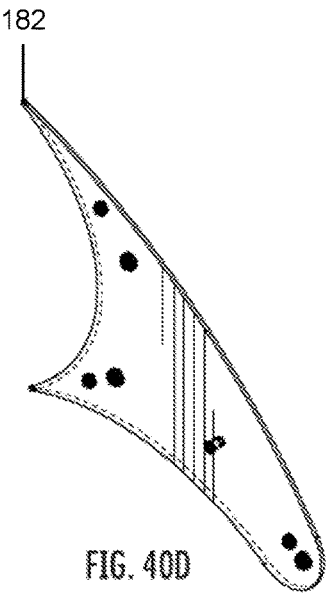

FIG. 40D illustrates the second control side cap 182 of the system 100.

Figures 41A, 41B, 41C:
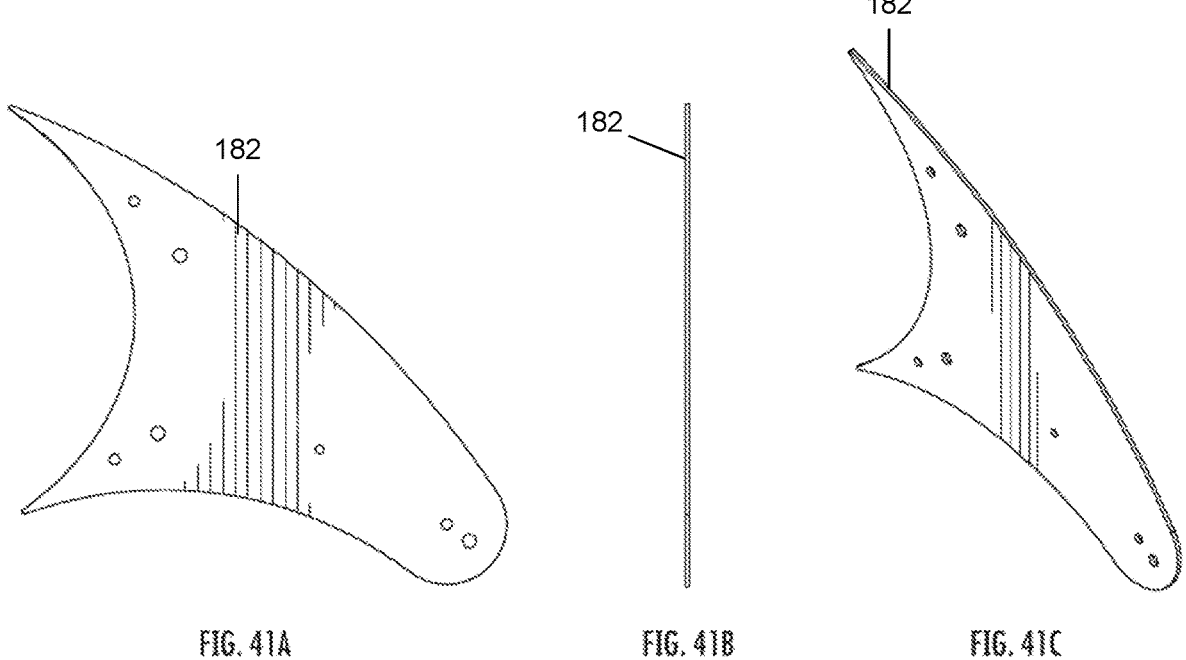

FIG. 41A illustrates the second control side cap 182 of the system 100.

FIG. 41B illustrates the second control side cap 182 of the system 100.

FIG. 41C illustrates the second control side cap 182 of the system 100.

Figures 42A, 42B, 42C, 42D:
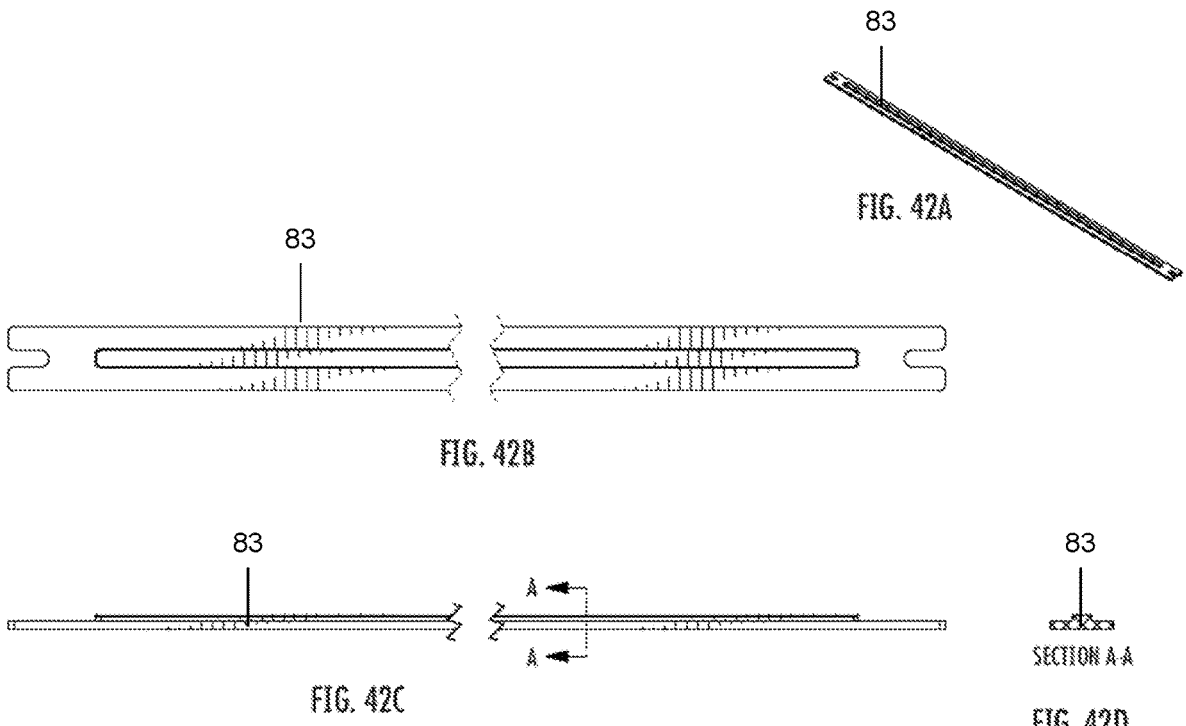

FIG. 42A illustrates the led lens 83 of the system 100.

FIG. 42B illustrates the led lens 83 of the system 100.

FIG. 42C illustrates the led lens 83 of the system 100.

FIG. 42D illustrates the led lens 83 of the system 100.

Figures 43A, 43B, 43C, 43D, 43E:
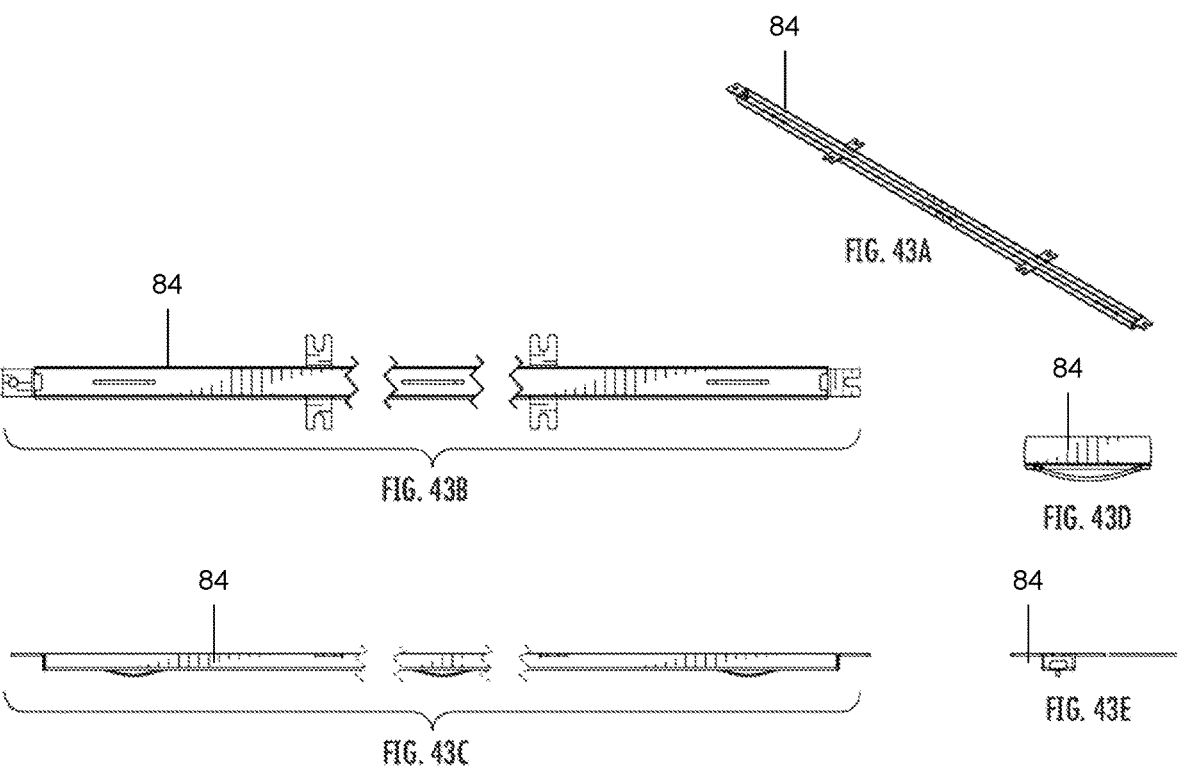

FIG. 43A illustrates the led housing 84 of the system 100.

FIG. 43B illustrates the led housing 84 of the system 100.

FIG. 43C illustrates the led housing 84 of the system 100.

FIG. 43D illustrates the led housing 84 of the system 100.

FIG. 43E illustrates the led housing 84 of the system 100.

Figures 44A, 44B, 44C:
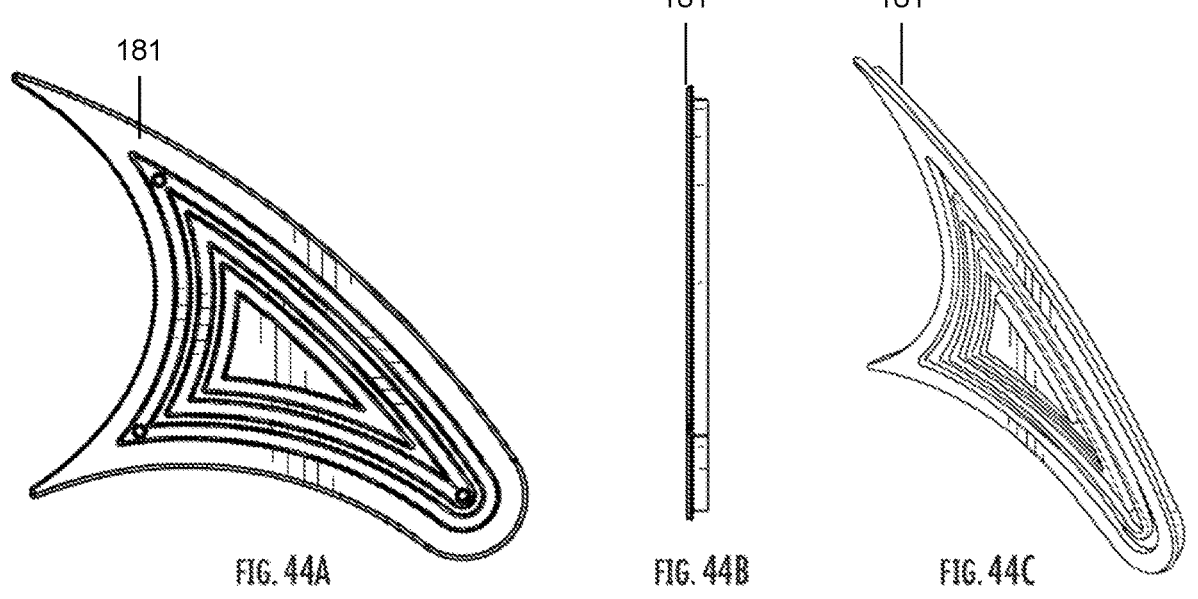

FIG. 44A illustrates the first control side cap 181 of the system 100.

FIG. 44B illustrates the first control side cap 181 of the system 100.

FIG. 44C illustrates the first control side cap 181 of the system 100.

Figures 45A, 45B, 45C:
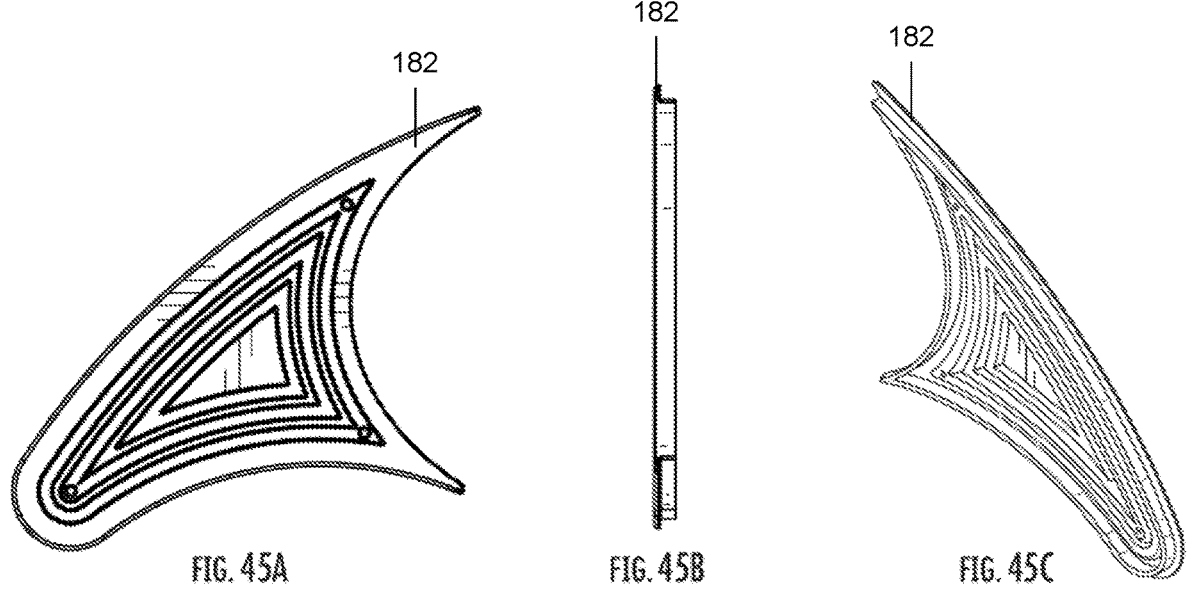

FIG. 45A illustrates the second control side cap 182 of the system 100.

FIG. 45B illustrates the second control side cap 182 of the system 100.

FIG. 45C illustrates the second control side cap 182 of the system 100.

Figures 46A, 46B, 46C, 46D:
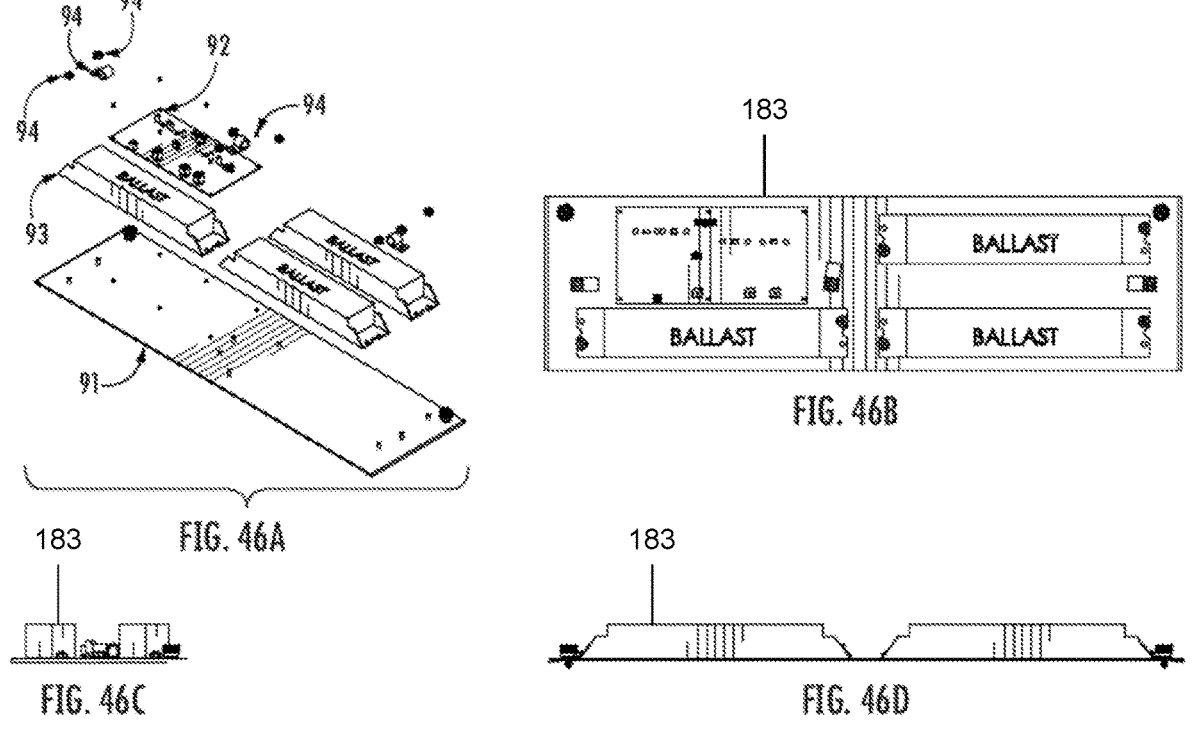

FIG. 46A illustrates the electronics panel assembly 183 of the system 100.

FIG. 46B illustrates the electronics panel assembly 183 of the system 100.

FIG. 46C illustrates the electronics panel assembly 183 of the system 100.

FIG. 46D illustrates the electronics panel assembly 183 of the system 100.

Figure 47A:
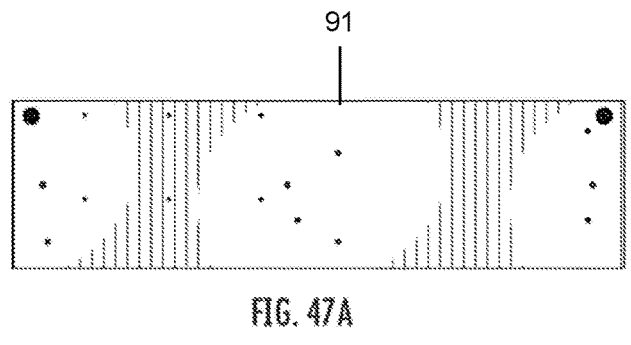

FIG. 47A illustrates sub panel 91 of the system 100.

Figure 47B:
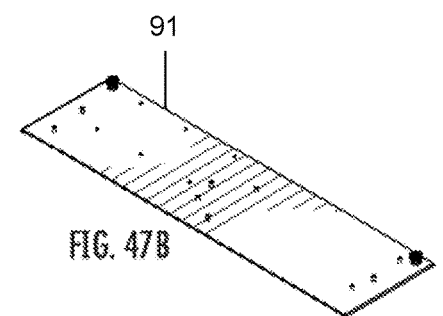

FIG. 47B illustrates sub panel 91 of the system 100.

Figure 47C:
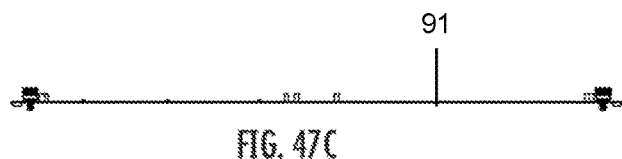

FIG. 47C illustrates sub panel 91 of the system 100.

Figure 47D:
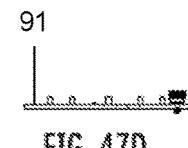

FIG. 47D illustrates sub panel 91 of the system 100.

Figures 48A, 48B, 48C, 48D:
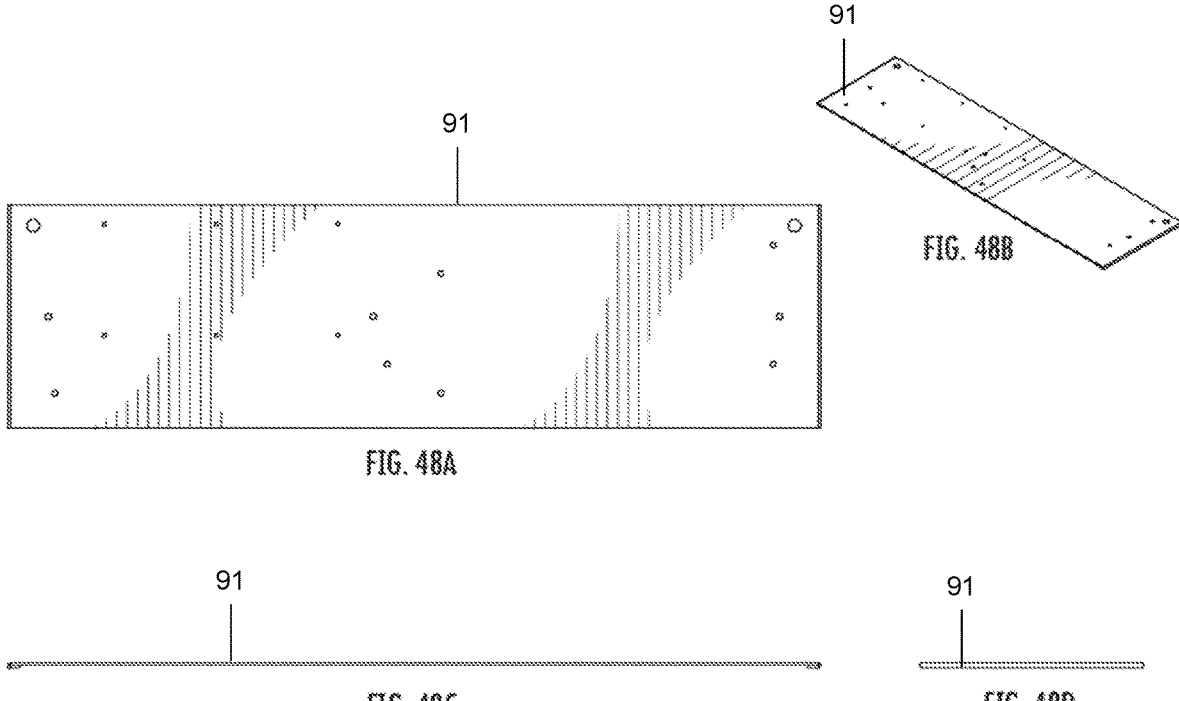

FIG. 48A illustrates sub panel 91 of the system 100.

FIG. 48B illustrates sub panel 91 of the system 100.

FIG. 48C illustrates sub panel 91 of the system 100.

FIG. 48D illustrates sub panel 91 of the system 100.

Figures 49A, 49B, 49C, 49D:
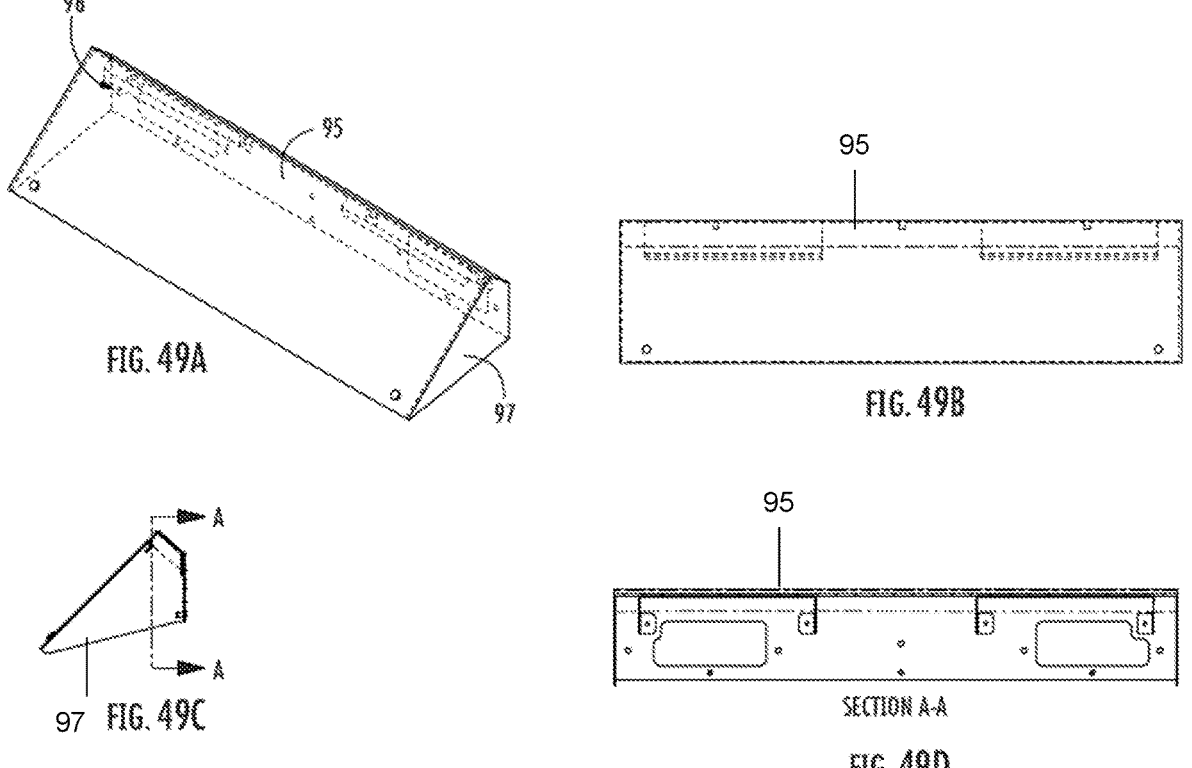

FIG. 49A illustrates the ballast bracket 95, ballast rail 96, and ballast gusset 97 of the system 100.

FIG. 49B illustrates the ballast bracket 95, ballast rail 96, and ballast gusset 97 of the system 100.

FIG. 49C illustrates the ballast bracket 95, ballast rail 96, and ballast gusset 97 of the system 100.

FIG. 49D illustrates the ballast bracket 95, ballast rail 96, and ballast gusset 97 of the system 100.

FIG. 50A illustrates the ballast bracket 95 of the system 100.

FIG. 50B illustrates the ballast bracket 95 of the system 100.

FIG. 50C illustrates the ballast bracket 95 of the system 100.

FIG. 50D illustrates the ballast bracket 95 of the system 100.

Figures 51A, 51B, 51C, 51D, 51E:
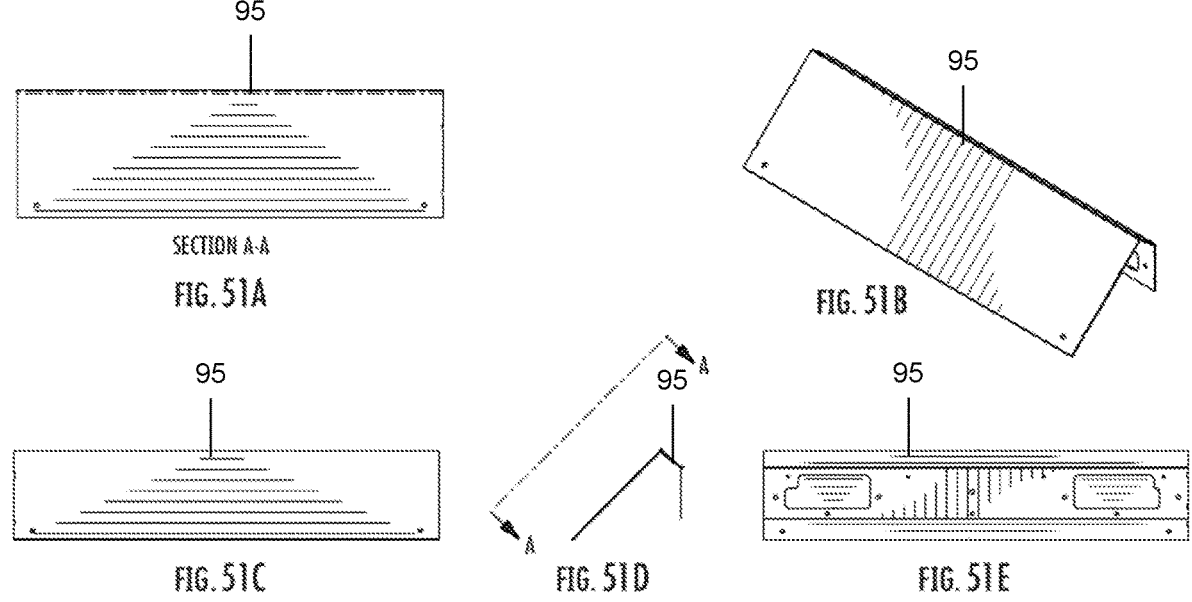

FIG. 51A illustrates a ballast bracket of the system 100.

FIG. 51B illustrates a ballast bracket of the system 100.

FIG. 51C illustrates a ballast bracket of the system 100.

FIG. 51D illustrates a ballast bracket of the system 100.

FIG. 51E illustrates a ballast bracket of the system 100.

Figures 52A, 52B, 52C, 52D:
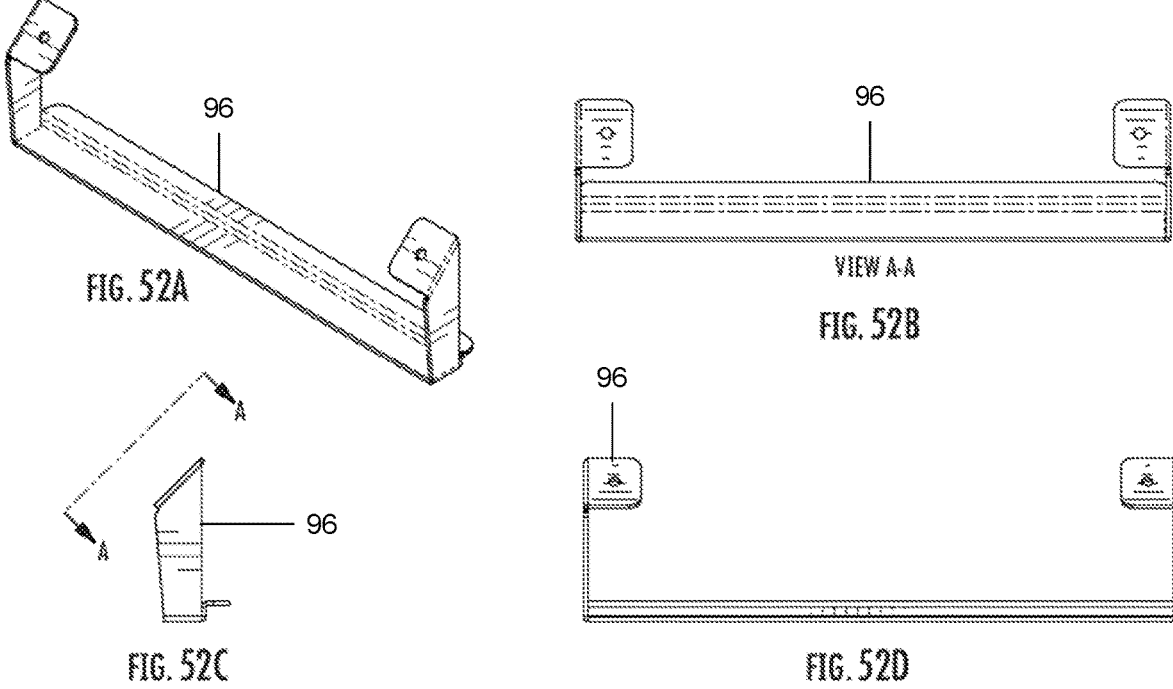

FIG. 52A illustrates a ballast rail of the system 100.

FIG. 52B illustrates a ballast rail of the system 100.

FIG. 52C illustrates a ballast rail of the system 100.

FIG. 52D illustrates a ballast rail of the system 100.

Figures 53A, 53B, 53C:
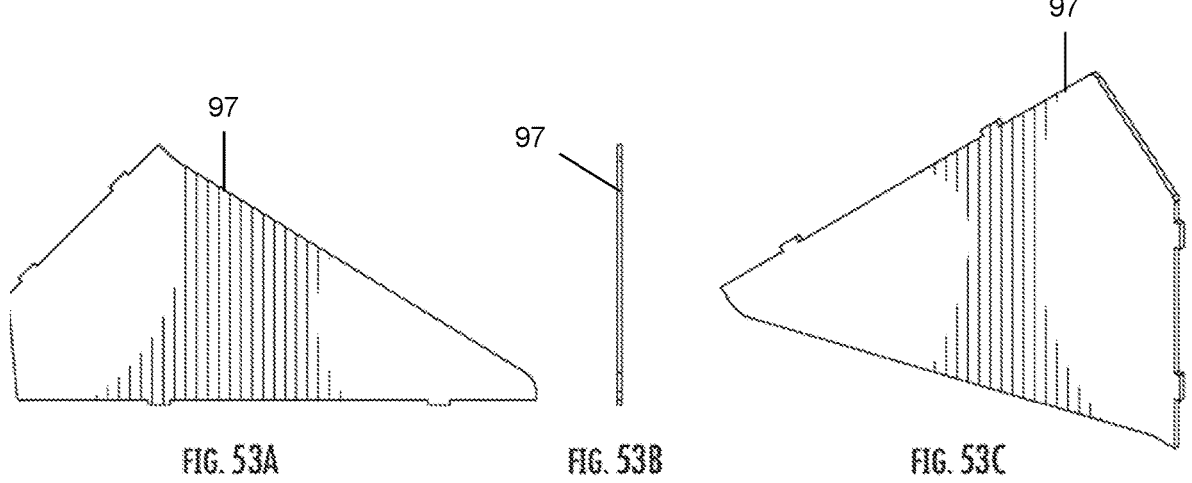

FIG. 53A illustrates ballast gusset of the system 100.

FIG. 53B illustrates ballast gusset of the system 100.

FIG. 53C illustrates ballast gusset of the system 100.

FIG. 54A illustrates first control rib 185 of the system 100.

FIG. 54B illustrates first control rib 185 of the system 100.

FIG. 54C illustrates first control rib 185 of the system 100.

FIG. 55A illustrates second control rib 186 of the system 100.

FIG. 55B illustrates second control rib 186 of the system 100.

FIG. 55C illustrates second control rib 186 of the system 100.

Figures 56A, 56B, 56C, 56D:
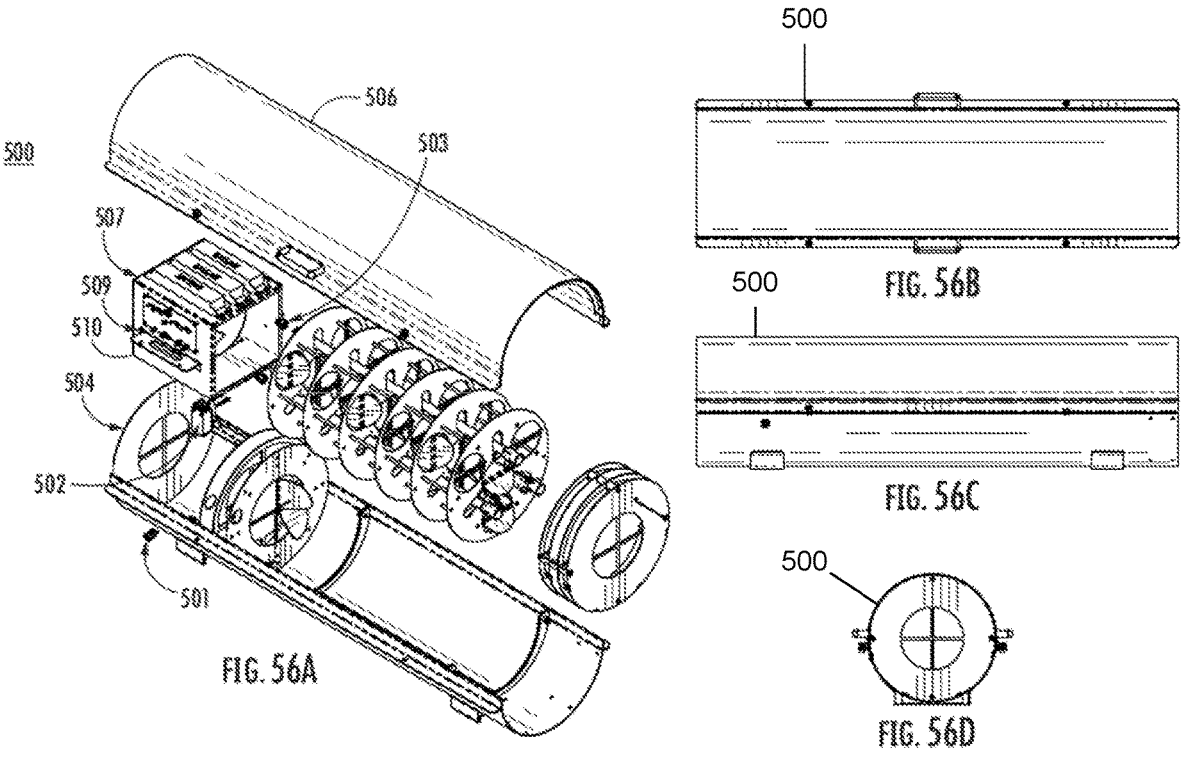

FIG. 56A illustrates a system 500 according to an embodiment of the present disclosure.

FIG. 56B illustrates a system 500 according to an embodiment of the present disclosure.

FIG. 56C illustrates a system 500 according to an embodiment of the present disclosure.

FIG. 56D illustrates a system 500 according to an embodiment of the present disclosure.

Figures 57A, 57B, 57C, 57D, 57E, 57F:
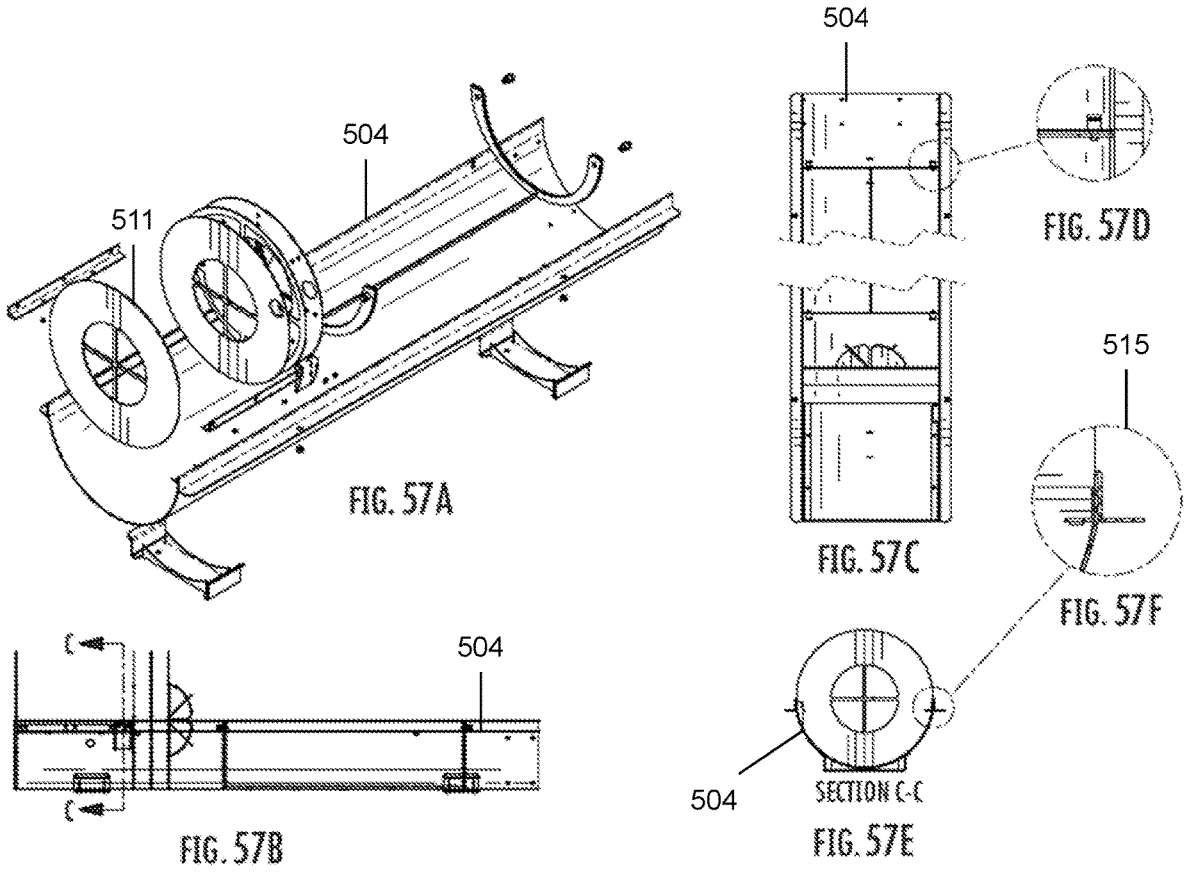

FIG. 57A illustrates components of the system 500.

FIG. 57B illustrates components of the system 500.

FIG. 57C illustrates components of the system 500.

FIG. 57D illustrates components of the system 500.

FIG. 57E illustrates components of the system 500.

FIG. 57F illustrates components of the system 500.

Figures 58A, 58B, 58C, 58D:
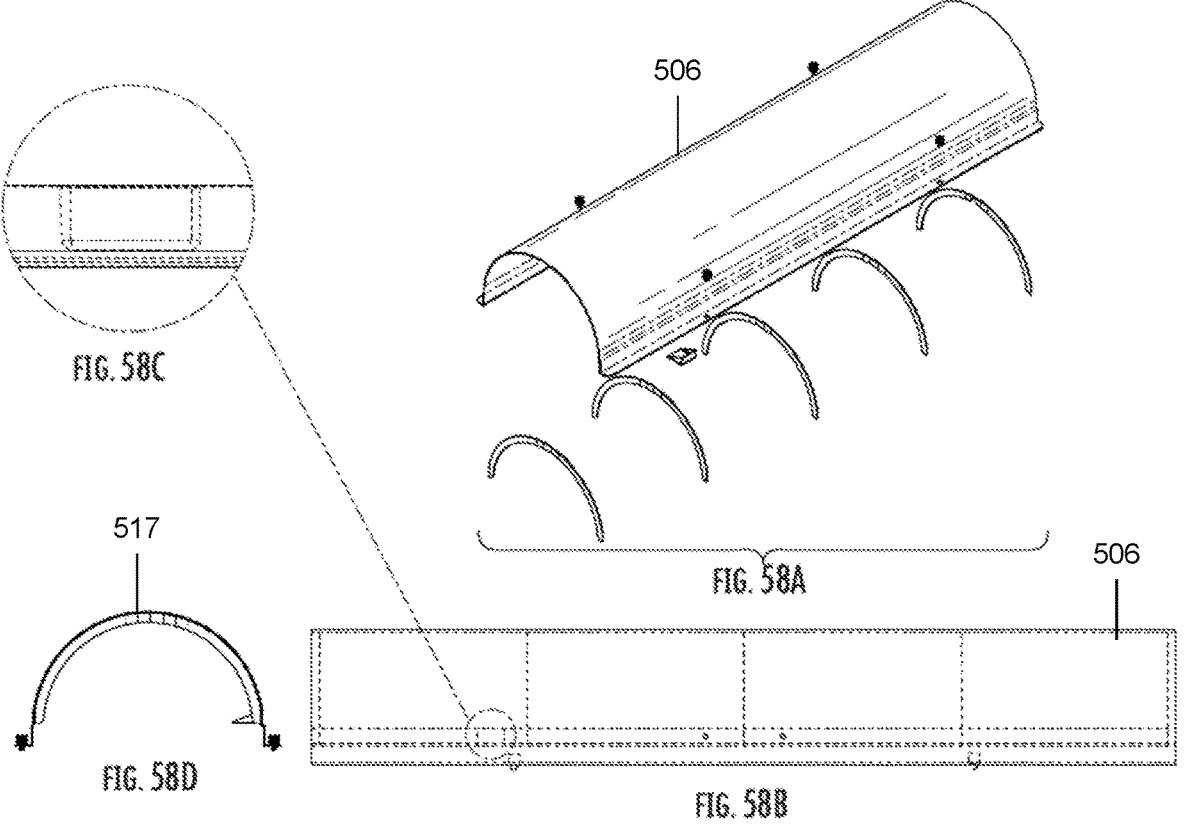

FIG. 58A illustrates components of the system 500.

FIG. 58B illustrates components of the system 500.

FIG. 58C illustrates components of the system 500.

FIG. 58D illustrates components of the system 500.

Figures 59A, 59B, 59C, 59D, 59E:
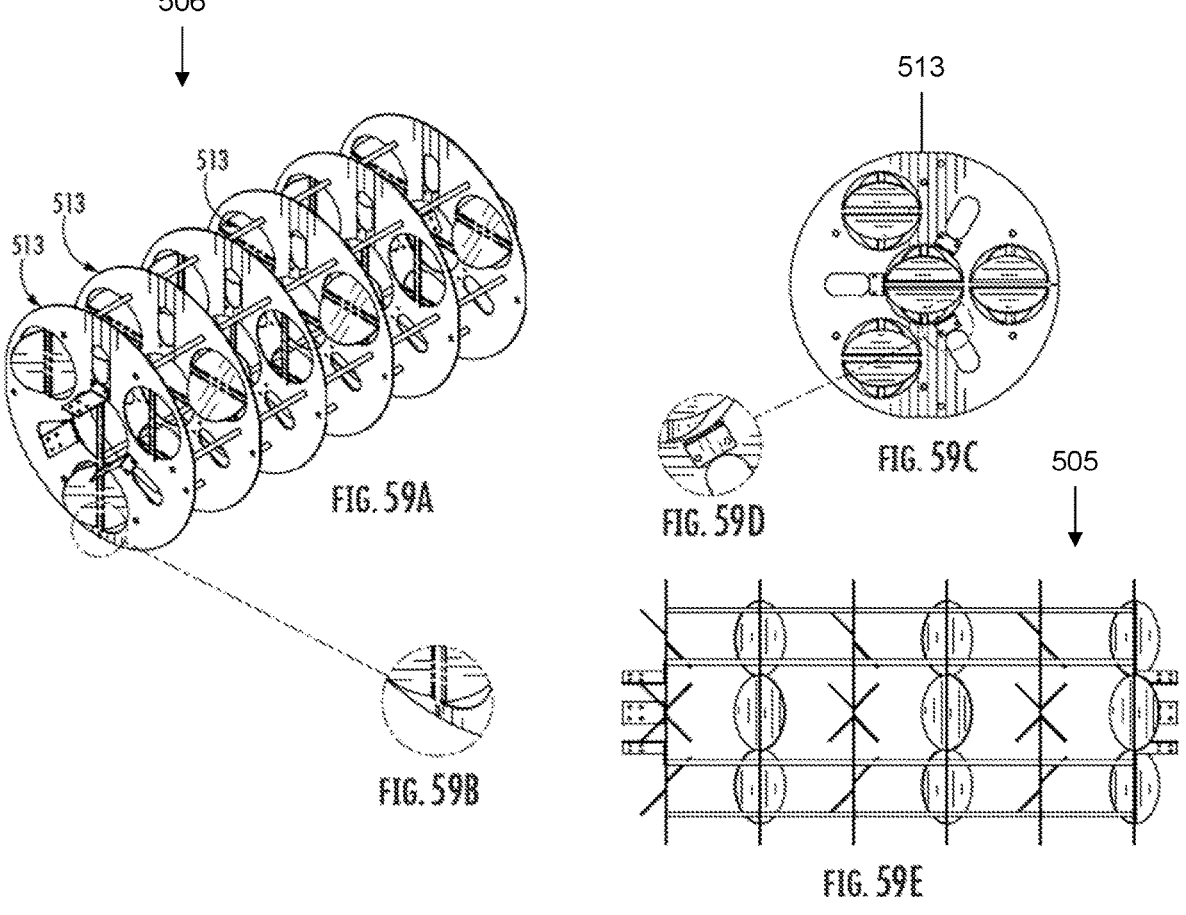

FIG. 59A illustrates an air baffle assembly 505.

FIG. 59B illustrates an air baffle assembly 505.

FIG. 59C illustrates an air baffle assembly 505.

FIG. 59D illustrates an air baffle assembly 505.

FIG. 59E illustrates an air baffle assembly 505.

Figures 60A, 60B, 60C, 60D:
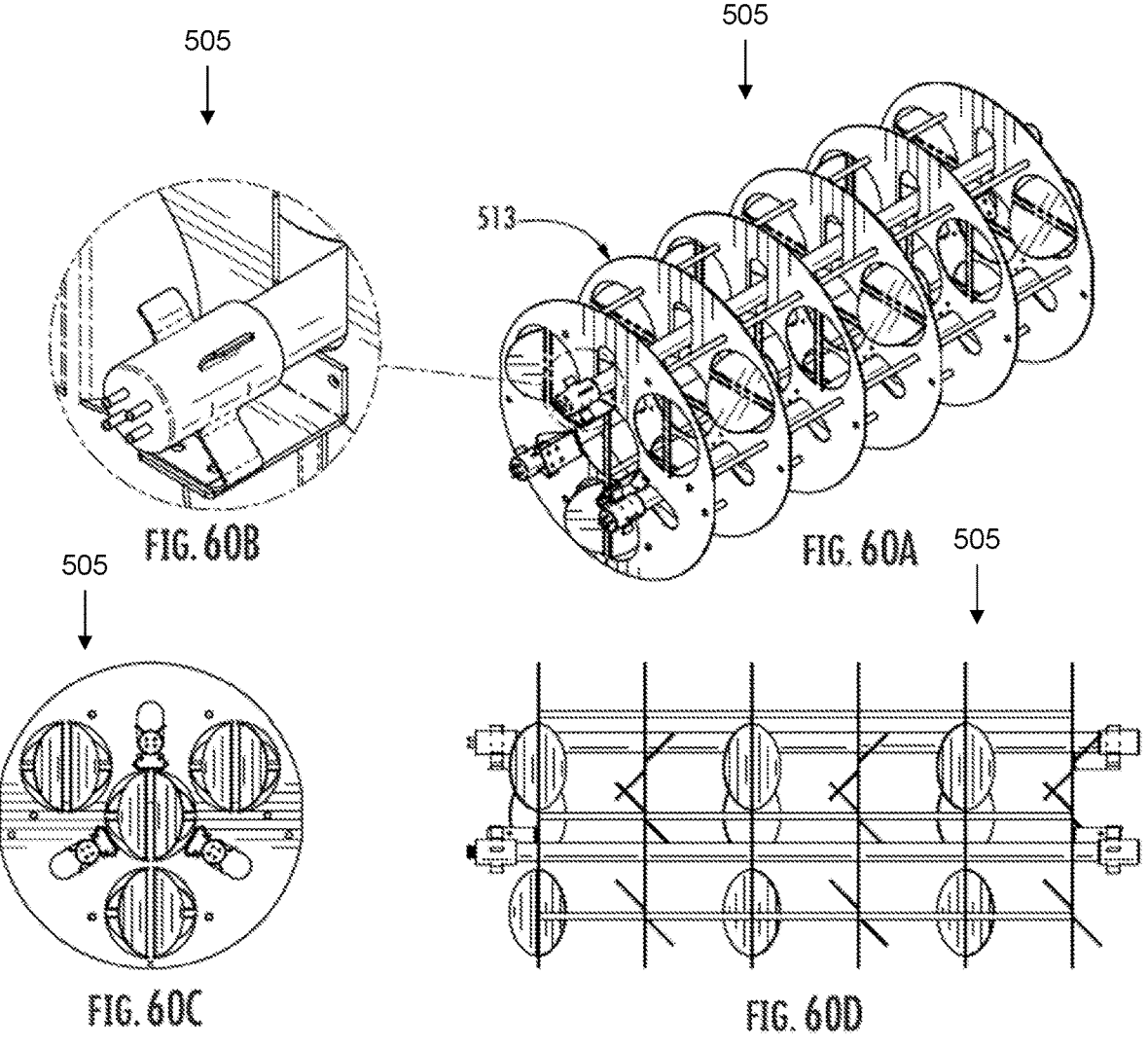

FIG. 60A illustrates an air baffle assembly 505.

FIG. 60B illustrates an air baffle assembly 505.

FIG. 60C illustrates an air baffle assembly 505.

FIG. 60D illustrates an air baffle assembly 505.

Figures 61A, 61B, 61C, 61D:
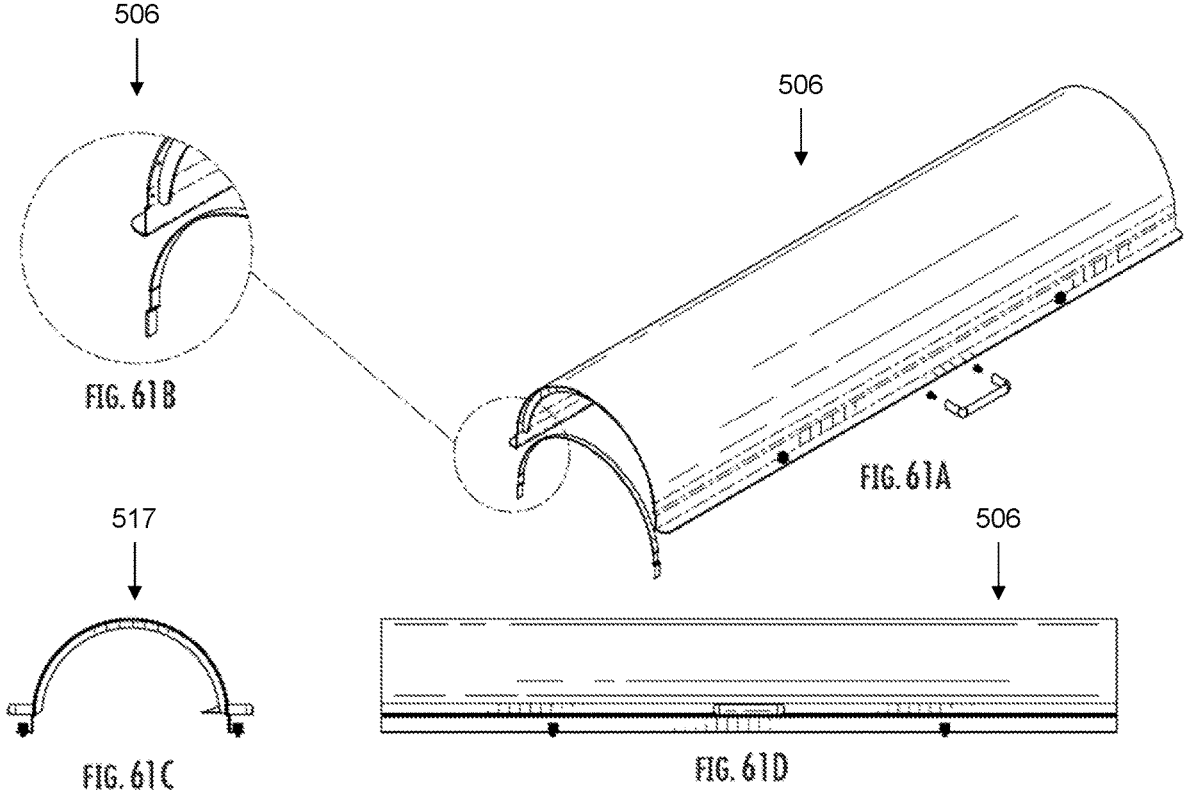

FIG. 61A illustrates a tube top.

FIG. 61B illustrates a tube top.

FIG. 61C illustrates a tube top.

FIG. 61D illustrates a tube top.

Figures 62A, 62B, 62C, 62D, 62E:
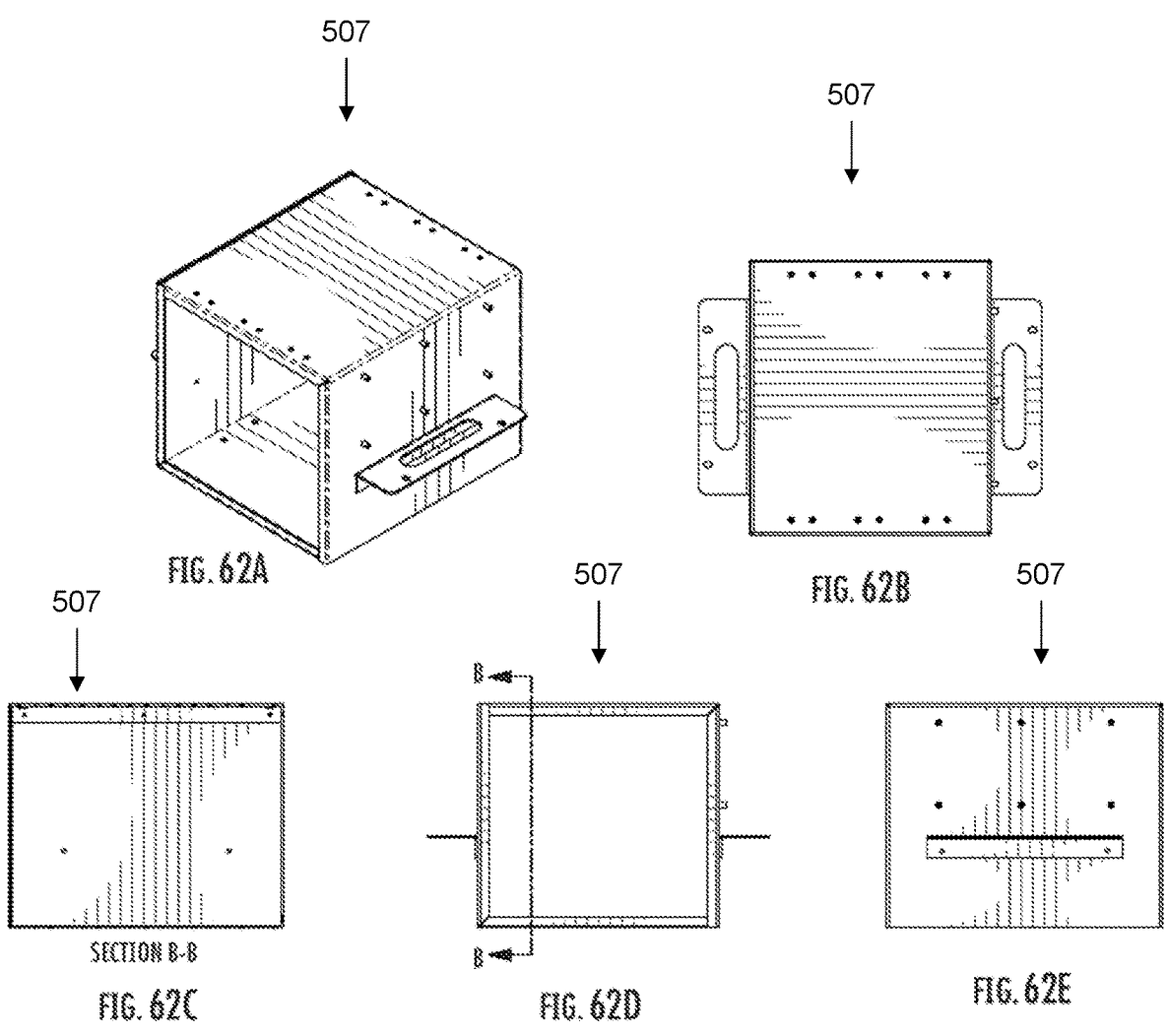

FIG. 62A illustrates an electronics mount.

FIG. 62B illustrates an electronics mount.

FIG. 62C illustrates an electronics mount.

FIG. 62D illustrates an electronics mount.

FIG. 62E illustrates an electronics mount.

Figures 63A, 63B, 63C, 63D:
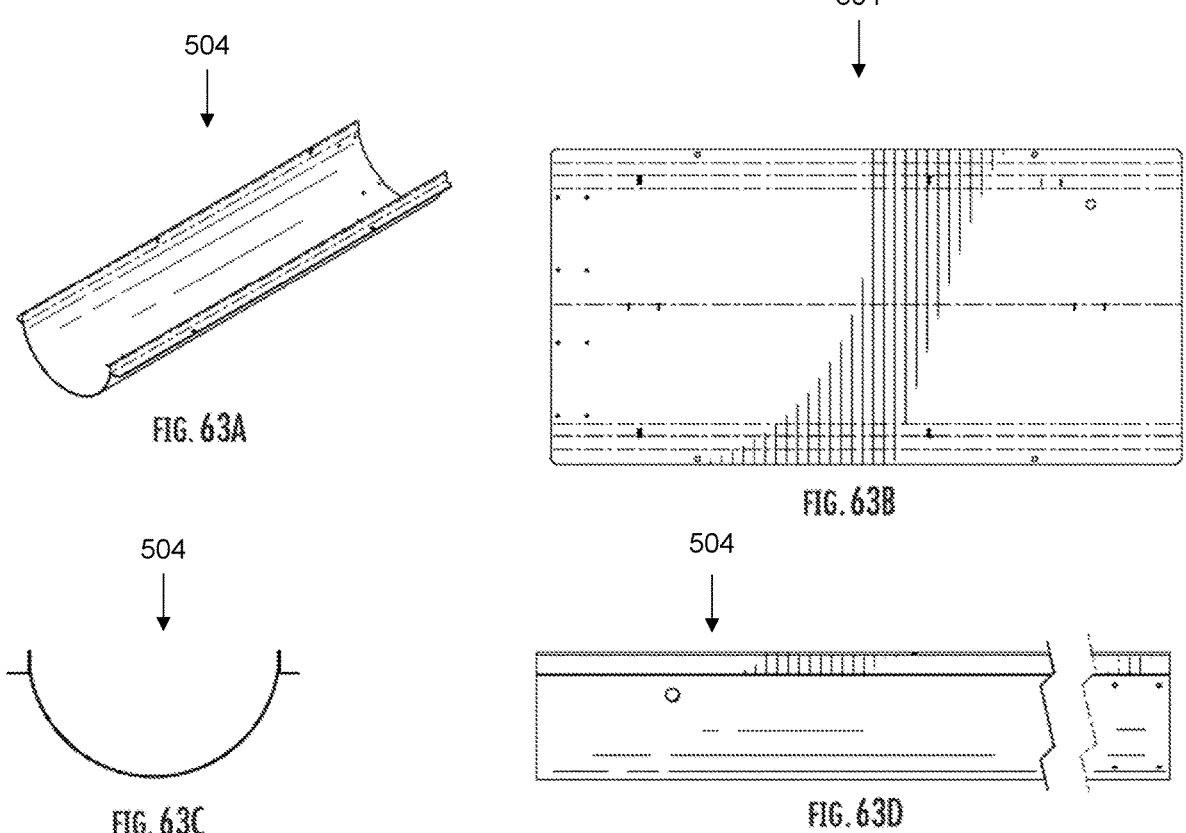

FIG. 63A illustrates a tube bottom.

FIG. 63B illustrates a tube bottom.

FIG. 63C illustrates a tube bottom.

FIG. 63D illustrates a tube bottom.

Figures 64A, 64B, 64C, 64D:
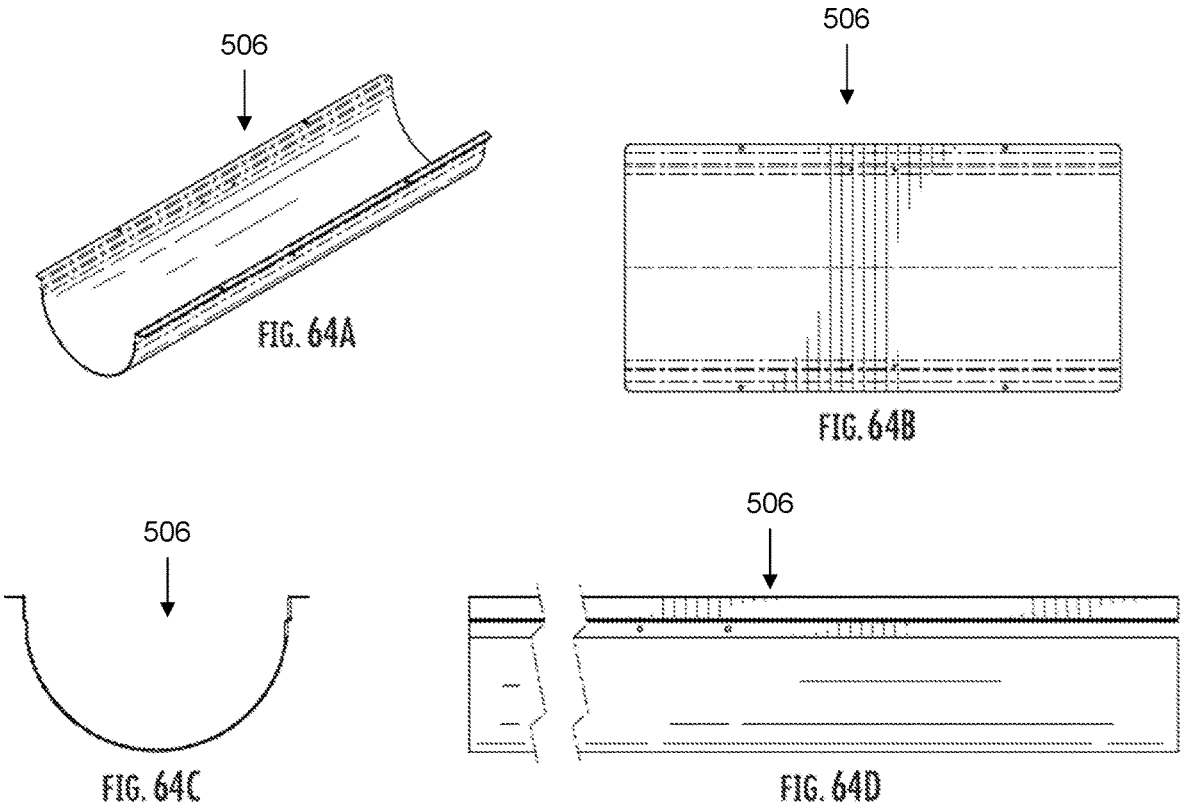

FIG. 64A illustrates a tube top.

FIG. 64B illustrates a tube top.

FIG. 64C illustrates a tube top.

FIG. 64D illustrates a tube top.

Figures 65A, 65B, 65C:
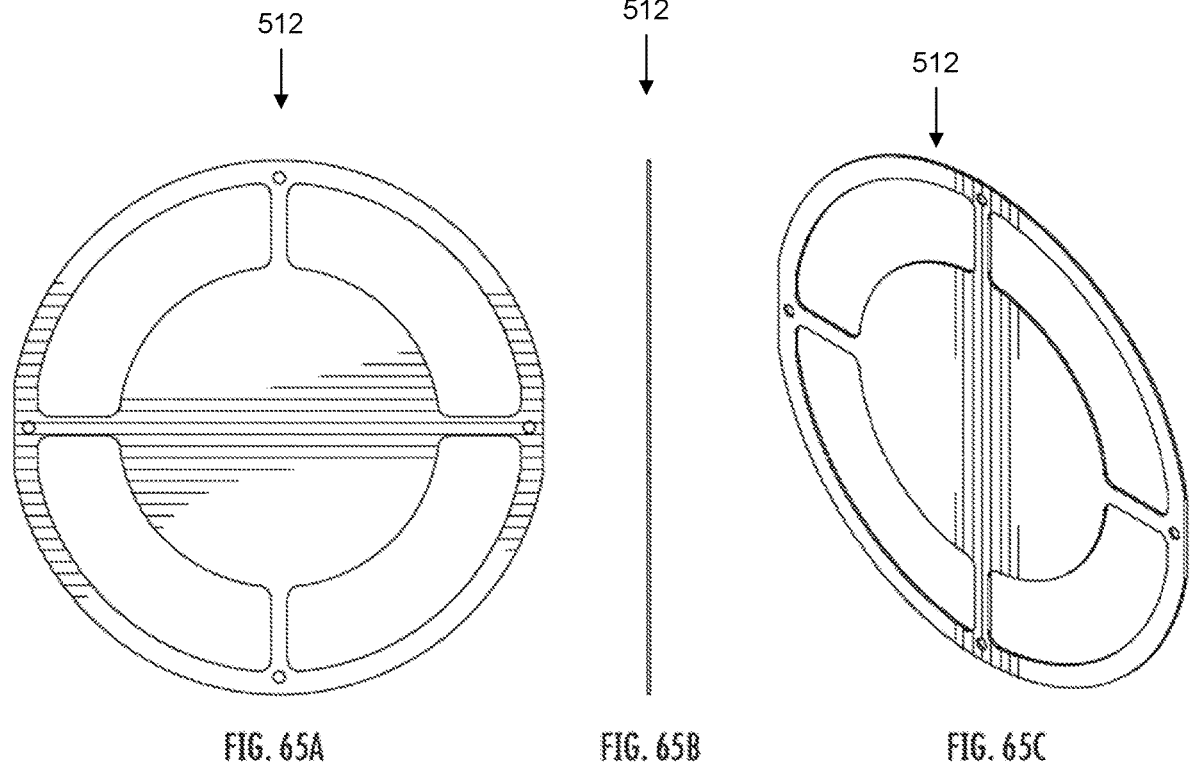

FIG. 65A illustrates a divider.

FIG. 65B illustrates a divider.

FIG. 65C illustrates a divider.

Figures 66A, 66B, 66C:
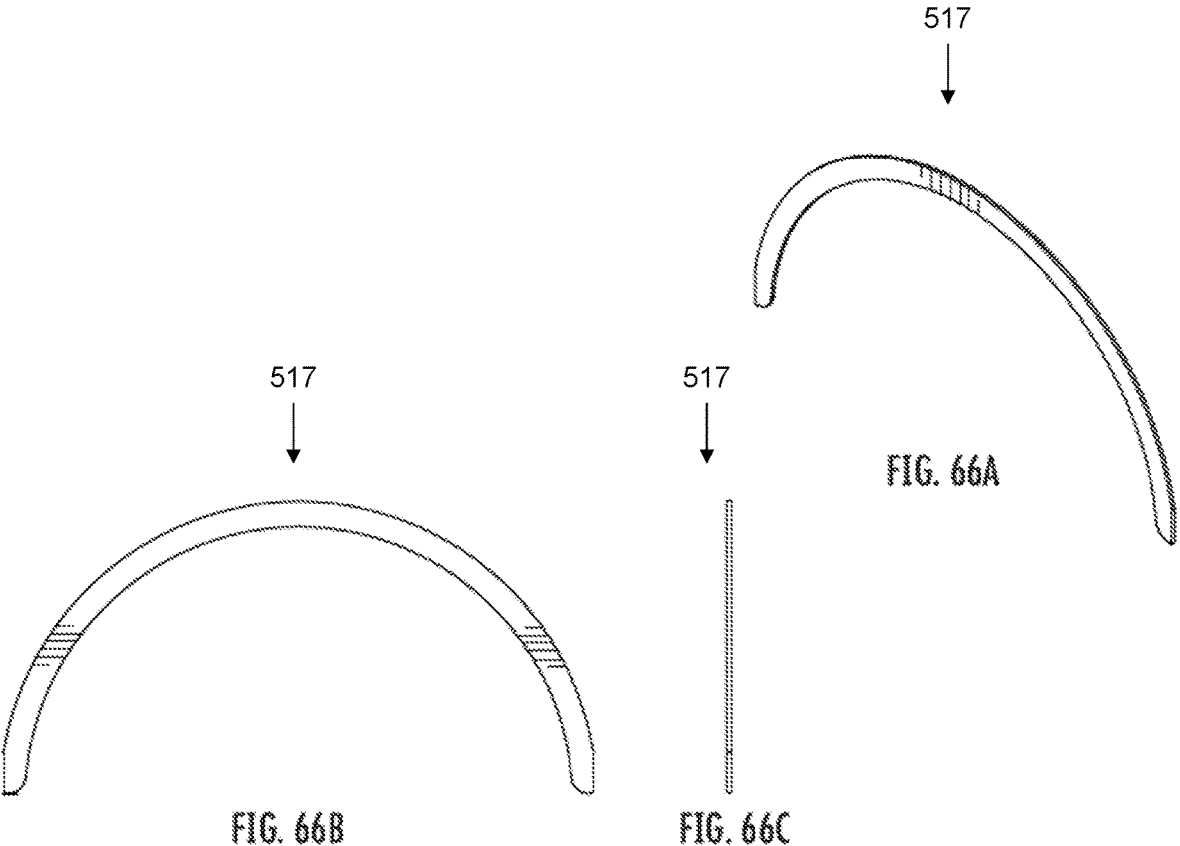

FIG. 66A illustrates a lid rib.

FIG. 66B illustrates a lid rib.

FIG. 66C illustrates a lid rib.

Figures 67A, 67B, 67C, 67D, 67E:
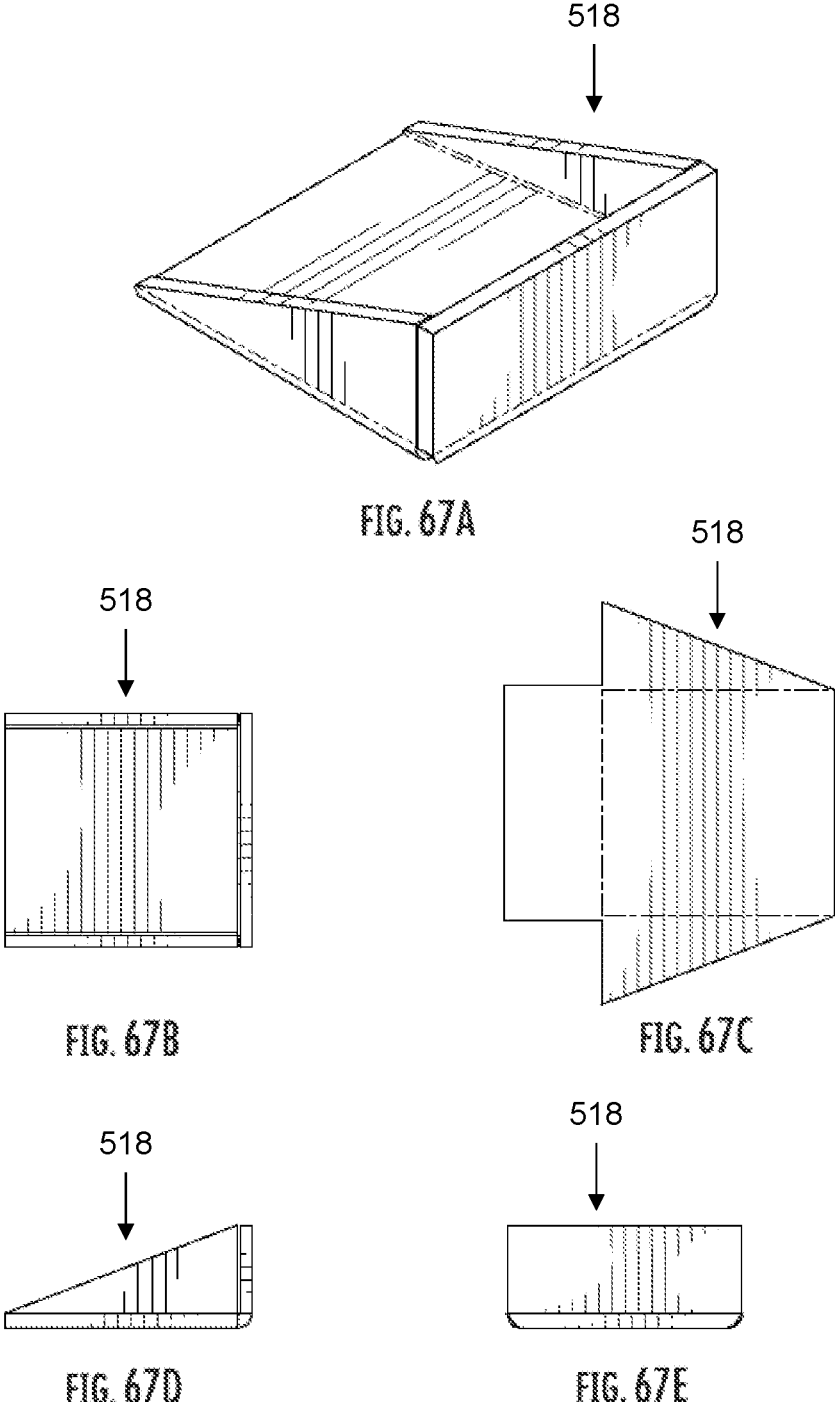

FIG. 67A illustrates a lock bracket.

FIG. 67B illustrates a lock bracket.

FIG. 67C illustrates a lock bracket.

FIG. 67D illustrates a lock bracket.

FIG. 67E illustrates a lock bracket.

Figures 68A, 68B, 68C, 68D:
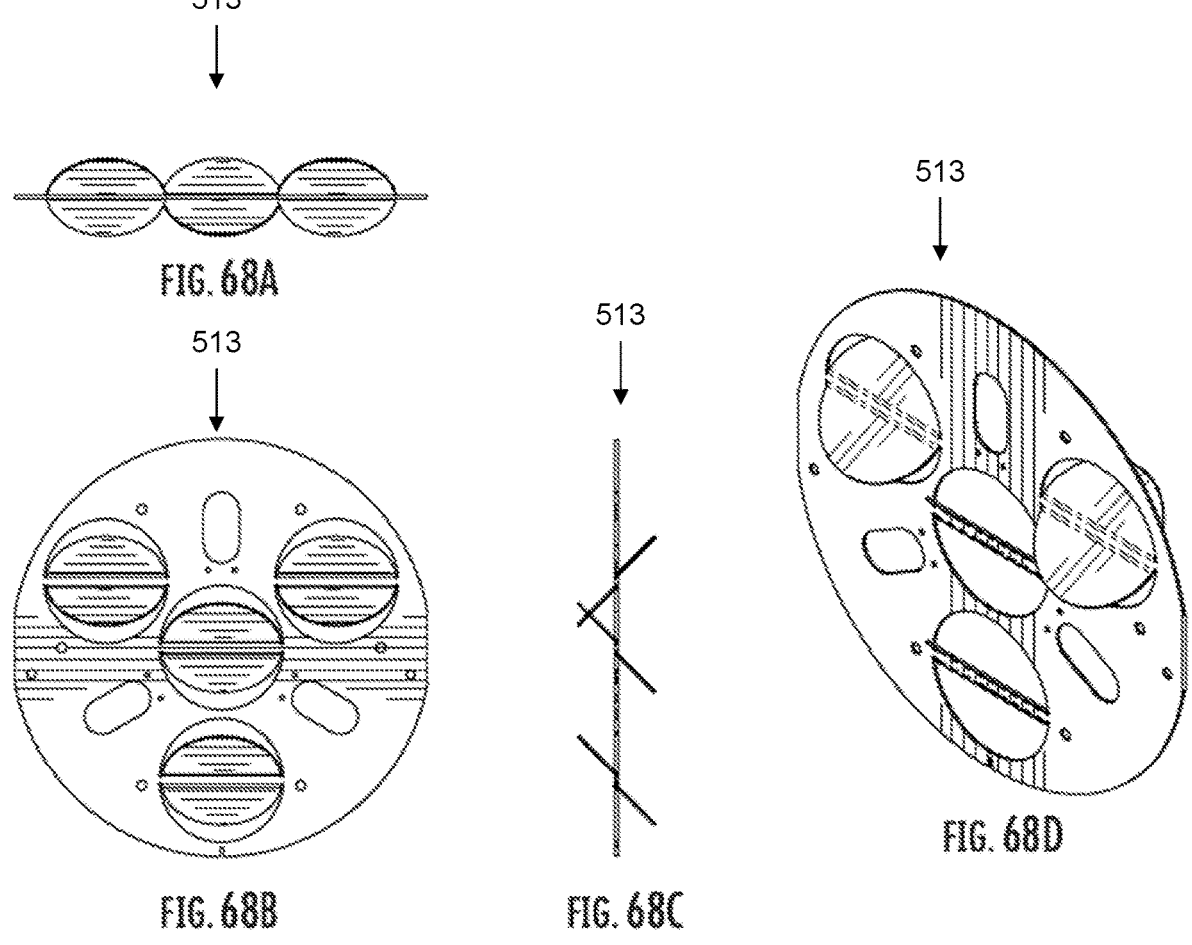

FIG. 68A illustrates a first mixer plate.

FIG. 68B illustrates a first mixer plate.

FIG. 68C illustrates a first mixer plate.

FIG. 68D illustrates a first mixer plate.

Figures 69A, 69B, 69C, 69D:
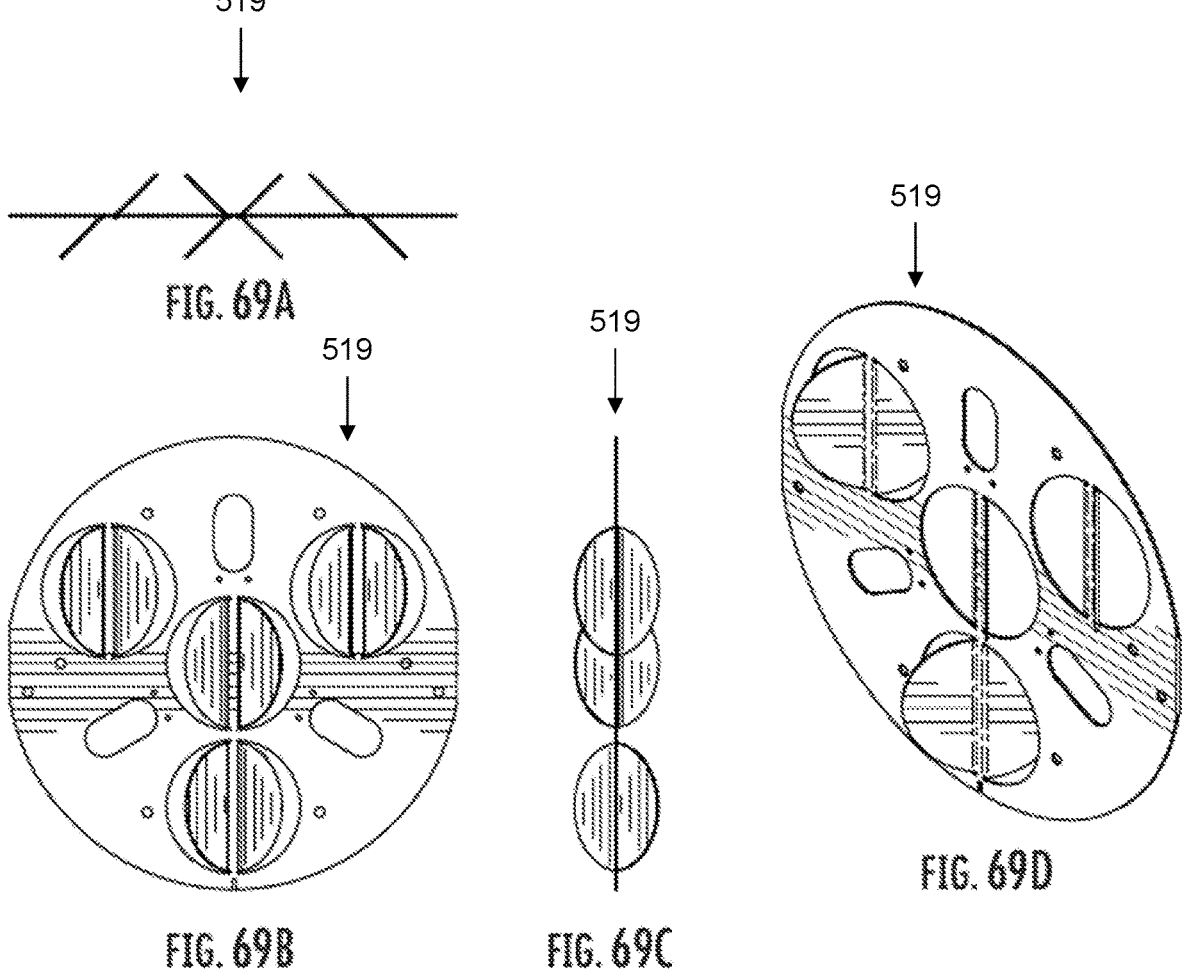

FIG. 69A illustrates a second mixer plate.

FIG. 69B illustrates a second mixer plate.

FIG. 69C illustrates a second mixer plate.

FIG. 69D illustrates a second mixer plate.

Figures 70A, 70B, 70C:
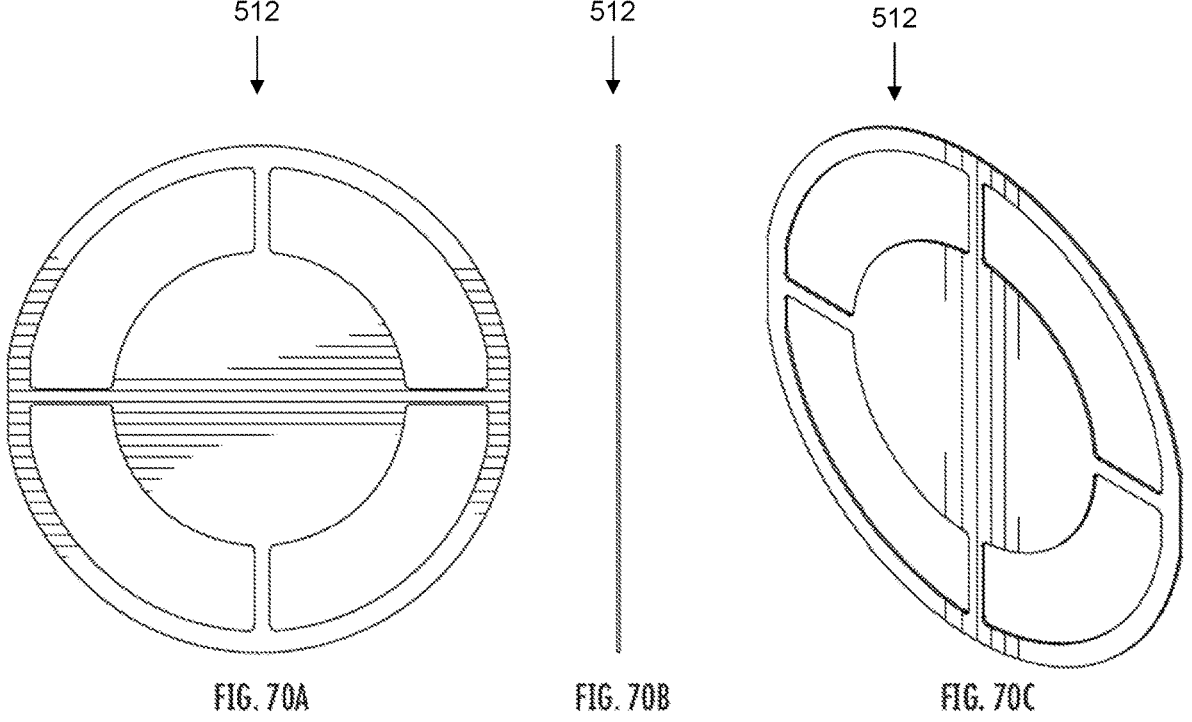

FIG. 70A illustrates a divider.

FIG. 70B illustrates a divider.

FIG. 70C illustrates a divider.

Figures 71A, 71B, 71C, 71D:
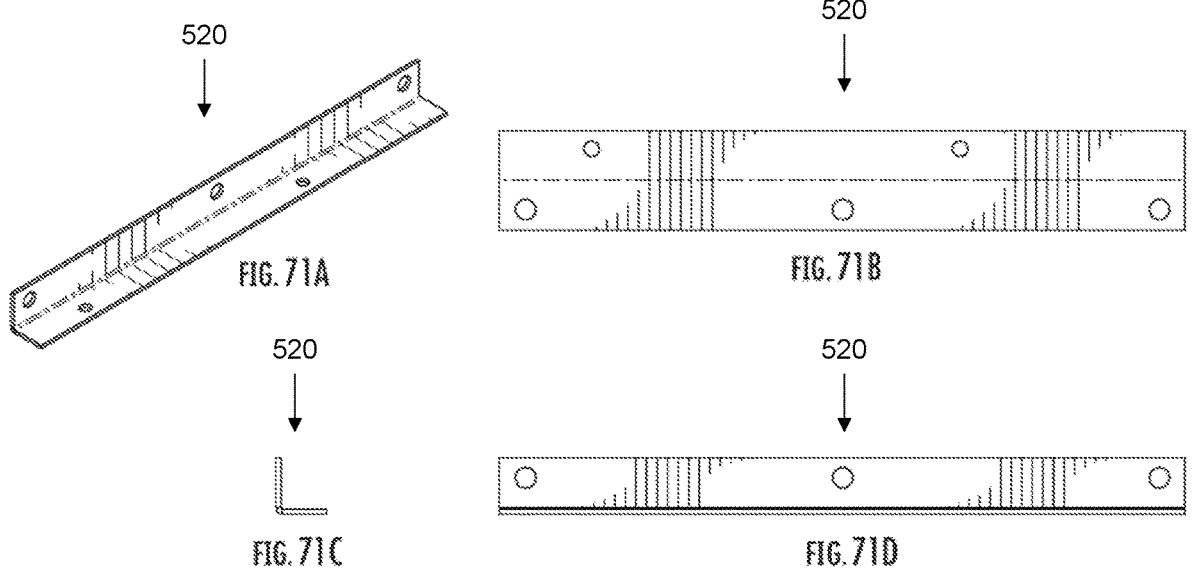

FIG. 71A illustrates a mount tab.

FIG. 71B illustrates a mount tab.

FIG. 71C illustrates a mount tab.

FIG. 71D illustrates a mount tab.

Figures 72A, 72B, 72C:
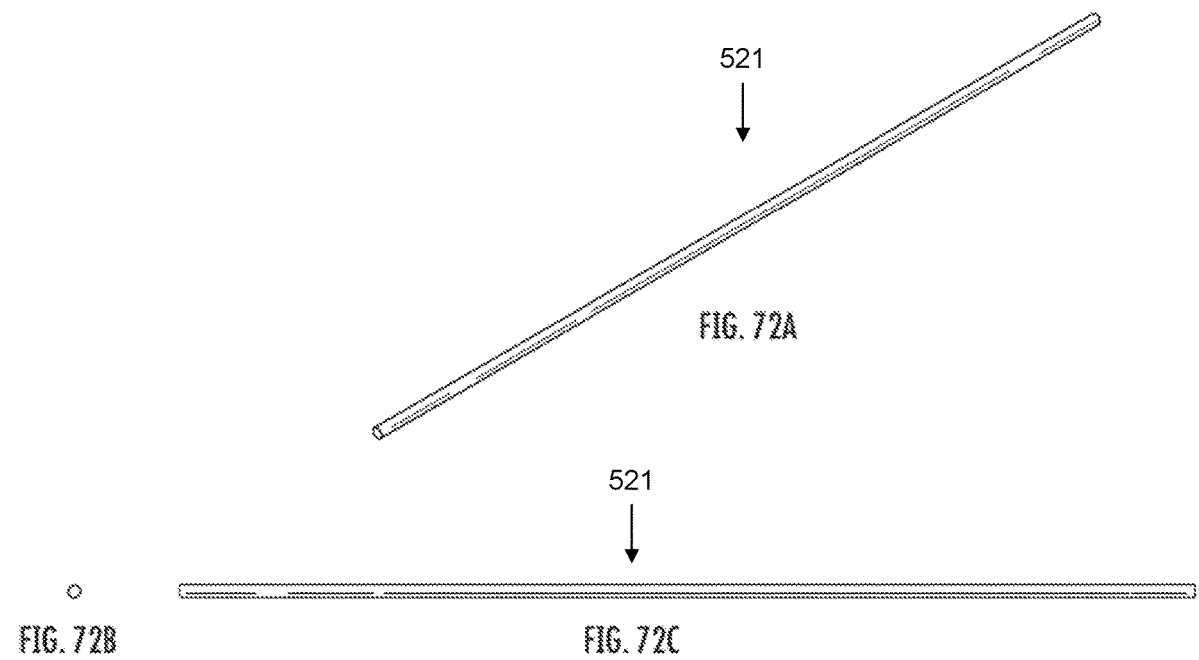

FIG. 72A illustrates a rod.

FIG. 72B illustrates a rod.

FIG. 72C illustrates a rod.

Figures 73A, 73B, 73C, 73D:
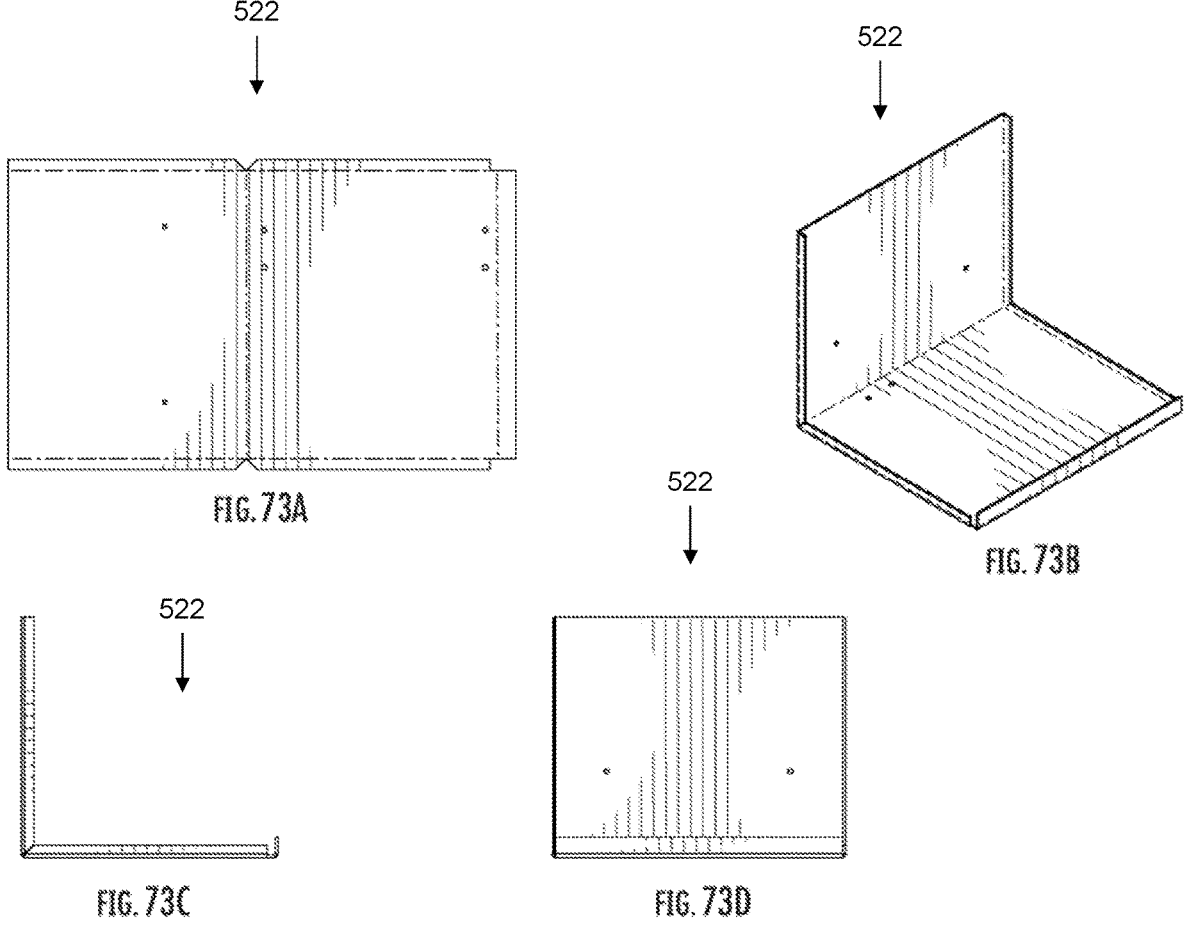

FIG. 73A illustrates a fan motor mount.

FIG. 73B illustrates a fan motor mount.

FIG. 73C illustrates a fan motor mount.

FIG. 73D illustrates a fan motor mount.

Figures 74A, 74B, 74C:
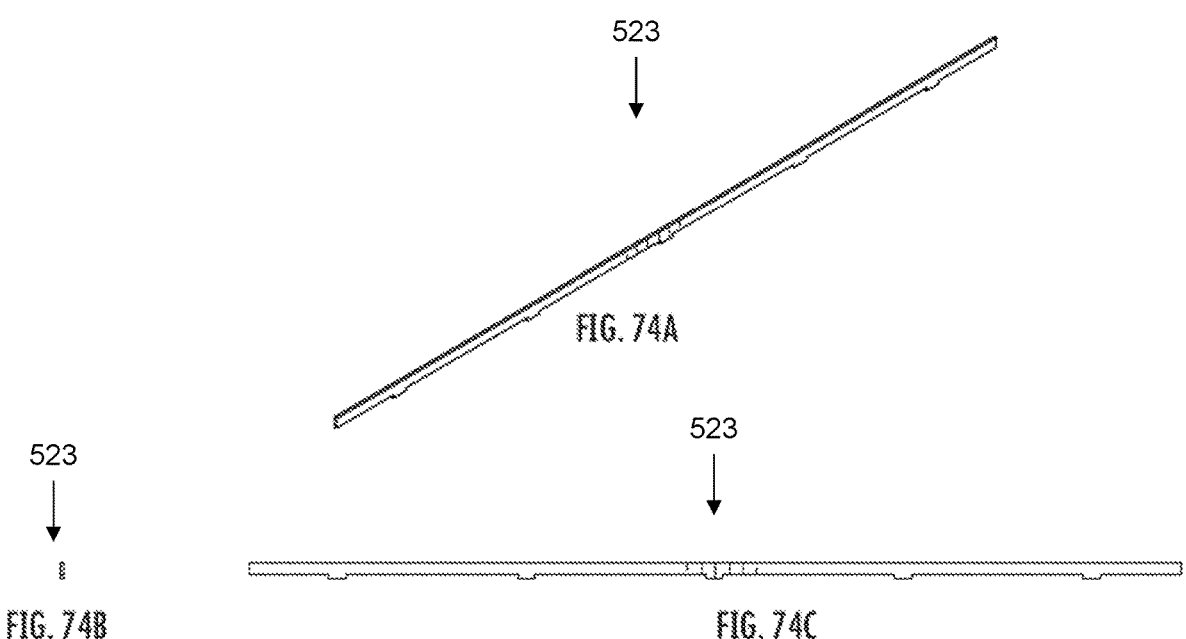

FIG. 74A illustrates a rib.

FIG. 74B illustrates a rib.

FIG. 74C illustrates a rib.

Figures 75A, 75B, 75C, 75D, 75E:
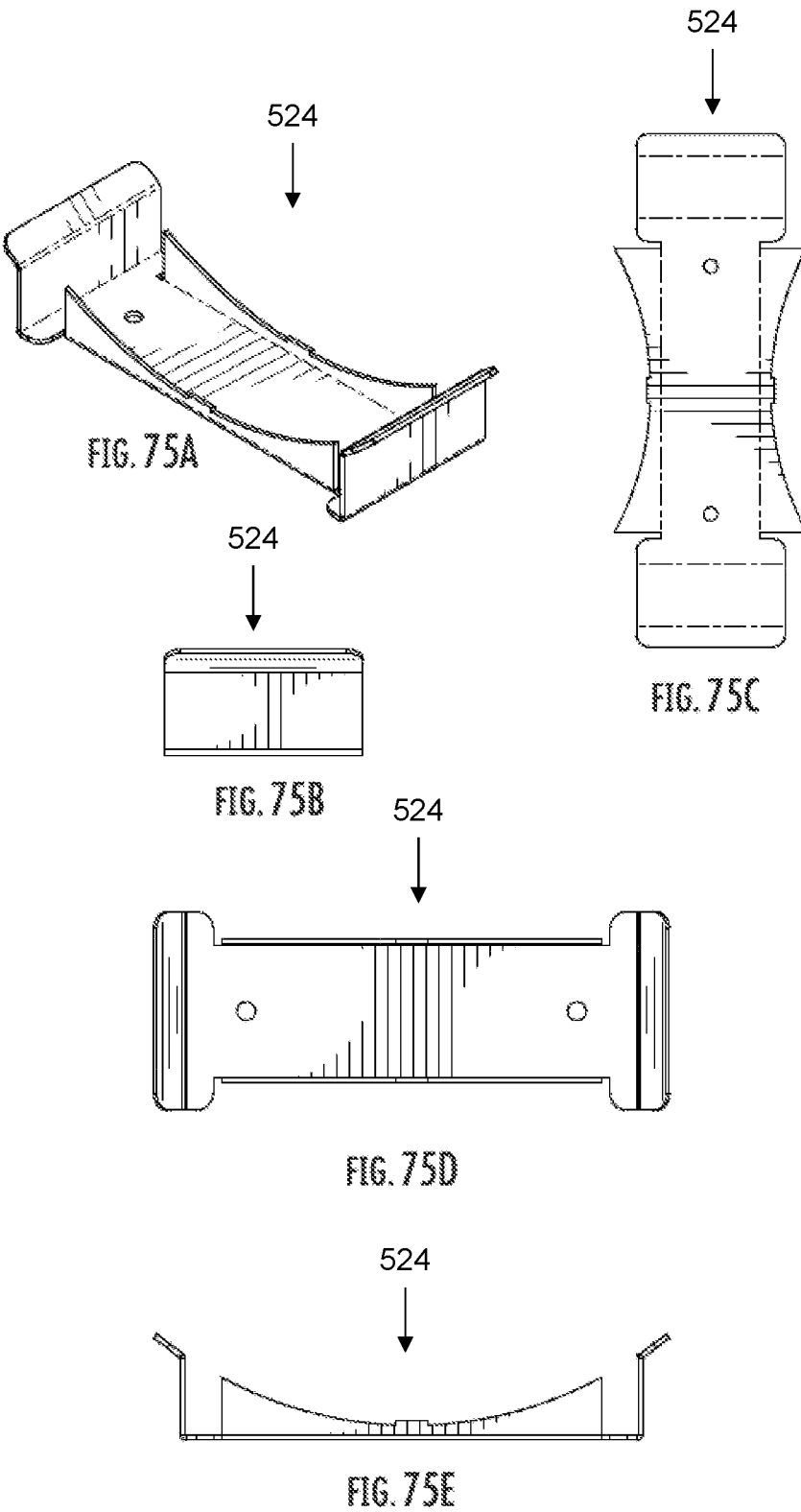

FIG. 75A illustrates a mount.

FIG. 75B illustrates a mount.

FIG. 75C illustrates a mount.

FIG. 75D illustrates a mount.

FIG. 75E illustrates a mount.

Figures 76A, 76B, 76C, 76D:
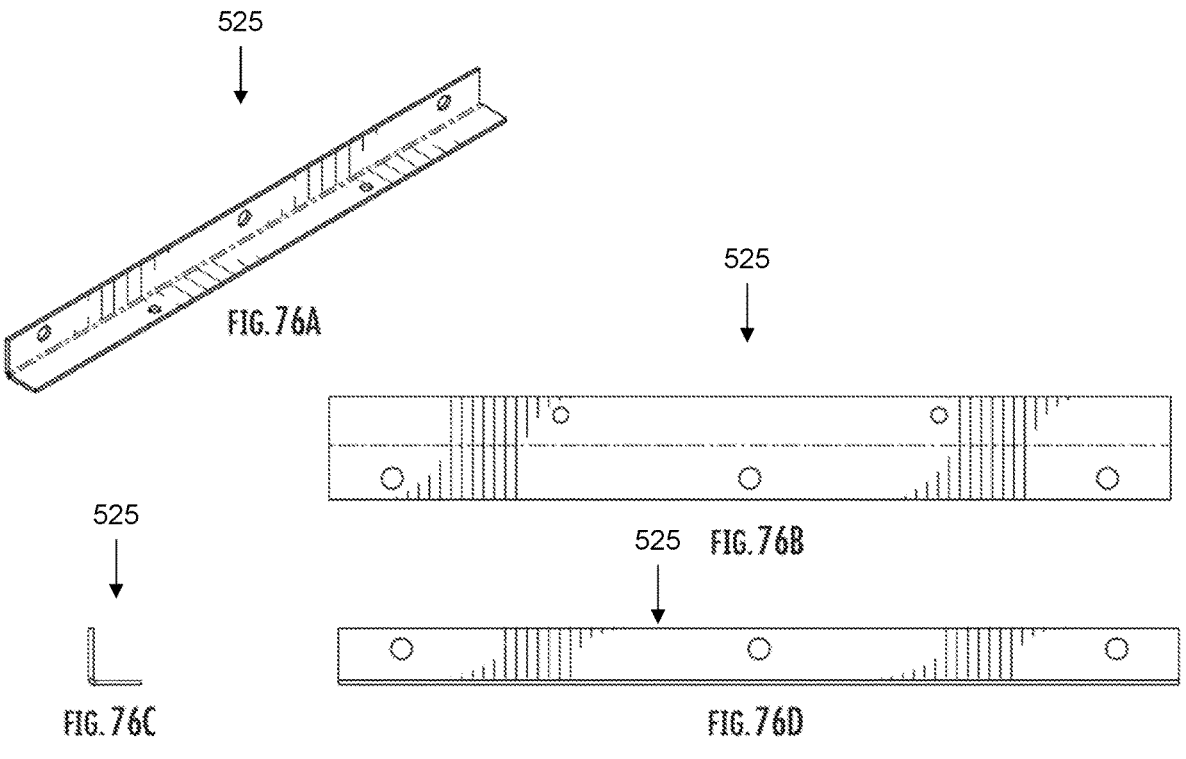

FIG. 76A illustrates a mount.

FIG. 76B illustrates a mount.

FIG. 76C illustrates a mount.

FIG. 76D illustrates a mount.

Figures 77A, 77B, 77C, 77D, 77E:
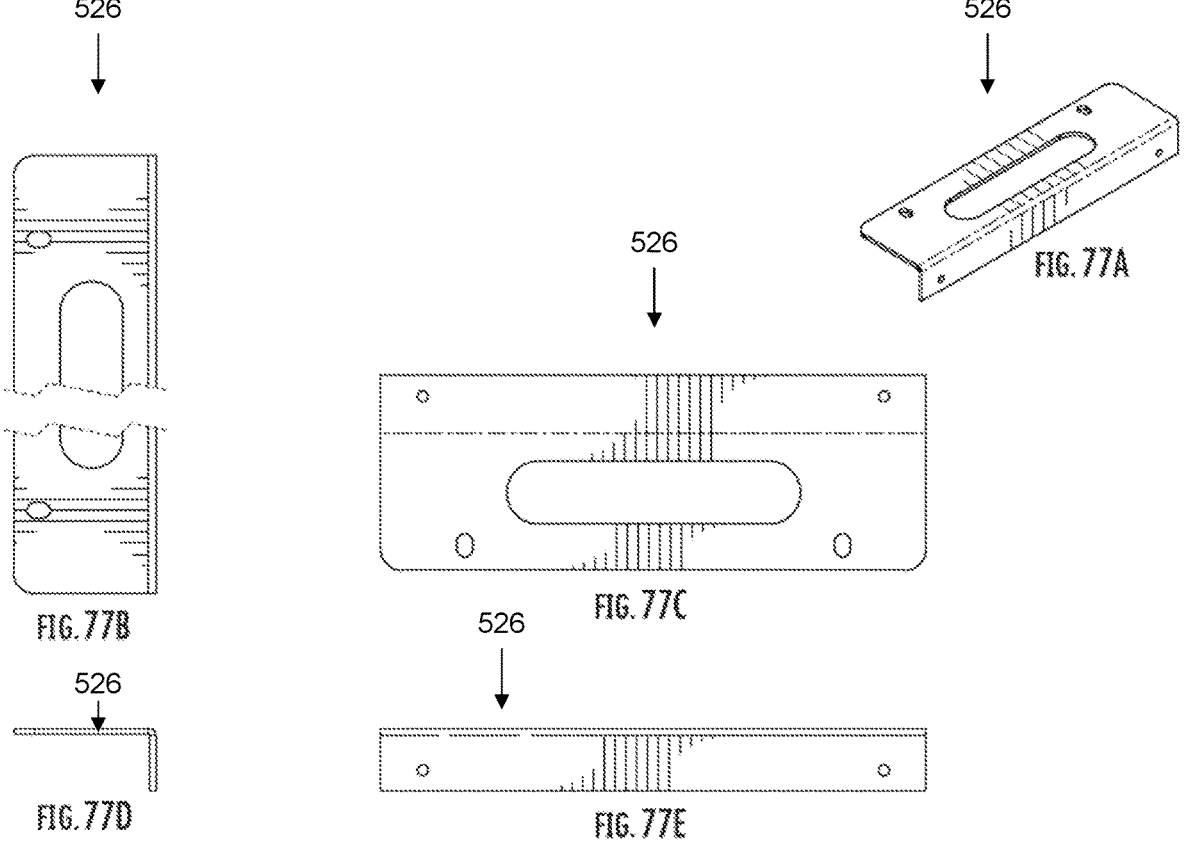

FIG. 77A illustrates a mount.

FIG. 77B illustrates a mount.

FIG. 77C illustrates a mount.

FIG. 77D illustrates a mount.

FIG. 77E illustrates a mount.

Figures 78A, 78B, 78C:
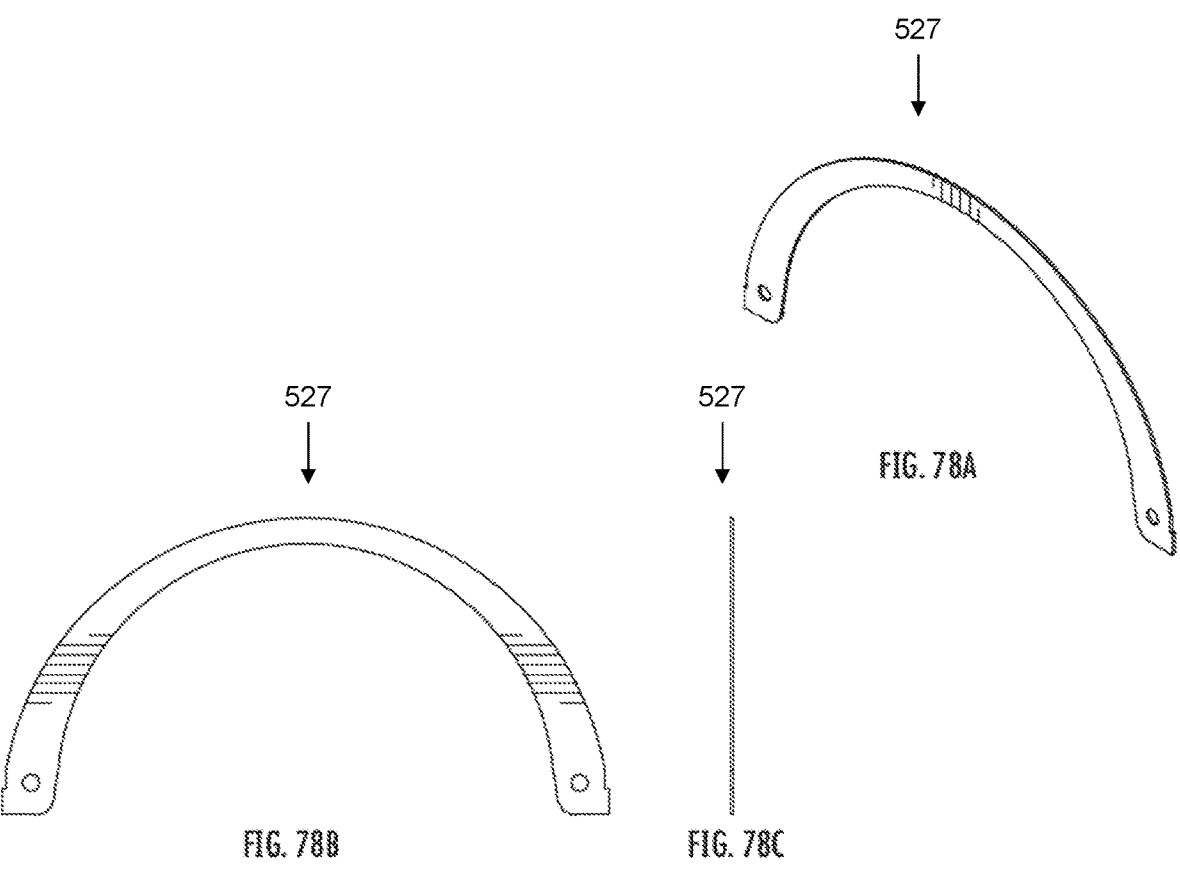

FIG. 78A illustrates a lid rib.

FIG. 78B illustrates a lid rib.

FIG. 78C illustrates a lid rib.

Figures 79A, 79B, 79C:
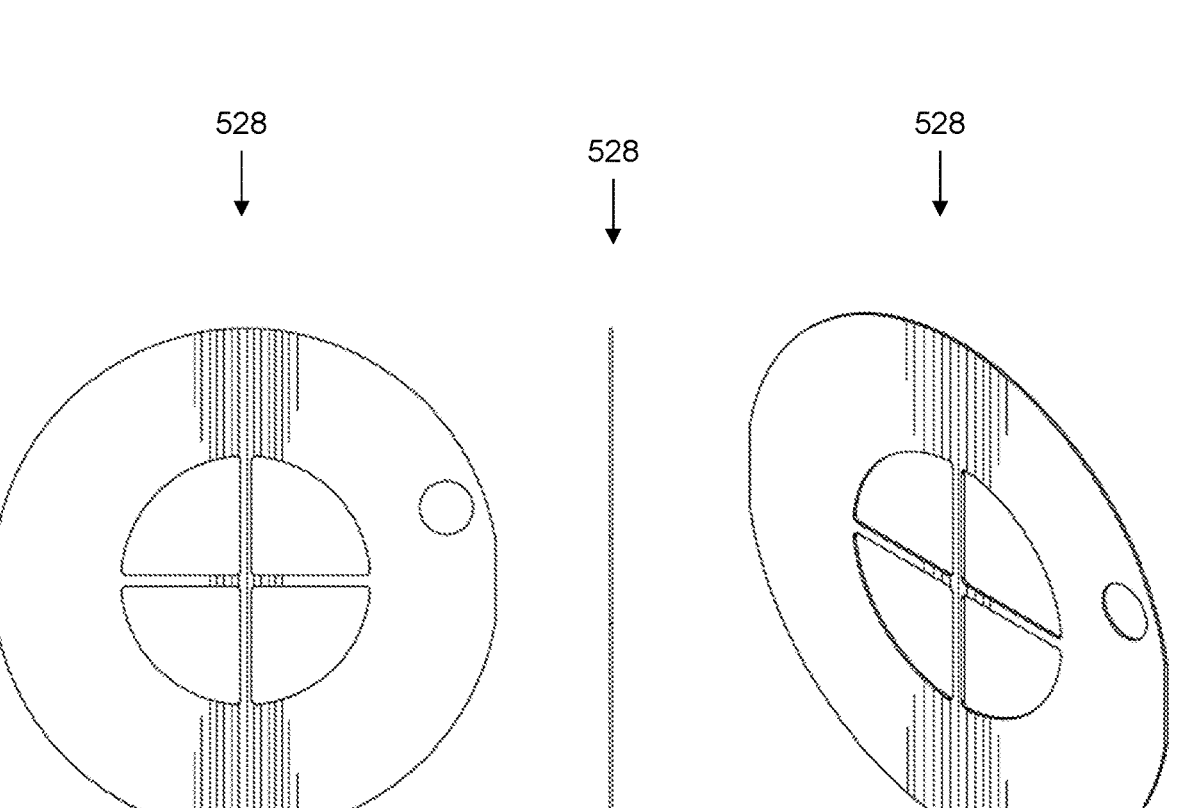

FIG. 79A illustrates a divider.

FIG. 79B illustrates a divider.

FIG. 79C illustrates a divider.

Figures 80A, 80B, 80C, 80D:
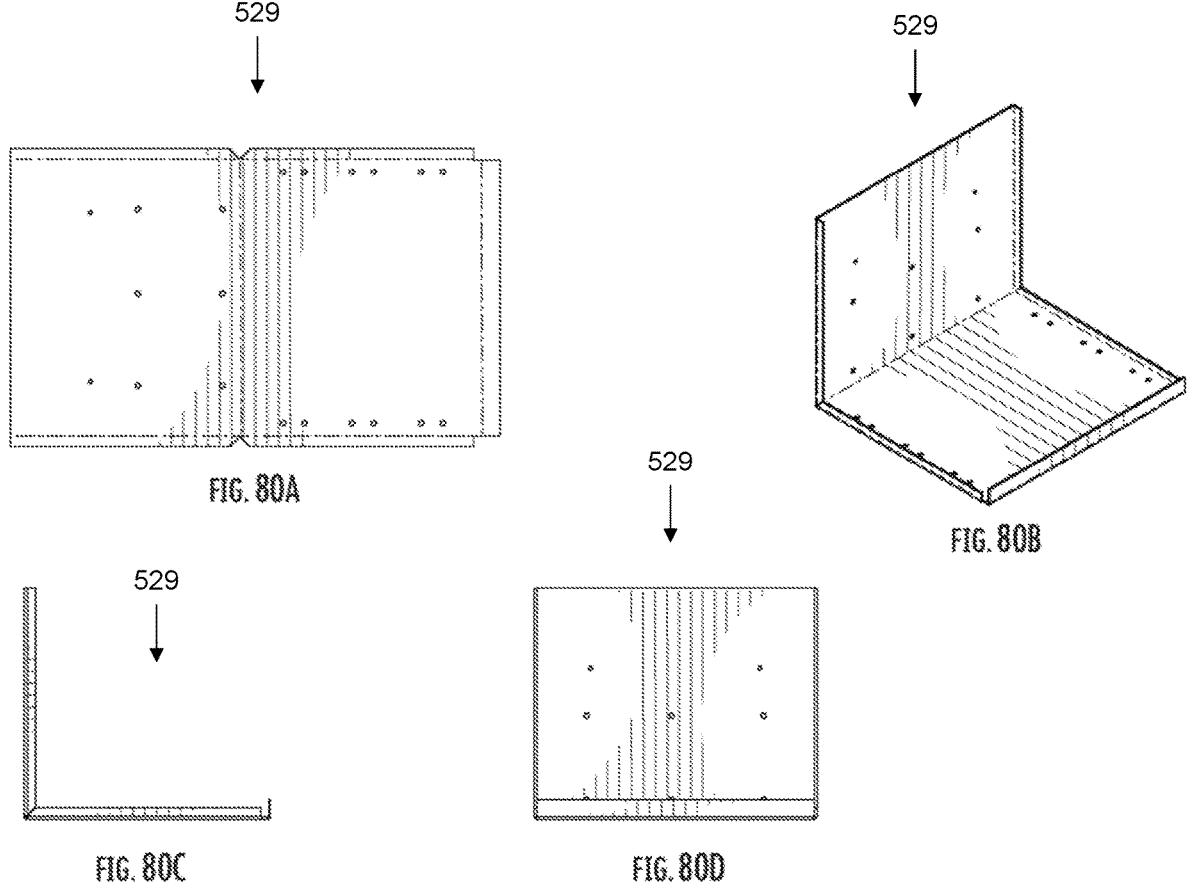

FIG. 80A illustrates a fan motor mount.

FIG. 80B illustrates a fan motor mount.

FIG. 80C illustrates a fan motor mount.

FIG. 80D illustrates a fan motor mount.

Figures 81A, 81B, 81C:
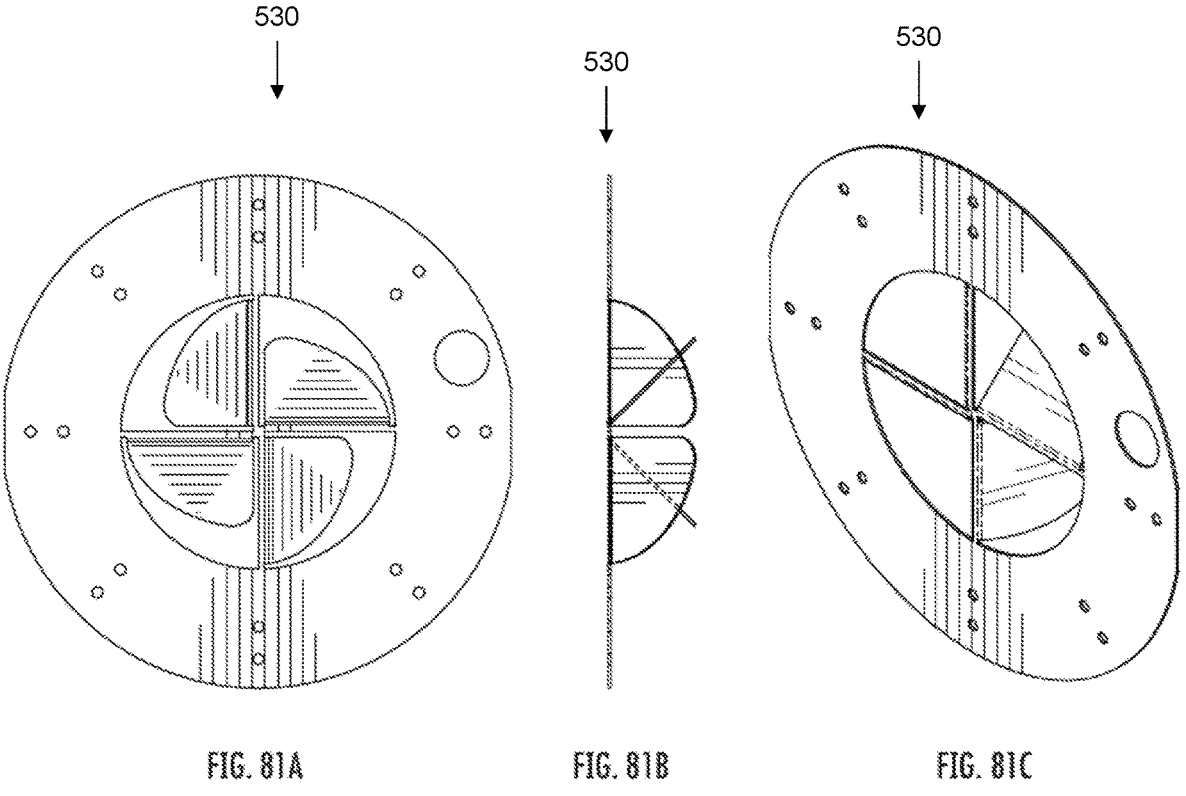

FIG. 81A illustrates a divider.

FIG. 81B illustrates a divider.

FIG. 81C illustrates a divider.

Figures 82A, 82B, 82C, 82D, 82E:
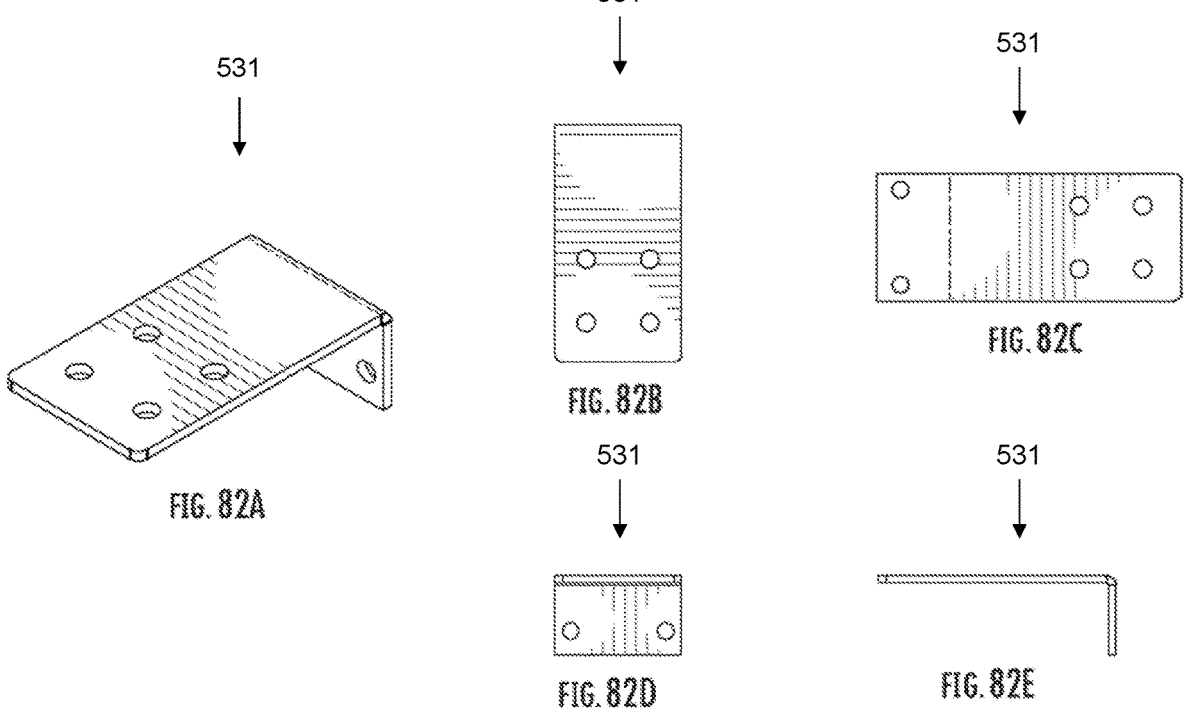

FIG. 82A illustrates a bulb mount.

FIG. 82B illustrates a bulb mount.

FIG. 82C illustrates a bulb mount.

FIG. 82D illustrates a bulb mount.

FIG. 82E illustrates a bulb mount.

Figures 83A, 83B, 83C:
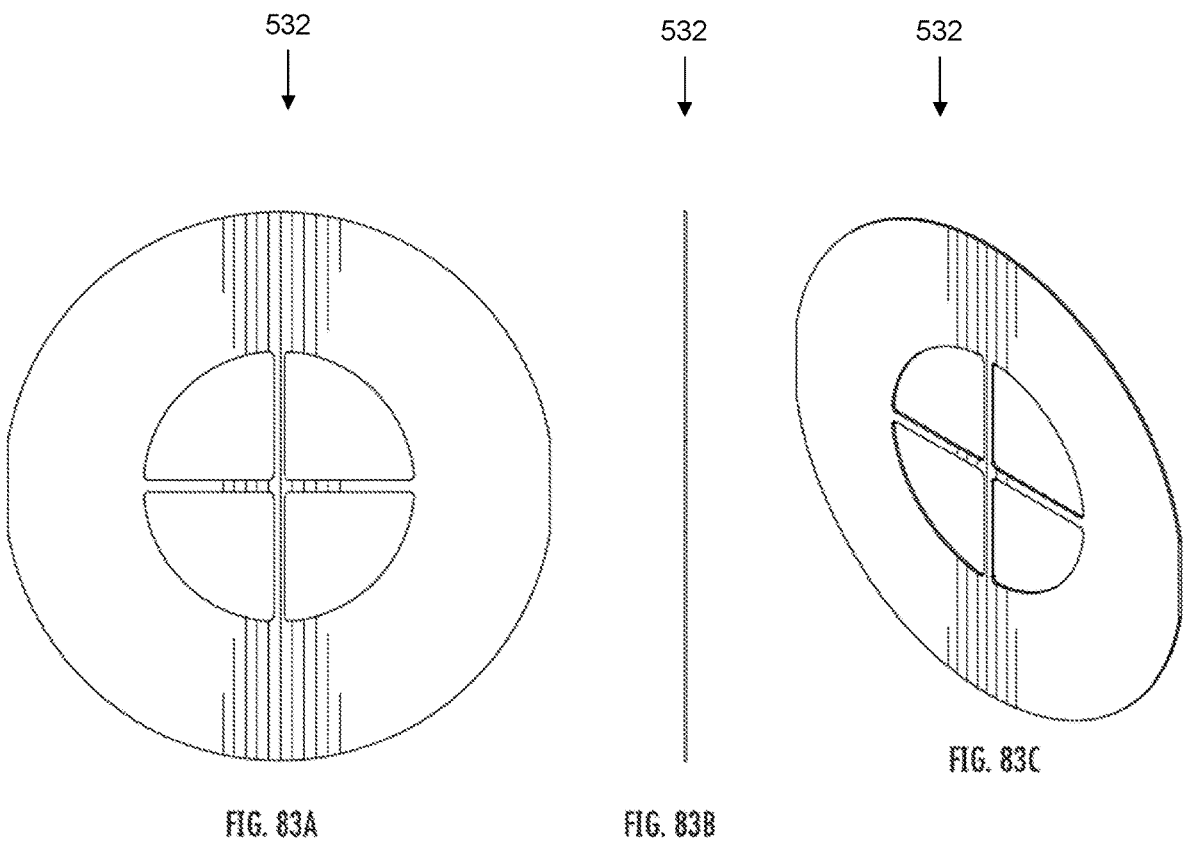

FIG. 83A illustrates an intake plate.

FIG. 83B illustrates an intake plate.

FIG. 83C illustrates an intake plate.

Figures 84A, 84B, 84C:
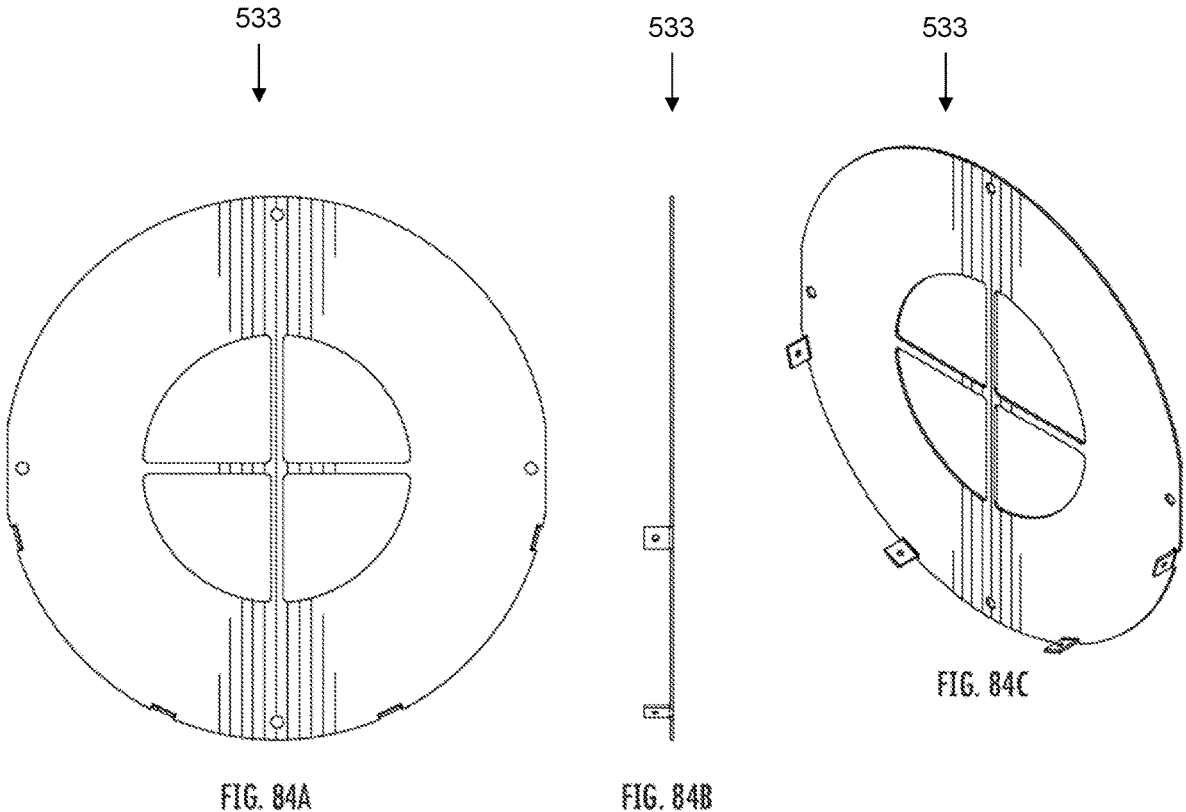

FIG. 84A illustrates an exhaust plate.

FIG. 84B illustrates an exhaust plate.

FIG. 84C illustrates an exhaust plate.

FIG. 85A illustrates a lock bracket.

FIG. 85B illustrates a lock bracket.

FIG. 85C illustrates a lock bracket.

FIG. 85D illustrates a lock bracket.

FIG. 85E illustrates a lock bracket.

Figures 86A, 86B, 86C:
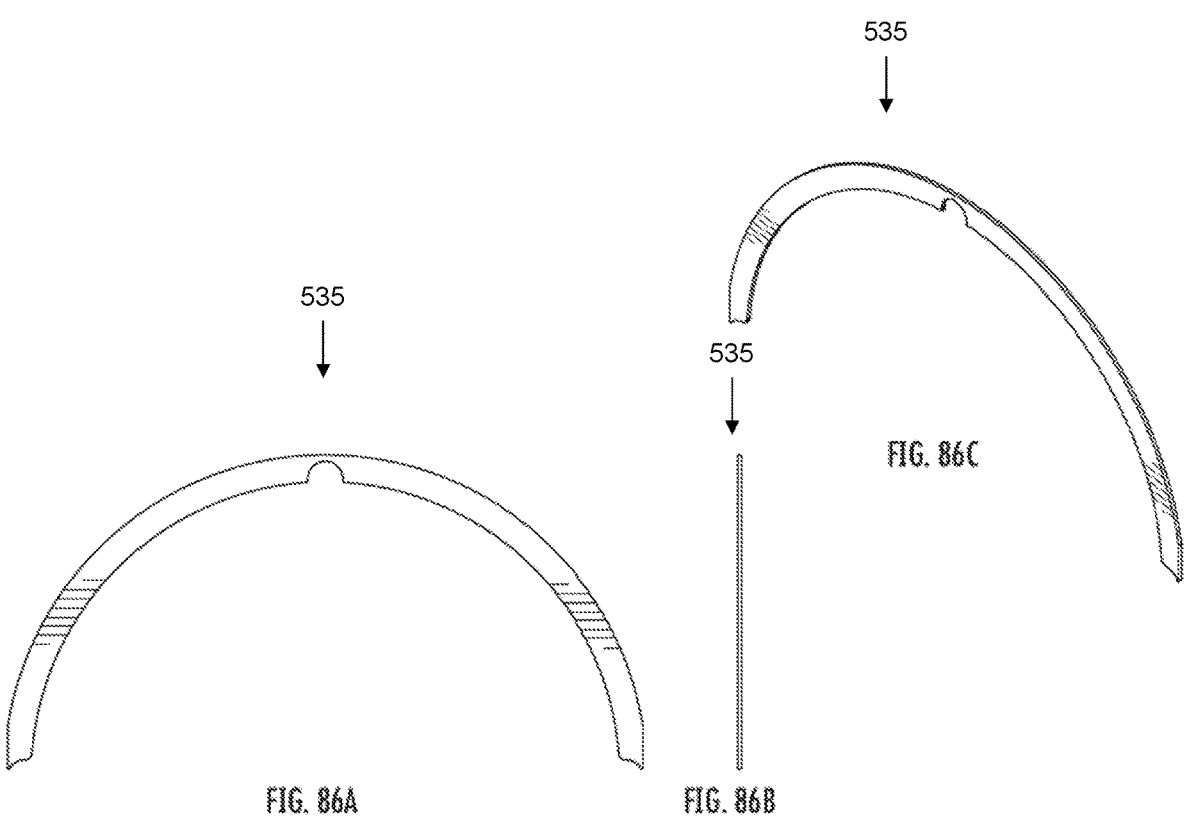

FIG. 86A illustrates a rib.

FIG. 86B illustrates a rib.

FIG. 86C illustrates a rib.

Figure 87:
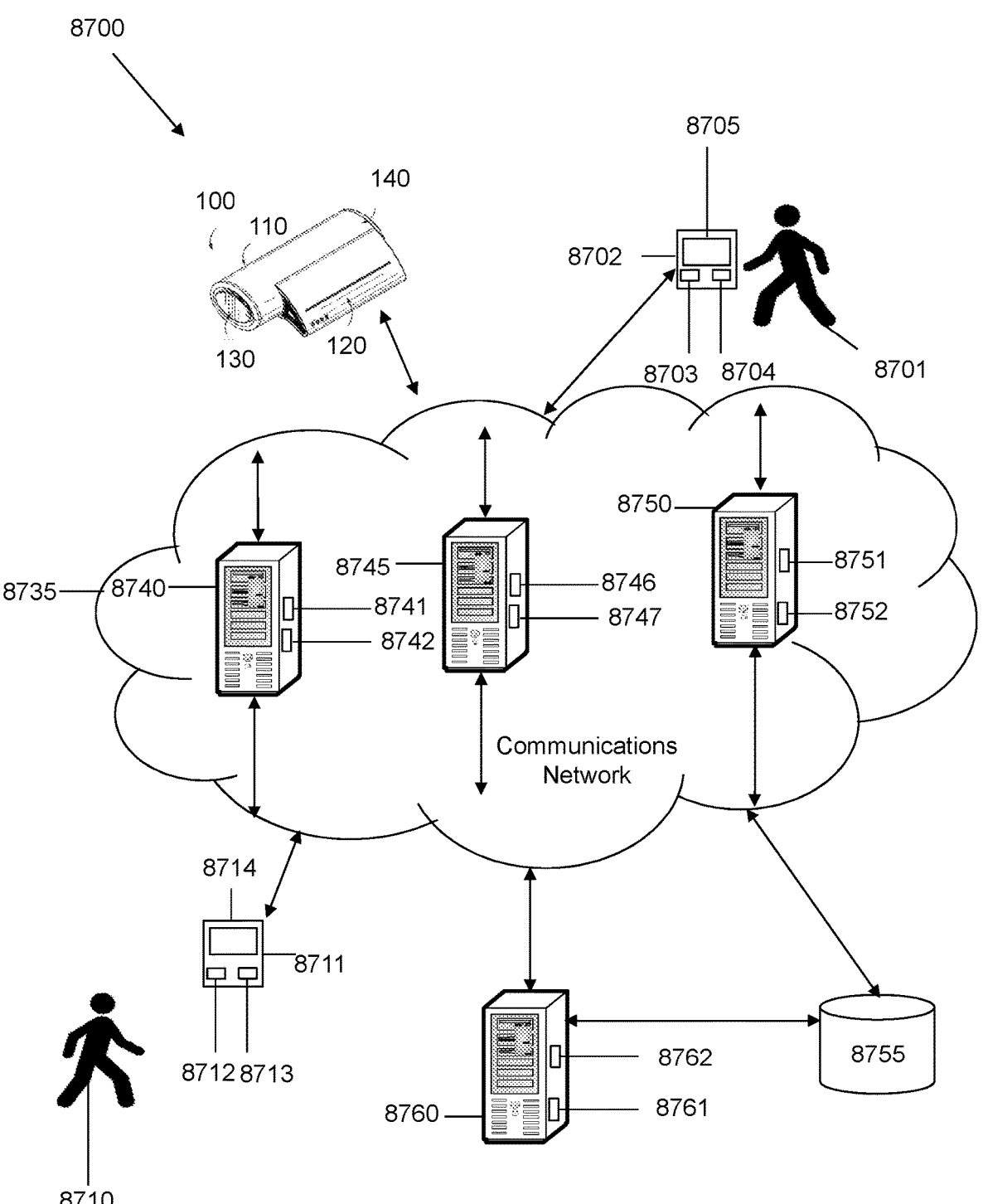

FIG. 87 illustrates a system for facilitating sanitization of air according to an embodiment of the present disclosure.

FIG. 88 illustrates a flow diagram illustrating a sample method for facilitating sanitization of air according to an embodiment of the present disclosure.

Figure 89:
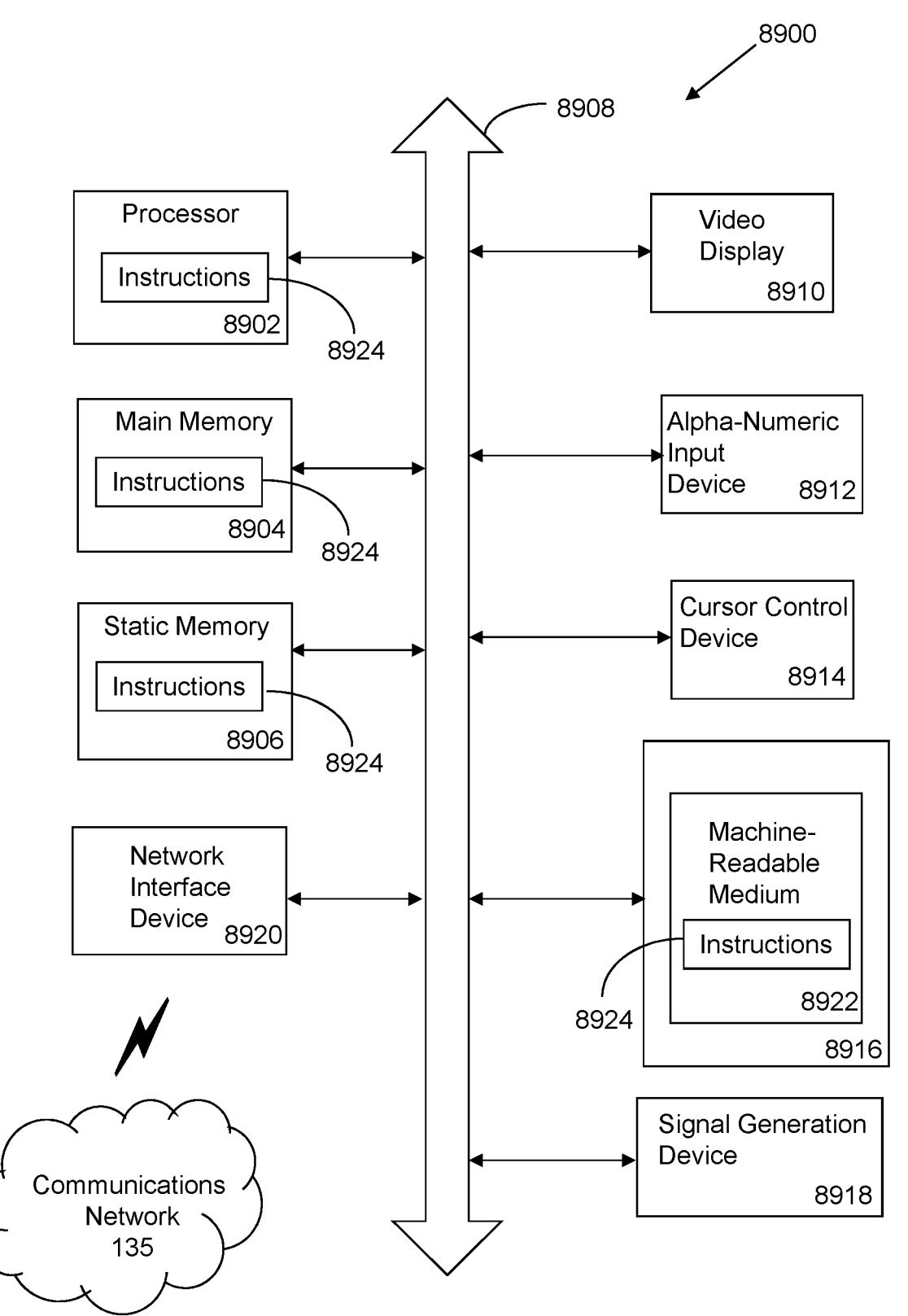

FIG. 89 is a schematic diagram of a machine in the form of a computer system within which a set of instructions, when executed, may cause the machine to facilitate sanitization of air according to embodiments of the present disclosure.

DETAILED DESCRIPTION OF THE INVENTION

A system (e.g. systems 100, 500) and method (e.g. method 8800) for sanitizing air in an environment is disclosed. In particular, systems and accompanying methods provide for an assembly to sanitize the air by utilizing UV light. As indoor air moves through an enclosed structure of the assembly, the air encounters a baffling assembly that may decrease pressure and cause air turbulence. As the air travels through the assembly, the air speed of the air may be reduced within the enclosed structure of the assembly. While in the assembly, the air may be exposed to UV light radiation at the electromagnetic spectrum ranges that are capable of causing biological atrophy and denaturation of contaminants. Exposure of the contaminants in the air to the UV light radiation may be maximized by the reduced air speed and turbulence facilitated by the assembly. As air is sanitized by the assembly, the sanitized air may be exhausted out of the assembly and into the environment. Based on at least the foregoing, individuals that enter the environment, such as after sanitization of the air, may be exposed to significantly fewer viruses, bacteria, pathogens, microorganisms, and/or other contaminants.

FIGS. 1-55 illustrate a system 100 in accordance with a first embodiment of the present disclosure. All measurements, dimensions, materials, and part numbers shown in the Figures are examples and are not intended to be limited to the specifications as described or illustrated. Notably, other measurements, dimensions, materials and part numbers may be used in accordance with the present disclosure.

As shown in FIGS. 1A, 1B, 1C, and 1D, the system 100 may include a body assembly 110 and a control assembly 120. In certain embodiments, the body assembly 110 may include a first end 130 and a second end 140. In certain embodiments, the body assembly 110 and the control assembly 120 may be coupled together to form the system 100 and may provide some or all of the operative functionality of the system 100.

Figure 2:
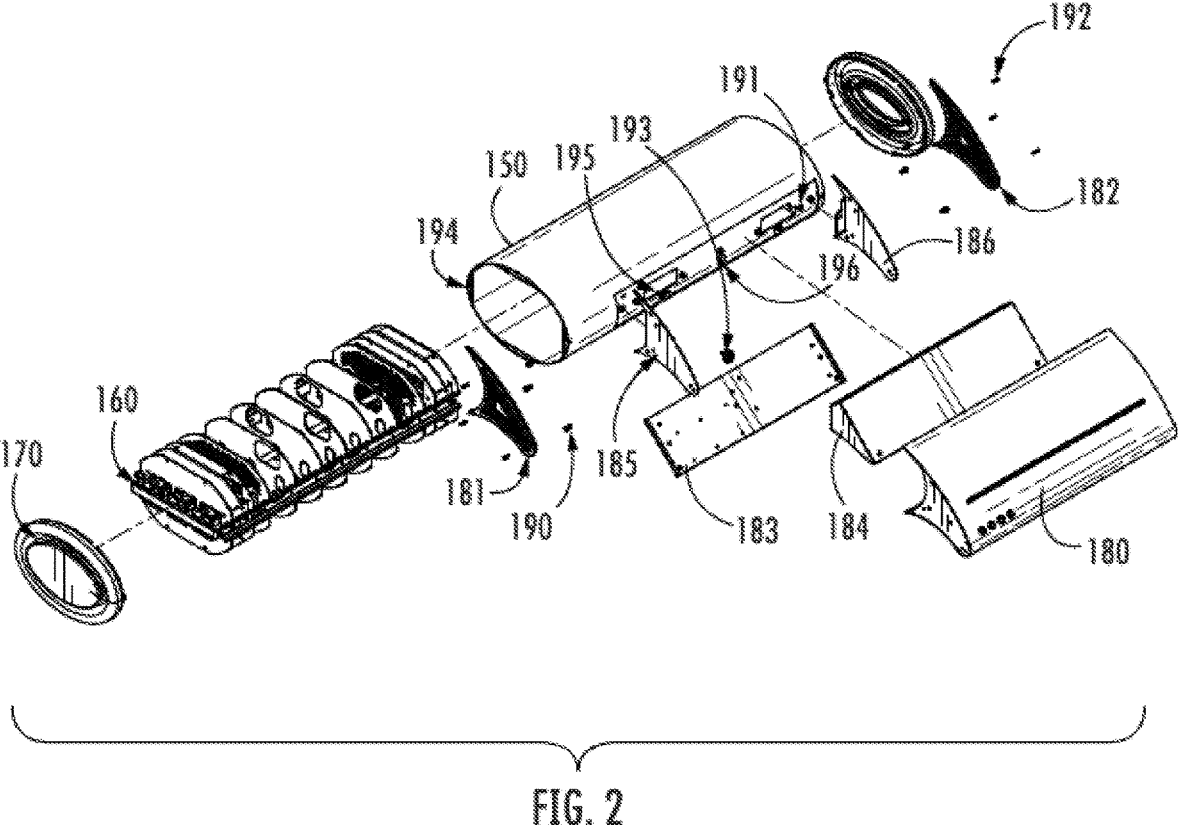
FIG. 2 illustrates the exploded view of the system 100.
Figures 3A, 3B, 3C, 3D, 3E:
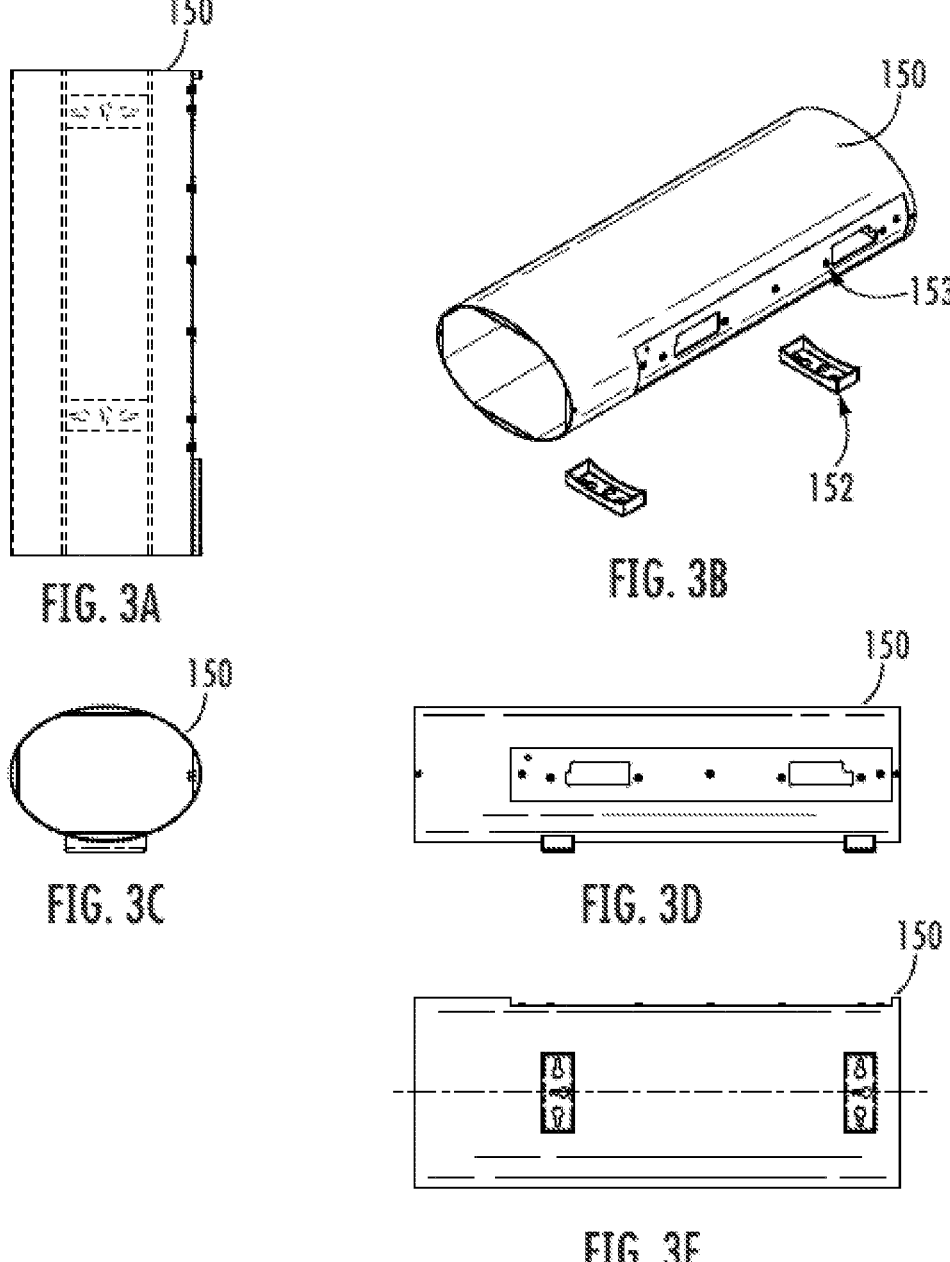
FIG. 3A illustrates the main body 150 and components of the system 100.
FIG. 3B illustrates an angled perspective view of the main body 150 of the system 100.
FIG. 3C illustrates an end view of the main body 150 of the system 100.
FIG. 3D illustrates a side view of the main body 150 of the system 100.
FIG. 3E illustrates a bottom view of the main body 150 of the system 100.
Figures 4A, 4B, 4C, 4D:
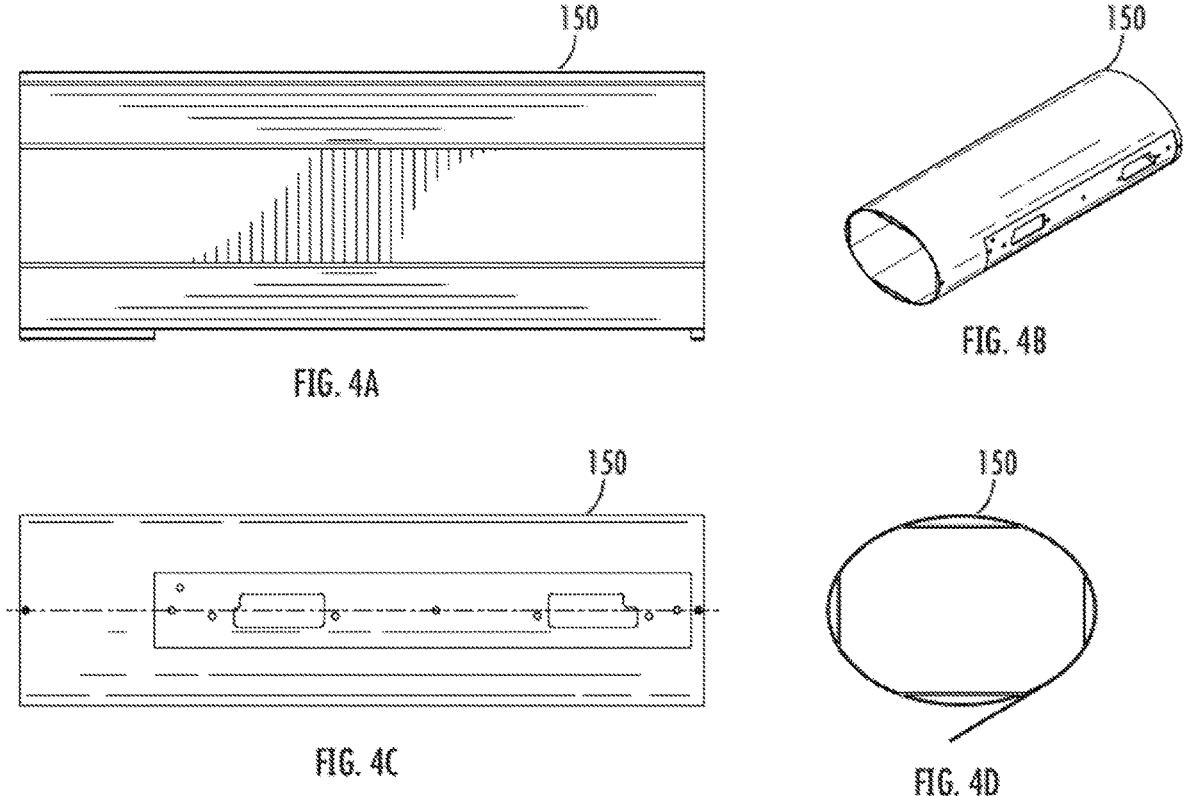
FIG. 4A illustrate the main body 150 and components of the system 100.
FIG. 4B illustrates an angled perspective view of the main body 150 of the system 100.
FIG. 4C illustrates a front view of the main body 150 of the system 100.
FIG. 4D illustrates an end view of the main body 150 of the system 100.
Figures 5A, 5B, 5C, 5D, 5E:
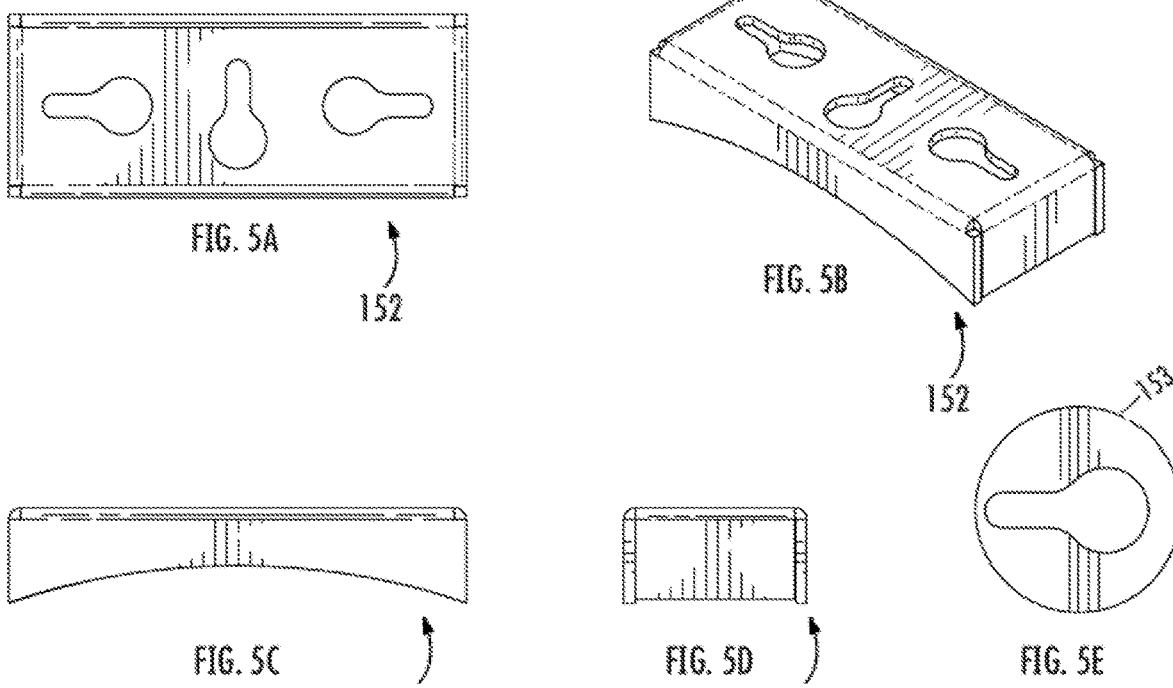
FIG. 5A illustrates a top view of a mounting plate of the system 100.
FIG. 5B illustrates an angled perspective view of the mounting plate of the system 100.
FIG. 5C illustrates a front view of the mounting plate of the system 100.
FIG. 5D illustrates an end view of the mounting plate of the system 100.
FIG. 5E illustrates fastener componentry of the system 100.

FIG. 2 illustrates an exploded view of the system 100, along with various internal components of the system 100. FIG. 2 illustrates a main body 150 of the body assembly 110, a baffle assembly 160, a main side cap 170, a control housing assembly 180, fasteners 190, a first control side cap 181, a second control side cap 182, an electronics panel assembly 183, a ballast bracket 184, fasteners 191, a first control rib 185, a second control rib 186, fasteners 192, fasteners 193, fasteners 194, fasteners, 195, and fasteners 196. As shown, the baffle assembly 160 may be designed to fit within the main body 150 of the system 100. The control housing assembly 180 may be designed to attach to the main body 150. FIGS. 3A-3E, 4A-4D, and 5A-5E illustrate the main body 150, mounting plate 152 and fasteners 153 that may be utilized with the system 100.

Figure 7:
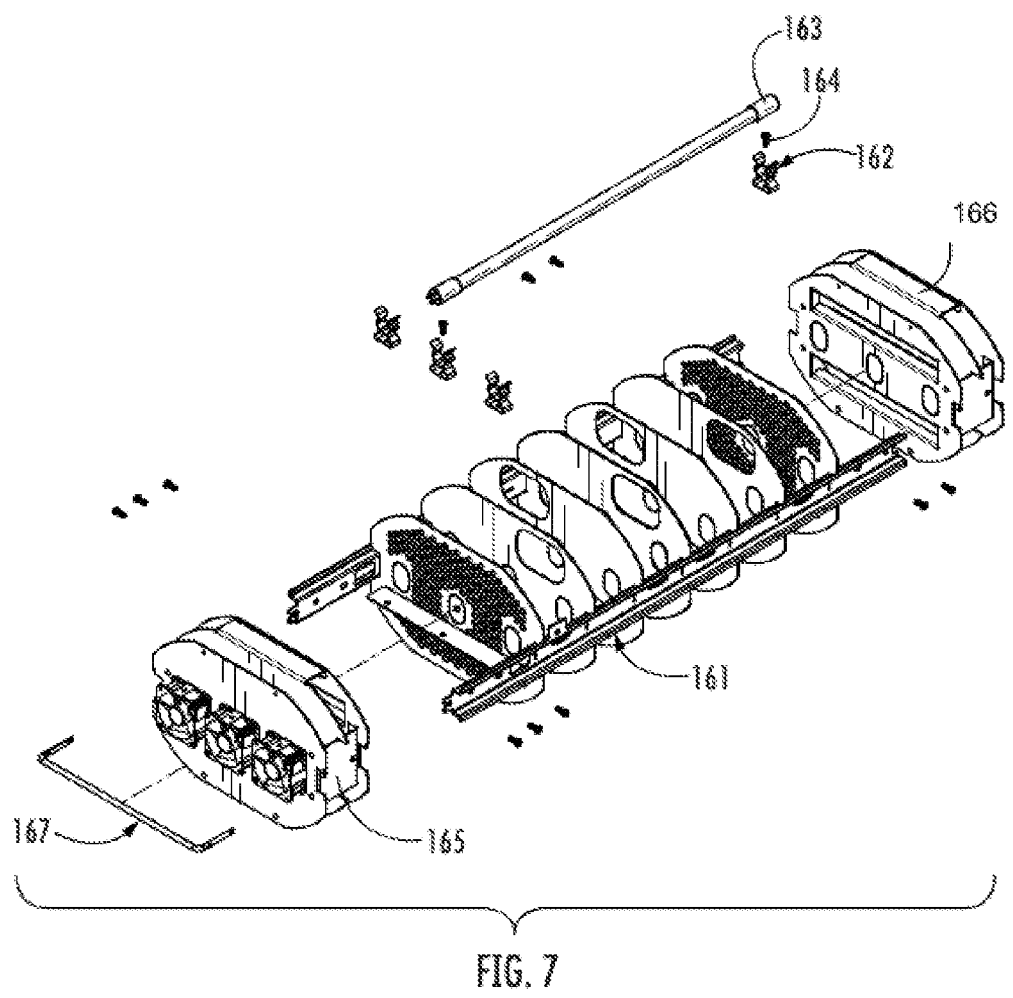
FIG. 7 illustrates an exploded view of the baffle assembly 160 of the system 100.
Figures 8A, 8B, 8C, 8D:
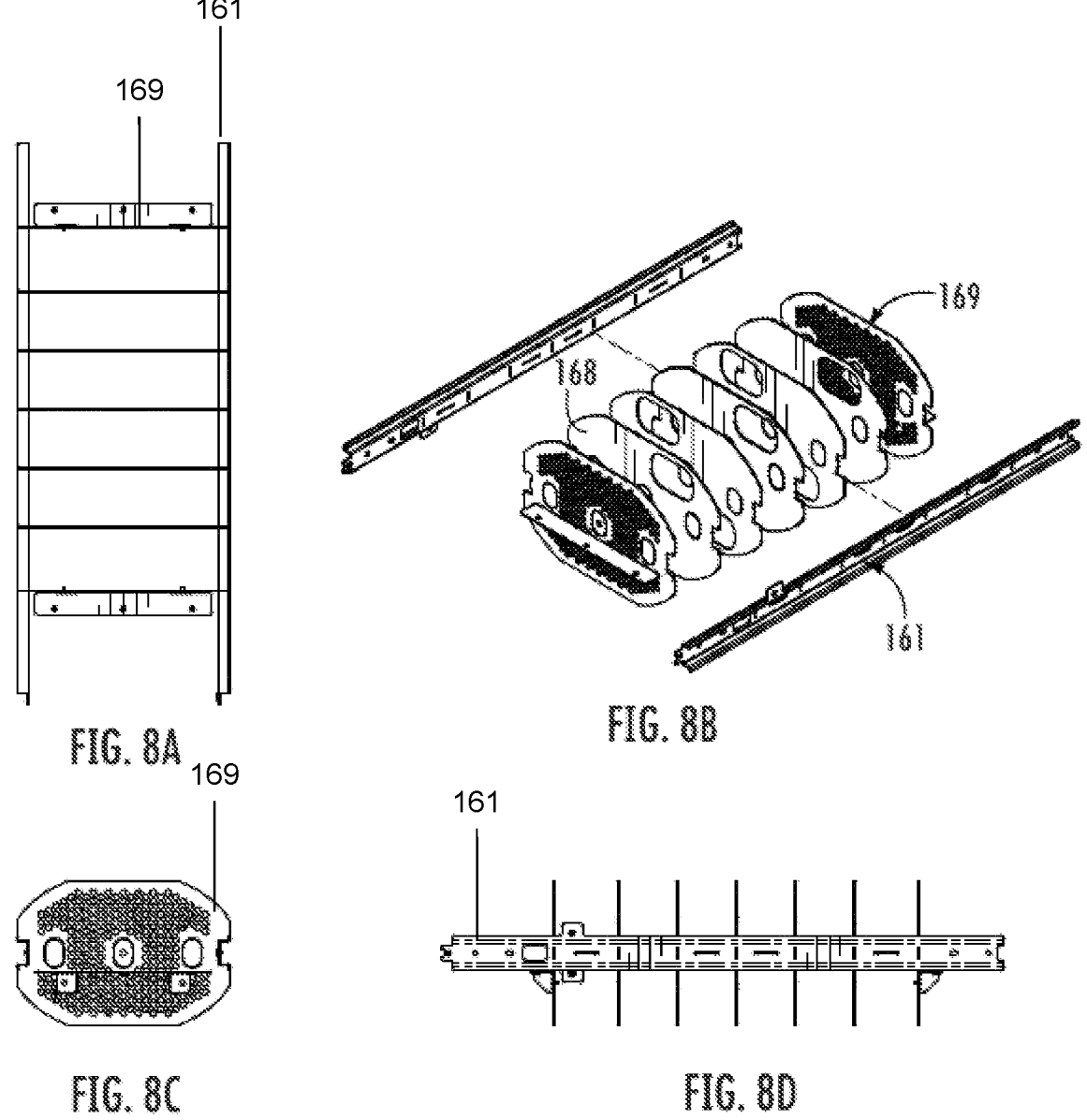
FIG. 8A illustrates components of the baffle assembly 160 of the system 100.
FIG. 8B illustrates components of the baffle assembly 160 of the system 100.
FIG. 8C illustrates components of the baffle assembly 160 of the system 100.
FIG. 8D illustrates components of the baffle assembly 160 of the system 100.
Figures 9A, 9B, 9C, 9D:
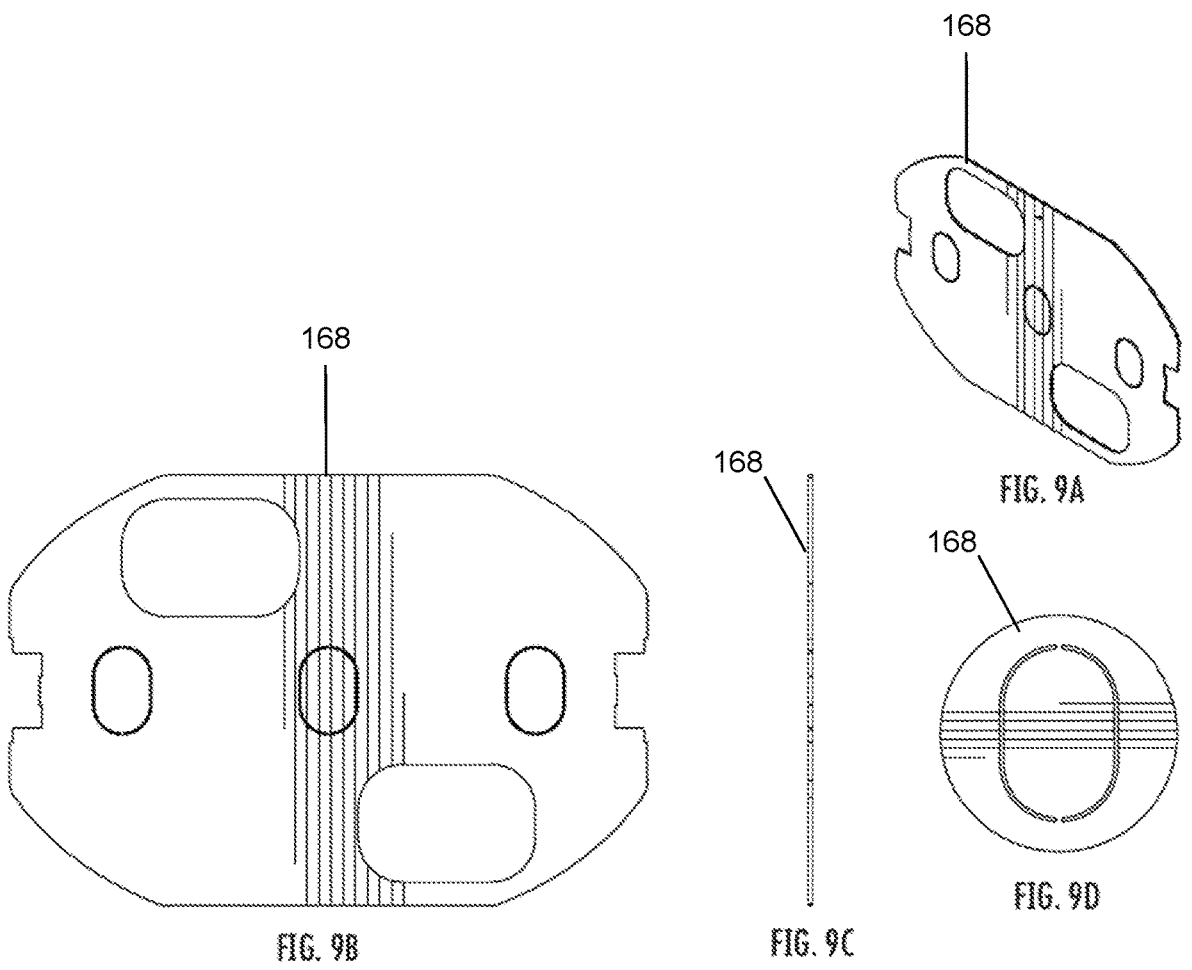
FIG. 9A illustrates an inner baffle plate 168 of the system 100.
FIG. 9B illustrates a front view of an inner baffle plate 168 of the system 100.
FIG. 9C illustrates a side view of an inner baffle plate 168 of the system 100.
FIG. 9D illustrates a portion of an inner baffle plate 168 of the system 100.
Figures 10A, 10B, 10C:
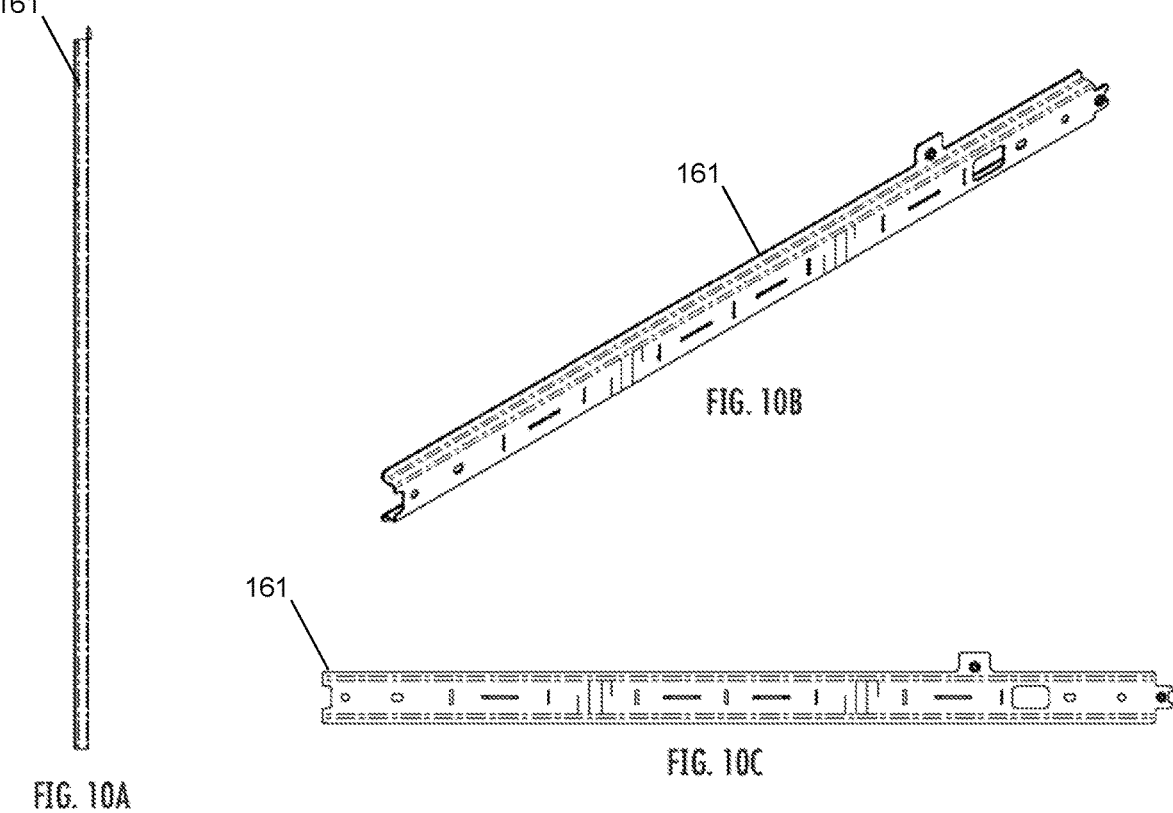
FIG. 10A illustrates a baffle bracket 161 of the system 100.
FIG. 10B illustrates an angled perspective view of a baffle bracket 161 of the system 100.
FIG. 10C illustrates a front view of a baffle bracket 161 of the system 100.
Figures 11A, 11B, 11C, 11D, 11E, 11F:
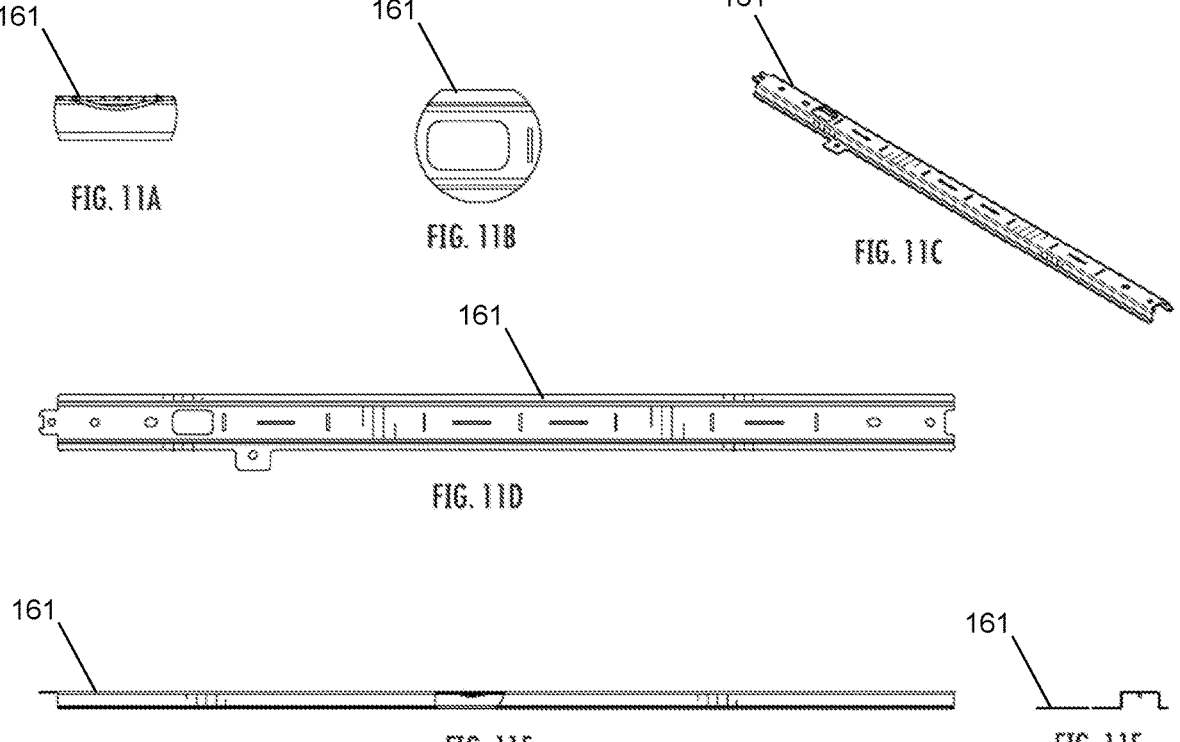
FIG. 11A illustrates a view of a baffle bracket 161 of the system 100.
FIG. 11B illustrates a view of a portion of a baffle bracket 161 of the system 100.
FIG. 11C illustrates an angled perspective view of a baffle bracket 161 of the system 100.
FIG. 11D illustrates a top view of a baffle bracket 161 of the system 100.
FIG. 11E illustrates a side view of a baffle bracket 161 of the system 100.
FIG. 11F illustrates a view of a portion of a baffle bracket 161 of the system 100.
Figures 13A, 13B, 13C, 13D, 13E:
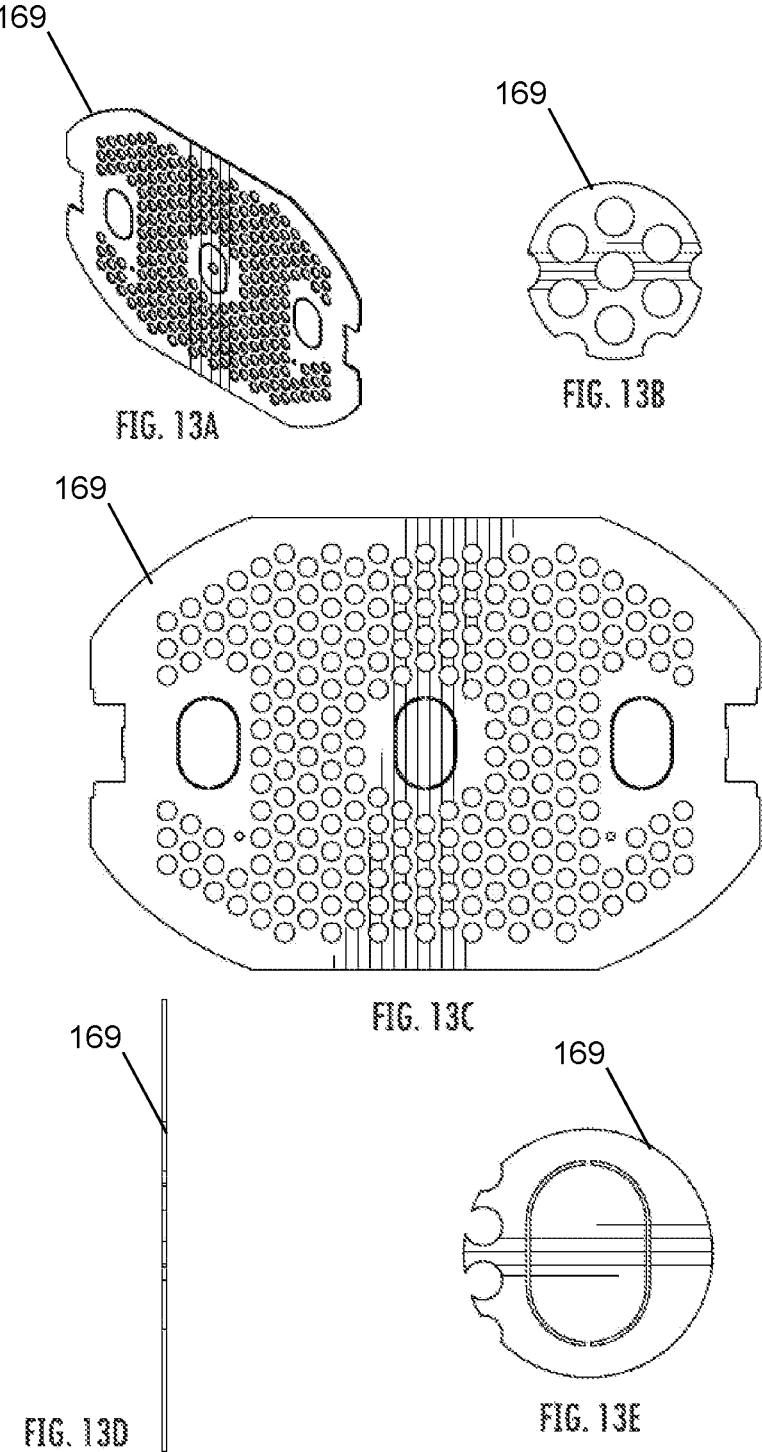
FIG. 13A illustrates an angled perspective view of an end baffle plate 169 of the system 100.
FIG. 13B illustrates a portion of an end baffle plate 169 of the system 100.
FIG. 13C illustrates a front view of an end baffle plate 169 of the system 100.
FIG. 13D illustrates a side view of an end baffle plate 169 of the system 100.
FIG. 13E illustrates a view of a portion of an end baffle plate 169 of the system 100.
Figures 15A, 15B, 15C, 15D:
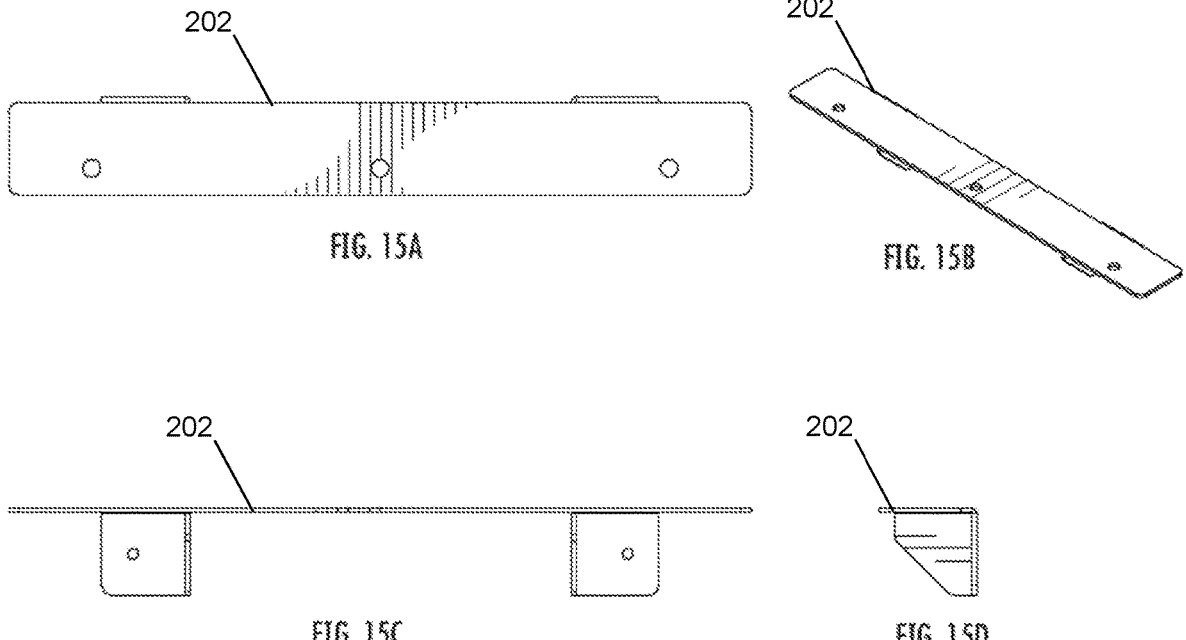
FIG. 15A illustrates a top view of the bulb mount bracketing for the lighting tubes to be held within the baffle assembly 160 of the system 100.
FIG. 15B illustrates an angled perspective view of the bulb mount bracketing for the lighting tubes to be held within the baffle assembly 160 of the system 100.
FIG. 15C illustrates a front view of the bulb mount bracketing for the lighting tubes to be held within the baffle assembly 160 of the system 100.
FIG. 15D illustrates a side view of the bulb mount bracketing for the lighting tubes to be held within the baffle assembly 160 of the system 100.
Figures 16A, 16B, 16C, 16D:
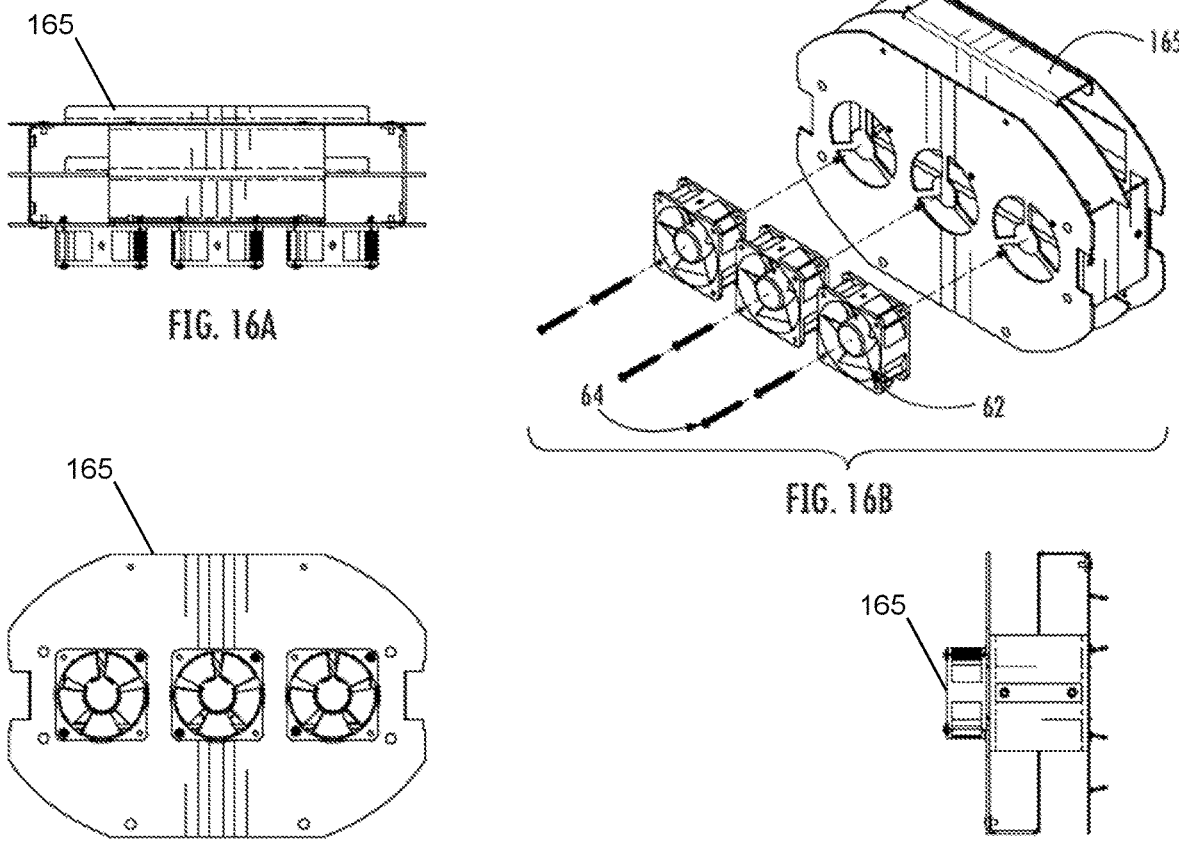
FIG. 16A illustrates the front fan assembly 165 of the system 100.
FIG. 16B illustrates an angled perspective view of the front fan assembly 165 of the system 100.
FIG. 16C illustrates a front view of the front fan assembly 165 of the system 100.
FIG. 16D illustrates a side view of the front fan assembly 165 of the system 100.

FIGS. 6A-6D, 7, 8A-8D, 9A-9D, 10A-10C, 11A-11F, 12A-12D, 13A-13E, 14A-14D, and 15A-15D illustrate the baffle assembly 160 and certain related components. As shown in FIG. 7, baffle assembly 160 includes baffle brackets 161, bulb clips 162, UV bulb 163, fastener 164, front fan assembly 165, rear fan assembly 166, and handle 167. As shown in FIGS. 8A-8D, baffle assembly 160 includes inner baffle plates 168 and end baffle plates 169. FIGS. 9A-9D illustrate inner baffle plates 168 and FIGS. 12A-12D and 13A-13E illustrate end baffle plates 169. FIGS. 10A-10C and 11A-11F illustrate baffle brackets 161. FIGS. 14A-14D and 15A-15D illustrates bulb mount brackets.

FIGS. 16A-16D, 17A-17D, 18A-18D, 19A-19D, 20A-20D, 21A-21E, 22A-22D, 23A-23D illustrate front fan assembly 165 and various components of the front fan assembly 165. The front fan assembly 165 may be utilized to draw air into the system 100 and direct the air to the baffle assembly 160. Front fan assembly 165 includes fans 62 and fasteners 64. Front fan assembly 165 may also include front fan mount 61, bracket 63, front fan mid-baffle 65, front fan internal baffle 66, and fasteners 67. FIGS. 18A-18D and 19A-19D illustrate various views of the front fan mount 61 of the front fan assembly 165. FIGS. 20A-20D illustrates the front fan mid-baffle 65 of the front fan assembly 165 in further detail. FIGS. 21A-21E illustrates the front fan internal baffle 66 of the front fan assembly 165 in further detail. FIGS. 22A-22D and 23A-23D illustrate bracket 63 of the front fan assembly 165.

Figures 26A, 26B, 26C, 26D:
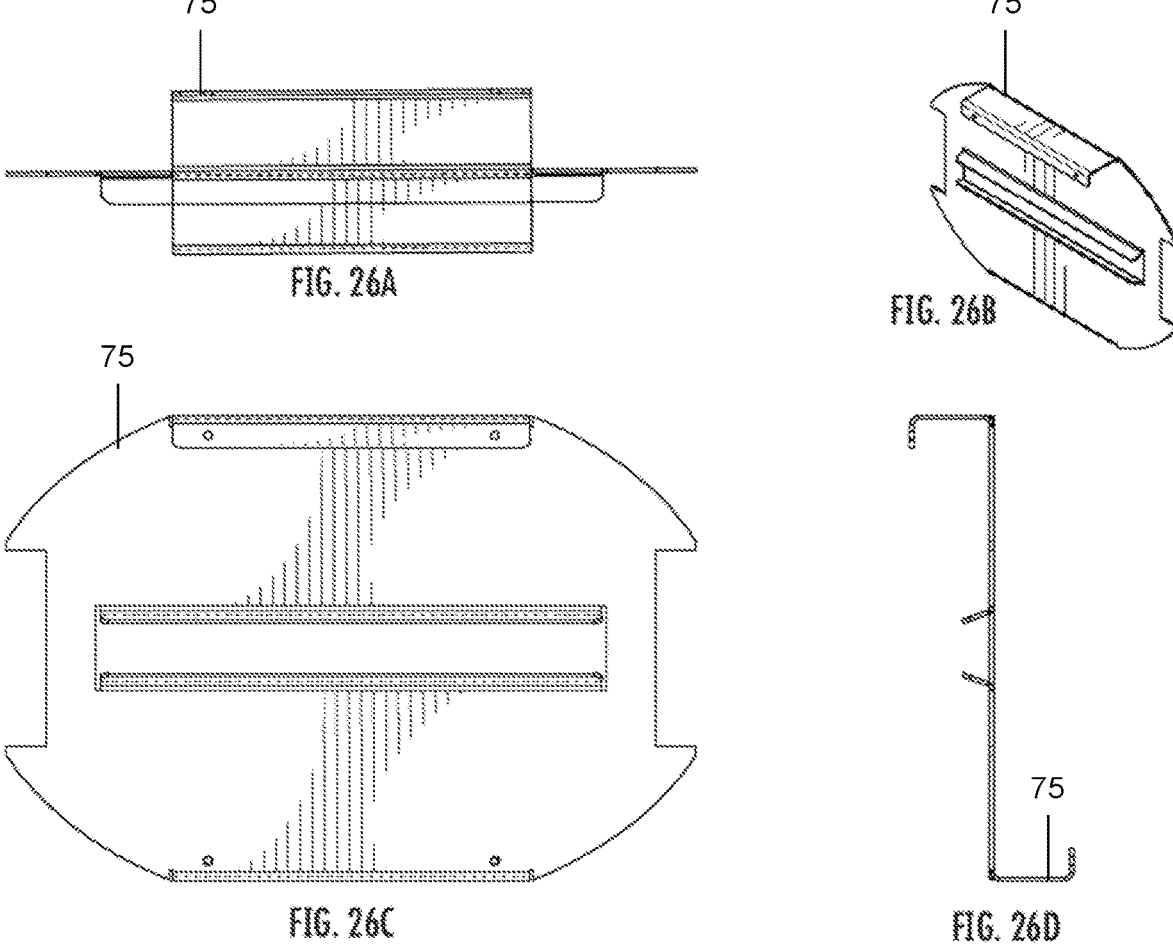
FIG. 26A illustrates a top view of the rear fan mid-baffle 75 of the system 100.
FIG. 26B illustrates an angled perspective view of the rear fan mid-baffle 75 of the system 100.
FIG. 26C illustrates a front view of the rear fan mid-baffle 75 of the system 100.
FIG. 26D illustrates a side view of the rear fan mid-baffle 75 of the system 100.
Figures 27A, 27B, 27C, 27D, 27E:
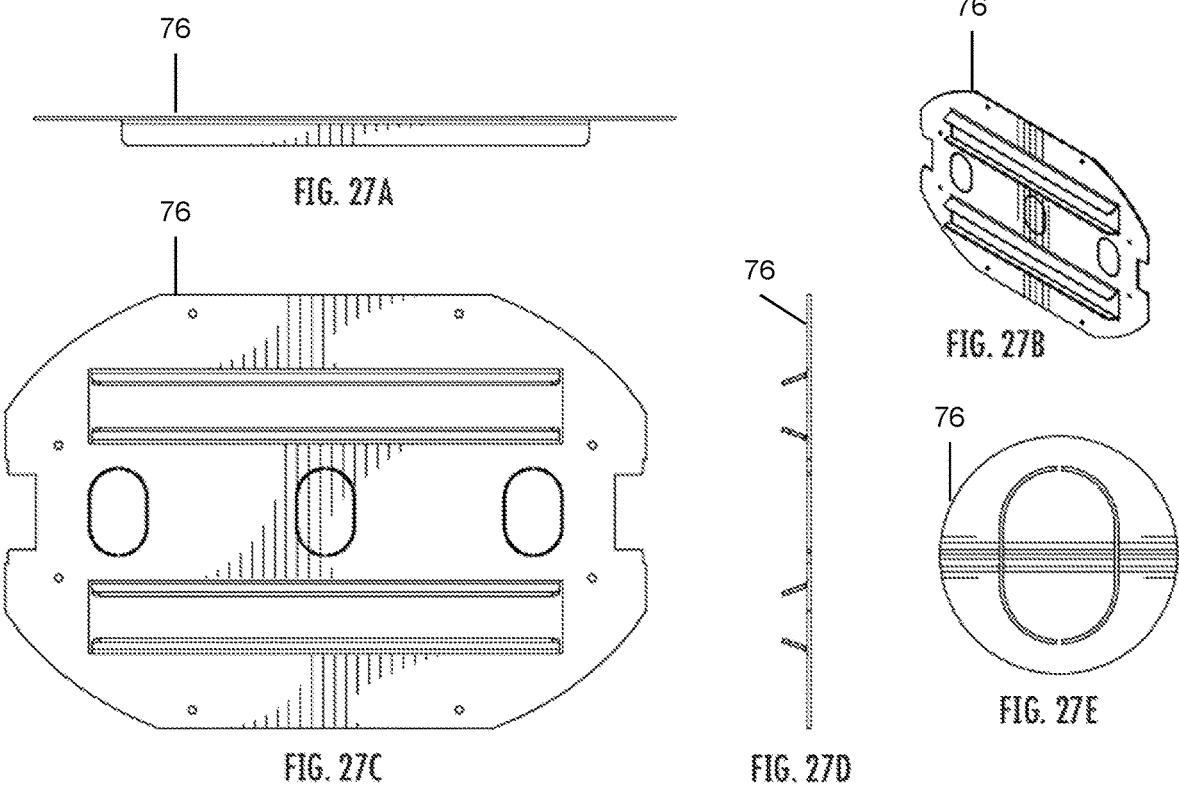
FIG. 27A illustrates a top view of the rear fan internal baffle 76 of the system 100.
FIG. 27B illustrates a an angled perspective view of the rear fan internal baffle 76 of the system 100.
FIG. 27C illustrates a front view of the rear fan internal baffle 76 of the system 100.
FIG. 27D illustrates a side view of the rear fan internal baffle 76 of the system 100.
FIG. 27E illustrates a portion of the rear fan internal baffle 76 of the system 100.
Figure 28B:
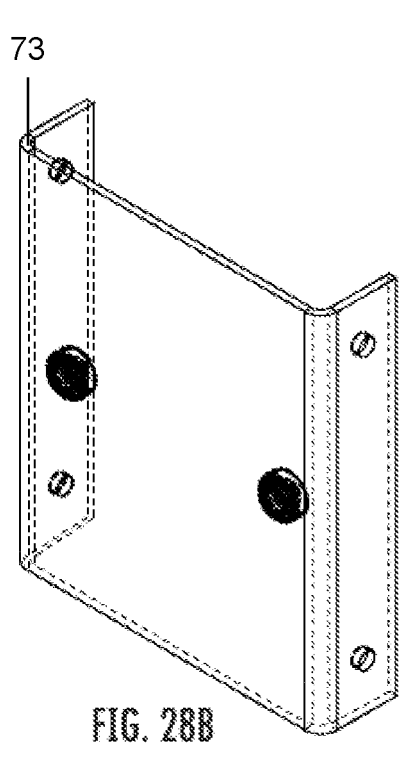
FIG. 28B illustrates an angled perspective view of the rear fan bracket 73 of the system 100.
Figure 28A:
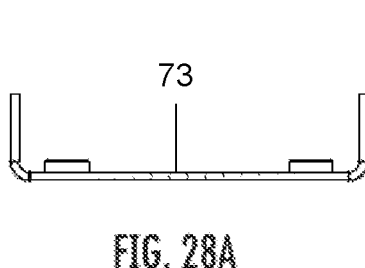
FIG. 28A illustrates a top view of the rear fan bracket 73 of the system 100.
Figure 28C:
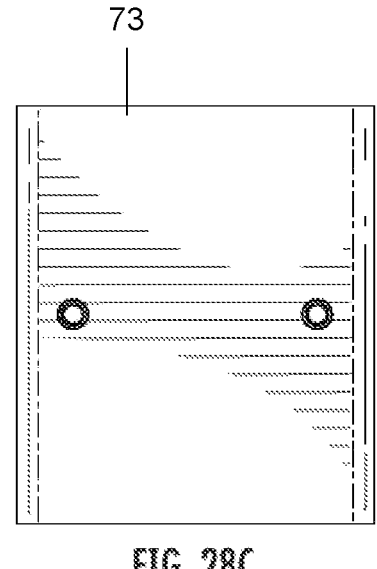
FIG. 28C illustrates a front view of the rear fan bracket 73 of the system 100.
Figure 28D:
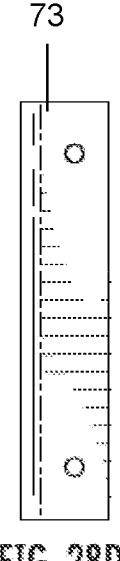
FIG. 28D illustrates a side view of the rear fan bracket 73 of the system 100.
Figure 30A:
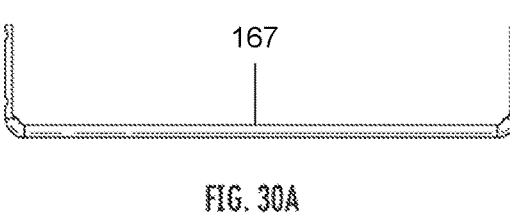
FIG. 30A illustrates a top view of the handle 167 of the system 100.
Figure 30B:
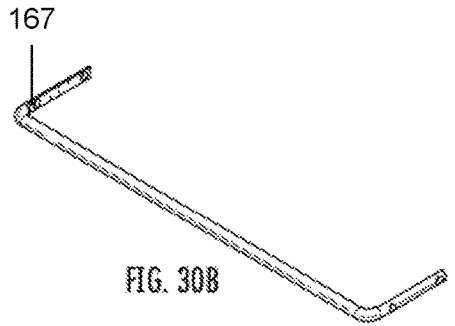
FIG. 30B illustrates an angled perspective view of the handle 167 of the system 100.
Figure 30C:
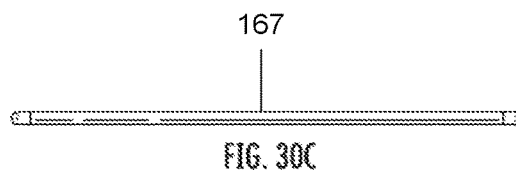
FIG. 30C illustrates a front view of the handle 167 of the system 100.
Figure 30D:
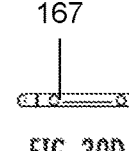
Figure 31A:
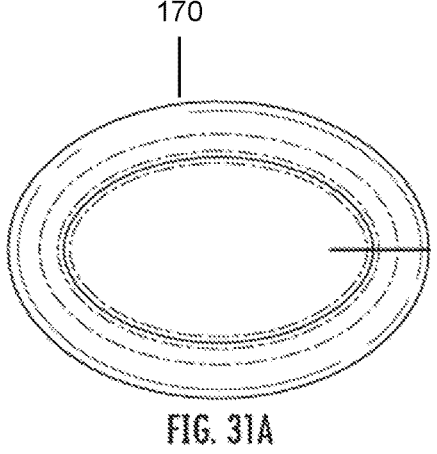
Figure 31B:
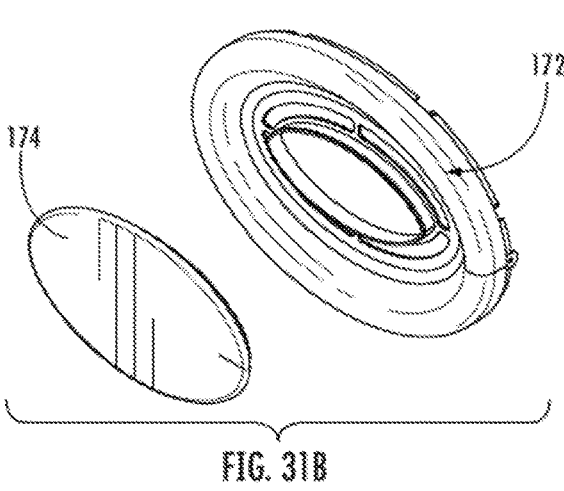
Figure 31C:
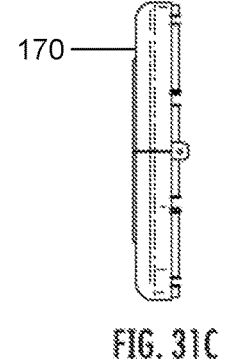
Figure 31D:
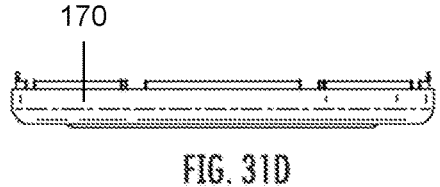
Figures 32A, 32B, 32C, 32D, 32E:
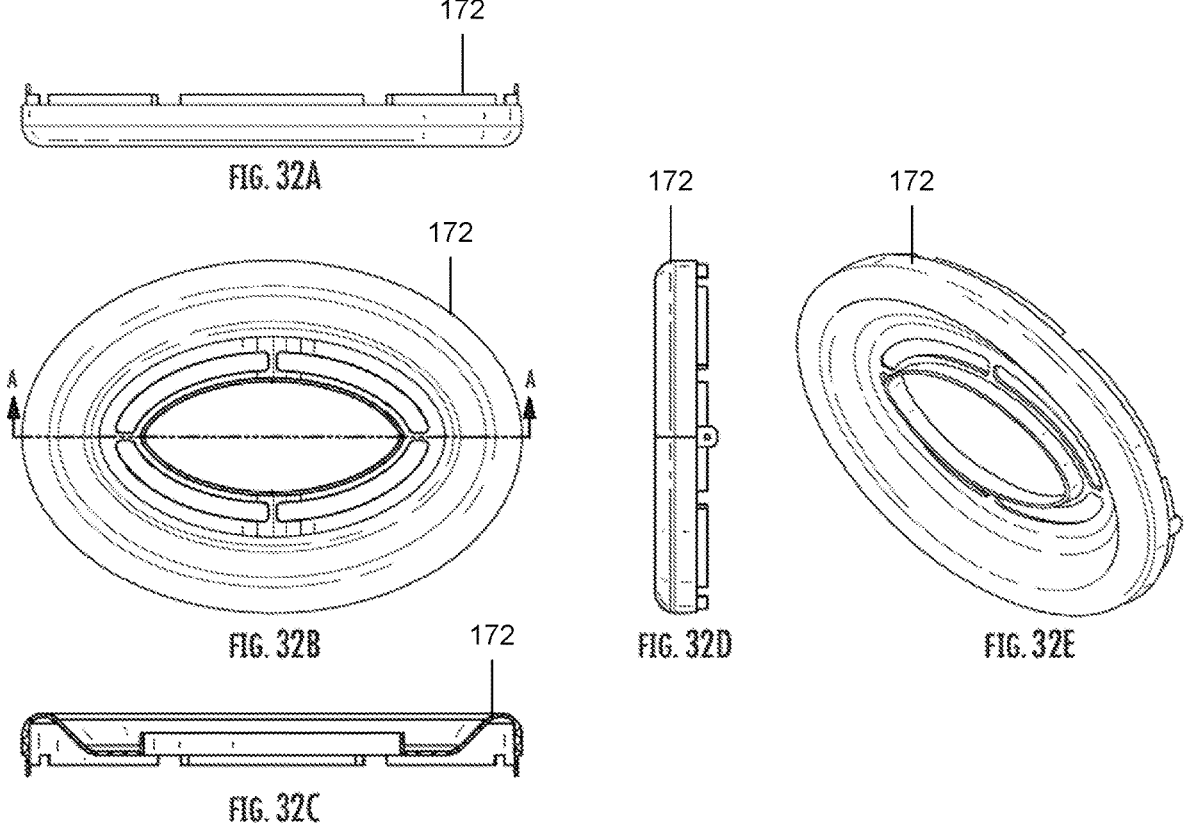

FIGS. 24A-24D, 25A-25D, 26A-26D, 27A-27E, 28A-28D, and 29A-20D illustrate rear fan assembly 166. The rear fan assembly 166 may be utilized to exhaust sanitized air out from the system 100. Rear fan assembly 166 includes fan 72 and fasteners 74. Rear fan assembly 166 also may include rear fan mount 71, bracket 73, rear fan mid-baffle 75, rear fan internal baffle 76, and fasteners 77. FIG. 26 illustrates the rear fan mid-baffle 75. FIG. 27 illustrates the rear fan internal baffle 76. FIGS. 28 and 29 illustrate bracket 73, which may be utilized to secure rear fan mid-baffle 75, rear fan internal baffle 76, and other components of the rear fan assembly 166 together.

FIGS. 30A-30D illustrate handle 167. FIGS. 31A-31D illustrate main side cap 170 of the system 100. In certain embodiments, the main side cap 170 may include a side cap bottom 172 and side cap top 174. FIGS. 32A-32E illustrate the side cap bottom 172 and FIGS. 33A-33E illustrate the side cap top 174.

FIGS. 34A-34C, 35A-35G, 36A-36C, 37A-37C, 38A-38D, 39A-39C, 40A-40D, 41A-41C, 42A-42D, 43A-43E, 44A-44C, 45A-45C illustrate the control housing assembly 180 and select components. As shown in FIGS. 34A-34C, control housing assembly 180 may include a pushbutton placeholder 81, front housing 82, led lens 83, led housing 84, grommet 85, locknut 86, led 87, and cable holders 88. FIGS. 35A-35G illustrate housing 82, first control rib 185, second control rib 186, and fastener 89. FIGS. 36A-36C and 37A-37C illustrate housing 82. FIGS. 38A-38D and 39A-39C illustrate the first control side cap 181. FIGS. 40A-40D and 41A-41C illustrate the second control side cap 182. FIGS. 42A-42D illustrate the led lens 83. FIGS. 43A-43E illustrate the led housing 84. FIGS. 44A-44C illustrate the first control side cap 181. FIGS. 45A-45C illustrates the second control side cap 182.

FIGS. 46A-46D illustrate the electronics panel assembly 183. The electronics panel assembly 183 may include a sub panel 91, controller board 92, ballast 93, and fasteners 94. In an embodiment, the electronics panel assembly 183 may be configured to connect to a network (e.g. communications network 8735 in FIG. 87), for example, a cellular or wi-fi network. The electronics panel assembly 183 may be configured to monitor the operation of the system 100. In certain embodiments, the status of system 100 may be communicated via a network connection to a remote system. For example, parameters such as, but not limited to, fan speed, maintenance issues, bulb life, air velocity, types of detected pathogens, viruses, bacteria, and/or other parameters of system 100 may be communicated to a remote system via a network. The controller board 92, in certain embodiments, may include processors, memories, transceivers, communication modules, sensors, any type of monitoring device, or a combination thereof. In certain embodiments, the sensors may include, but are not limited to, cameras, motion sensors, acoustic/audio sensors, sensors for detecting viruses, bacteria, pathogens, and/or organisms, pressure sensors, temperature sensors, light sensors, heart-rate sensors, humidity sensors, any type of sensors, or a combination thereof. The sensors may be utilized to monitor the operation of the system 100 and the air purification process. In certain embodiments, the sensors may monitor the components of the system 100 for potential failures, overuse, and/or other selected conditions. In an embodiment, a user may control parameters of system 100 via a network through a remote computer terminal and/or telephone application, which may be local and/or remote with respect to the system 100. The system 100 may also send maintenance requests to a local and/or remote terminal via a network. FIGS. 47A-47D and 48A-48D illustrates sub panel 91. FIGS. 49A-49D illustrate the ballast bracket 95, ballast rail 96, and ballast gusset 97. FIGS. 50A-50D illustrate the ballast bracket 95. FIGS. 51A-51E illustrate the ballast bracket. FIGS. 52A-52D illustrate the ballast rail. FIGS. 53A-53C illustrates the ballast gusset. FIGS. 54A-54C illustrate the first control rib 185. FIGS. 55A-55C illustrate the second control rib 186.

In operation of the first embodiment, air is taken into the system 100 through the main side cap 170 on the body assembly first end 130, passes through the baffle assembly 160, and exhausted out of the body assembly second end 140. In certain embodiments, air may be taken into the system 100 through the body assembly second end 140 and exhausted from the main side cap 170 on the body assembly first end 130.

Figures 17A, 17B, 17C, 17D:
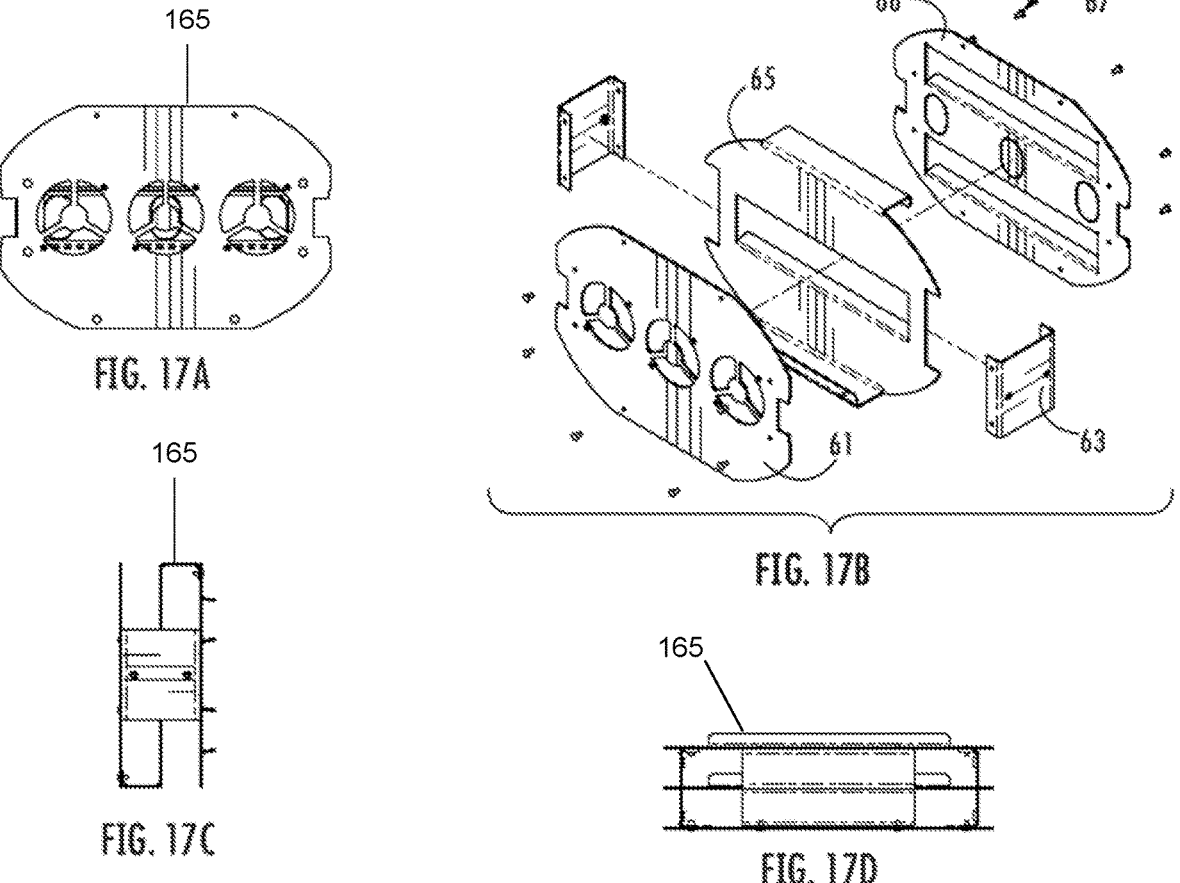
FIG. 17A illustrates a front view of components of the front fan assembly 165 of the system 100.
FIG. 17B illustrates an angled perspective view of components of the front fan assembly 165 of the system 100.
FIG. 17C illustrates a side view of components of the front fan assembly 165 of the system 100.
FIG. 17D illustrates a top view of components of the front fan assembly 165 of the system 100.
Figures 18A, 18B, 18C, 18D:
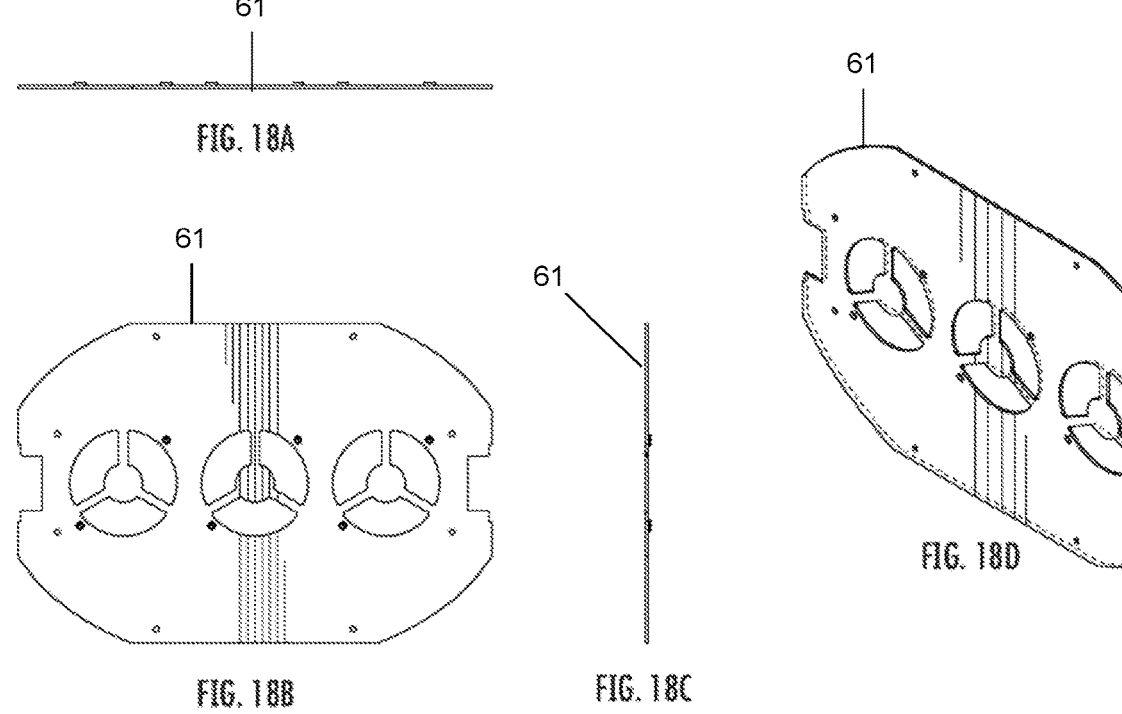
FIG. 18A illustrates a top view of components of the front fan assembly 165 of the system 100.
FIG. 18B illustrates a front view of components of the front fan assembly 165 of the system 100.
FIG. 18C illustrates a side view of components of the front fan assembly 165 of the system 100.
FIG. 18D illustrates an angled perspective view of components of the front fan assembly 165 of the system 100.
Figures 19A, 19B, 19C, 19D:
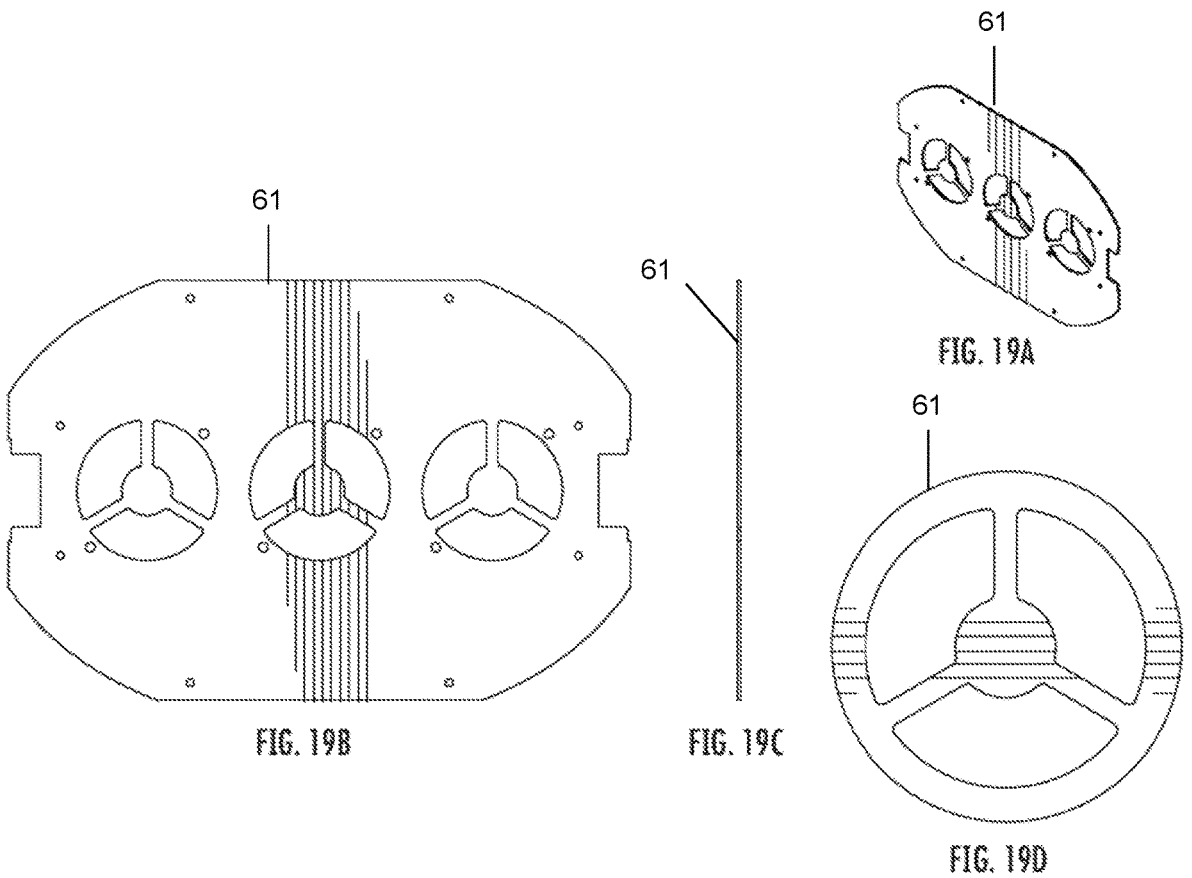
FIG. 19A illustrates an angled perspective view of components of the front fan assembly 165 of the system 100.
FIG. 19B illustrates a front view of components of the front fan assembly 165 of the system 100.
FIG. 19C illustrates a side view of components of the front fan assembly 165 of the system 100.
FIG. 19D illustrates a view of a portion of components of the front fan assembly 165 of the system 100.

As air intake through the main side cap 170 on the body assembly first end 130, air encounters the front fan assembly 165. The front fan assembly 165 has one or more fans 62 that draw air into the system 100 and create airflow. The fans 62 are mounted to a fan mount 61. In an embodiment, the fans 62 may be of different sizes to create uneven airflow into system 100. In certain embodiments, the fans 62 may be of the same size and flow rating. As air passes through fans 62 and fan mount 61, the air encounters the fan mid-baffle 65 and fan internal baffle 66. As shown in FIG. 17B, fan mid-baffle 65 has two flanges used to connect with the fan mount 61 and fan internal baffle 66. One flange extends from the bottom of the fan mid-baffle 65 toward the fan mount 61. A second flange extends from the top of the fan mid-baffle 65 to the fan internal baffle 67. The flanges create a gap space between the fan mount 61, fan mid-baffle 65, and fan internal baffle 66, to allow for airflow.

Figures 21A, 21B, 21C, 21D, 21E:
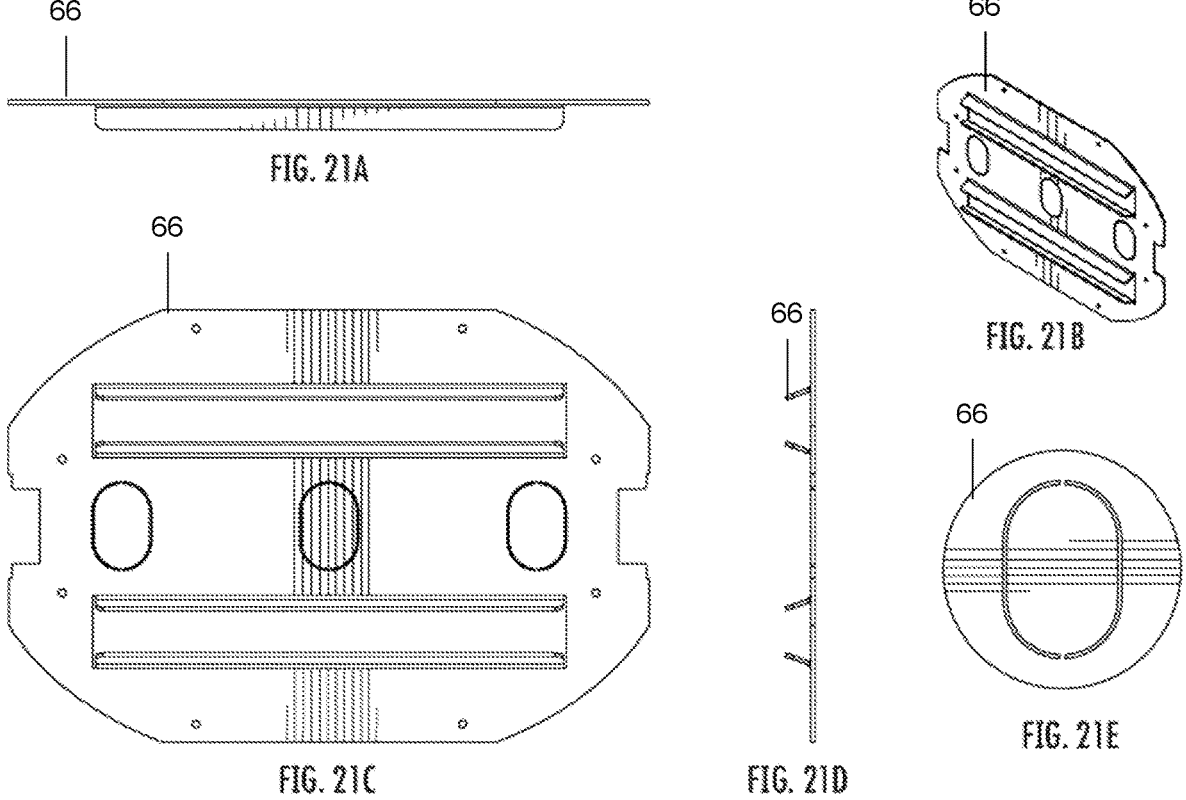
FIG. 21A illustrates a top view of the front fan internal baffle 66 of the system 100.
FIG. 21B illustrates an angled perspective view of the front fan internal baffle 66 of the system 100.
FIG. 21C illustrates a front view of the front fan internal baffle 66 of the system 100.
FIG. 21D illustrates a side view of the front fan internal baffle 66 of the system 100.
FIG. 21E illustrates a view of a portion of the front fan internal baffle 66 of the system 100.
Figure 22B:
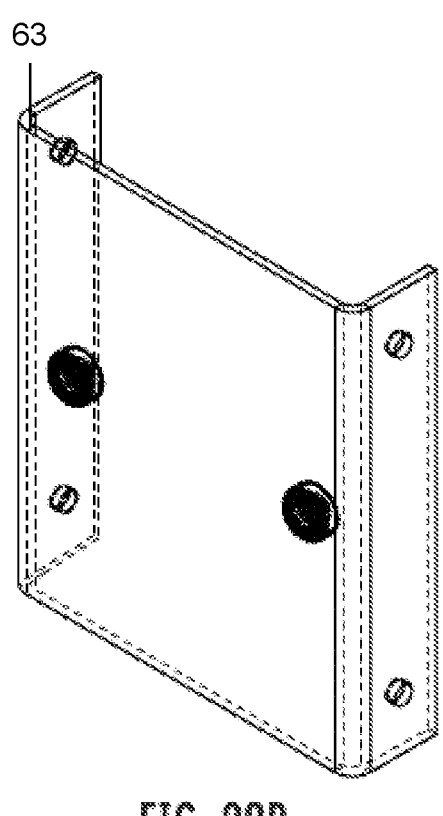
FIG. 22B illustrates an angled perspective view of the front fan bracket 63 of the system 100.
Figure 22A:
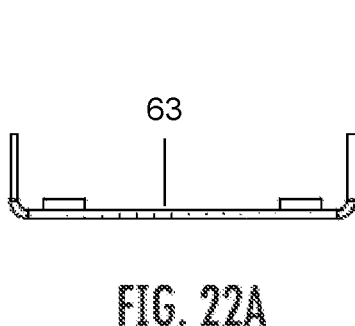
FIG. 22A illustrates a top view of the front fan bracket 63 of the system 100.
Figure 22C:
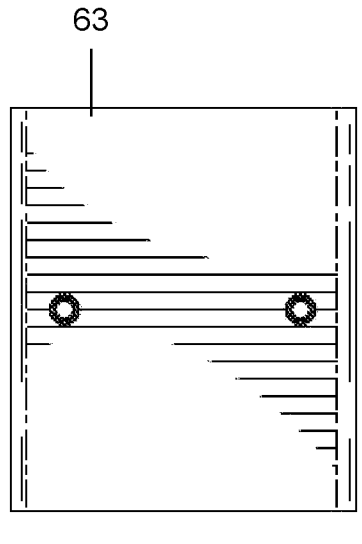
FIG. 22C illustrates a front view of the front fan bracket 63 of the system 100.
Figure 22D:
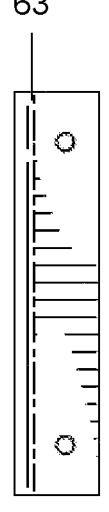
FIG. 22D illustrates a side view of the front fan bracket 63 of the system 100.
Figure 23A:
FIG. 23A illustrates a top view of the front fan bracket 63 of the system 100.
Figure 23B:
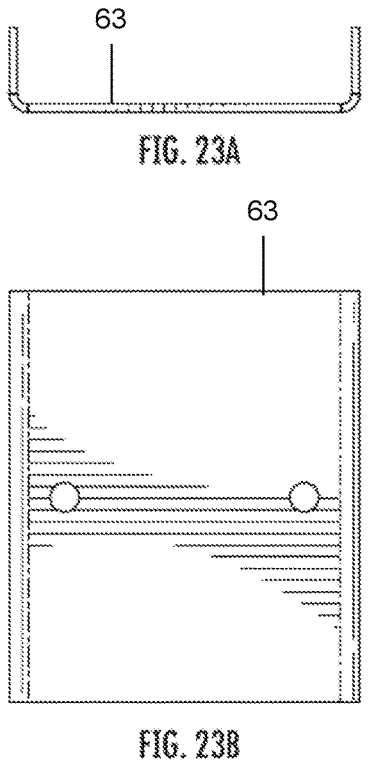
FIG. 23B illustrates a front view of the front fan bracket 63 of the system 100.
Figure 23C:
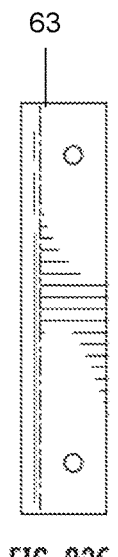
FIG. 23C illustrates a side view of the front fan bracket 63 of the system 100.
Figure 23D:
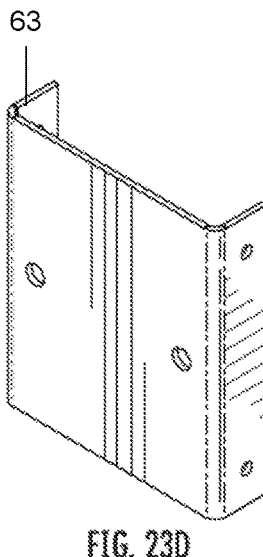
FIG. 23D illustrates an angled perspective view of the front fan bracket 63 of the system 100.
Figures 24A, 24B, 24C, 24D:
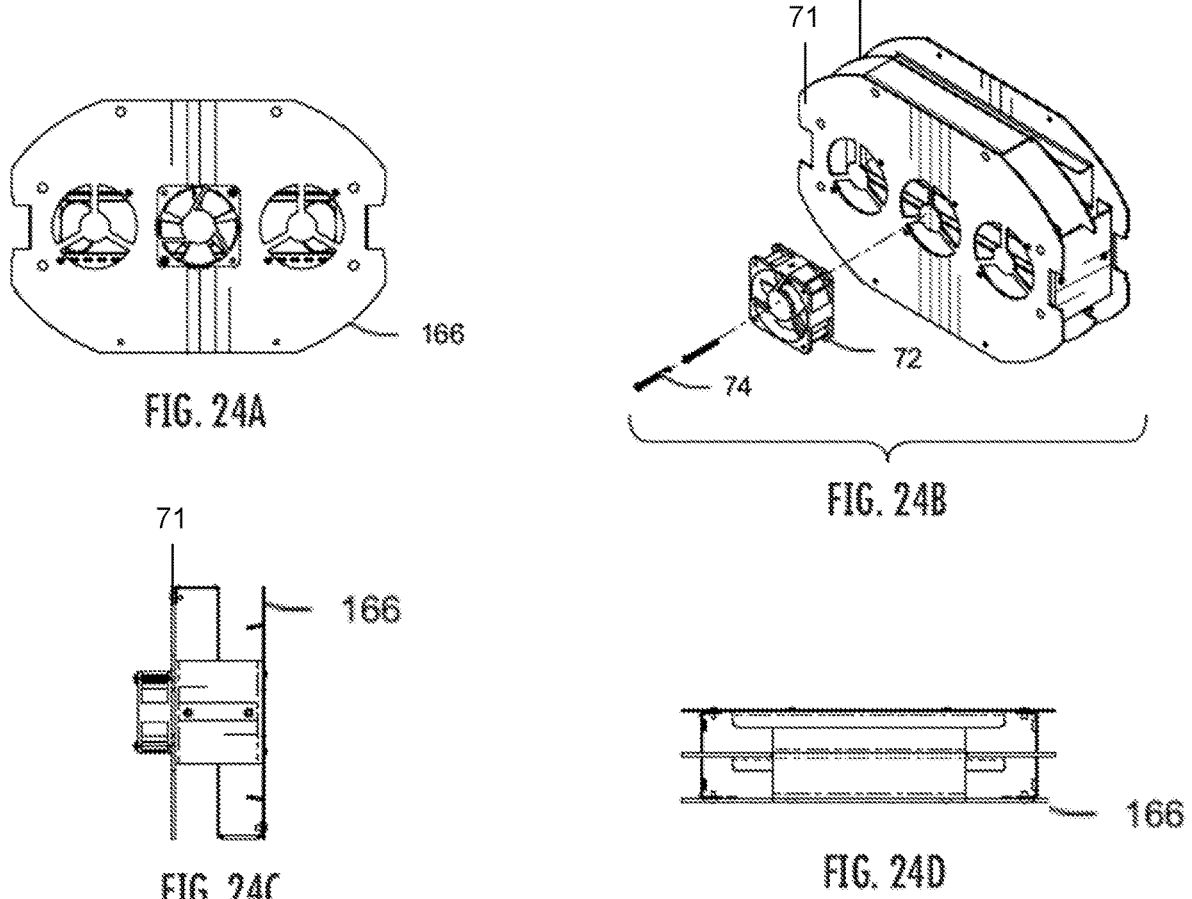
FIG. 24A illustrates a front view of the rear fan assembly 166 of the system 100.
FIG. 24B illustrates an angled perspective view of the rear fan assembly 166 of the system 100.
FIG. 24C illustrates a side view of the rear fan assembly 166 of the system 100.
FIG. 24D illustrates a top view of the rear fan assembly 166 of the system 100.
Figures 25A, 25B, 25C, 25D:
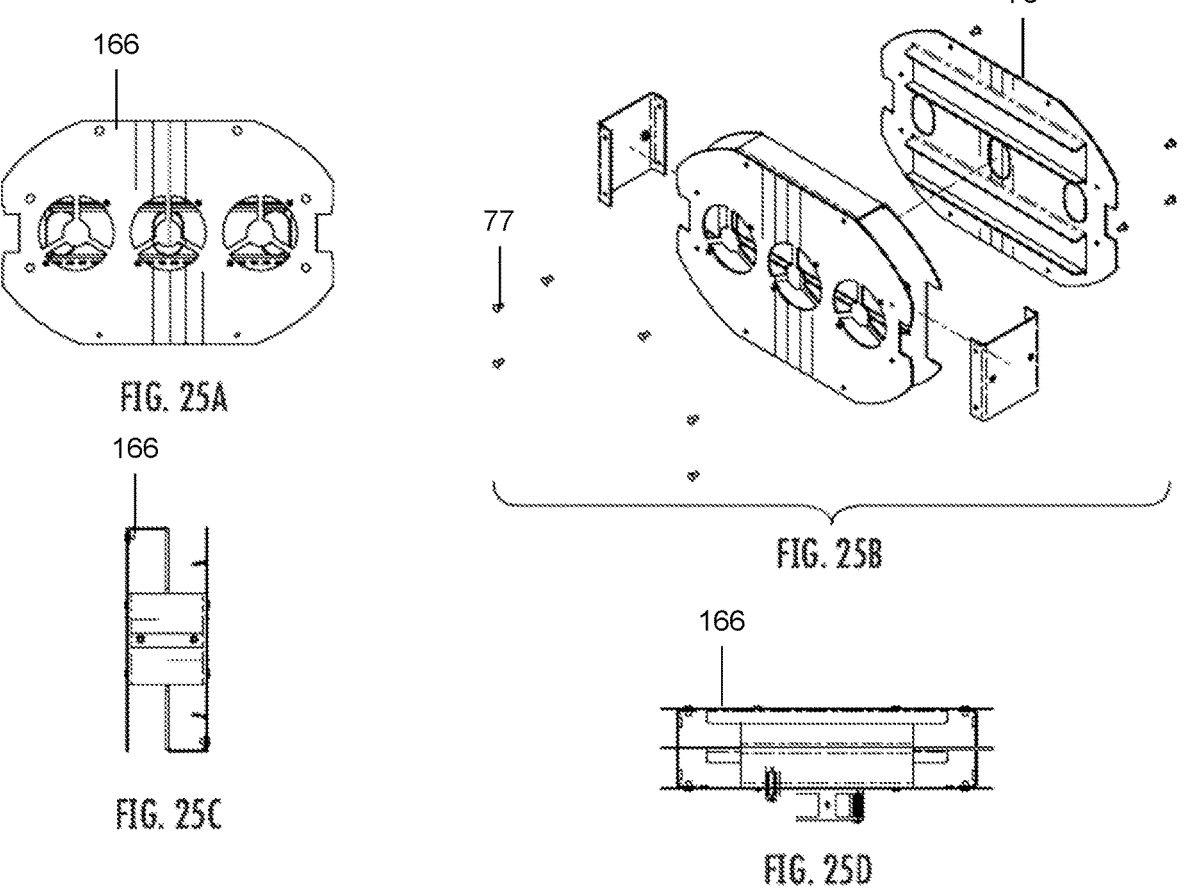
FIG. 25A illustrates a front view of some components of the rear fan assembly 166 of the system 100.
FIG. 25B illustrates an angled perspective view of some components of the rear fan assembly 166 of the system 100.
FIG. 25C illustrates a side view of some components of the rear fan assembly 166 of the system 100.
FIG. 25D illustrates a top view of some components of the rear fan assembly 166 of the system 100.

The fan mid-baffle 65 has a center horizontal cut-out to allow for air flow to pass through. The cut out has angled protrusions, as can be seen in FIG. 20D. The fan internal baffle 66 has two horizontal cut-outs in a different horizontal plane than the cut-out in the fan mid-baffle 65. As shown in FIGS. 20 and 21, the fan mid-baffle 65 has a center horizontal cut-out, and the fan internal baffle 66 has a top cut-out and a bottom cut-out. The cut outs of the fan internal baffle 66 may have angled protrusions as can be seen in FIG. 21D. The offset orientation of the cut-outs of the fan mid-baffle 65 and fan internal baffle 66 allows for air flow to pass through the baffles, but minimizes and attempts to not allow UV light from passing from inside main body 150 to the exterior of system 100 through body assembly first end 130 or body assembly second end 140.

As shown in FIGS. 21A-21E, the center of front fan internal baffle 66 has three oval shaped mounts for mounting UV light bulbs. In the embodiment shown, there are three mounts for mounting UV light bulbs in the center of the front fan internal baffle 66. Notably, however, the number, mounting position, and type of light bulb may be varied and are all within the scope of the present disclosure. The UV light bulbs may be mounted to the fan internal baffle 66, pass through the inner baffle plates 168 and end baffle plates 169, and mount to the rear fan internal baffle 76. In certain embodiments, the UV light bulbs may be UV-C type bulbs used to kill or inactivate microorganisms. In an embodiment, the UV light bulbs may be of the type with 252 nano-meter wavelength. Other wavelength disinfectant lights are known and are within the scope of the present disclosure. UV-C bulbs may be a type of radio frequency emitter or other emitter. Other types of emitters are known and within the scope of the present disclosure. For example, other types of emitters may be used in place of or with the UV-C bulbs. For example, if desired, other types of electromagnetic emitters may be used to emit other wavelengths to achieve a desired objective, for example, extracting out ozone.

As air passes through the front fan internal baffle 66, the air will encounter an end baffle plates 169 and inner baffle plates 168. As shown in FIGS. 8A-8D, the end baffle plates 169 and inner baffle plates 168 may be mounted to baffle brackets 161 at spaced intervals to allow airflow between each of the plates 168 169. In the embodiment shown in FIGS. 8A-8D, there may be two end baffle plates 169 and five inner baffle plates 168, however, other numbers of plates may be utilized as well.

As shown in FIGS. 12A-12D and 13A-13E, end baffle plates 169 may have a pattern of small holes and three pass-through holes. The pattern of small holes allow air to pass through. In an embodiment, the small holes decrease the mass flow rate of the airflow, reduce pressure on the internal side of the end baffle plate that faces the inner baffle plates 168, and randomize particulate flow in the air. The small holes may be the same size or may be different sizes to contribute to the creation of airflow randomization. The three pass-through holes are for the UV bulbs to pass through the end baffle plates 169. In certain embodiments, the pass through holes may be sized and may use a gasket structure to minimize air-flow through the pass-through holes and force air through the small holes.

As shown in FIGS. 9A-9D, the inner baffle plates 168 may include two large holes for airflow and three pass through holes to allow the UV bulbs to pass through the inner baffle plates. In certain embodiments, the pass-through holes may be sized and may use a gasket structure to minimize air-flow through the pass-through holes and force air through the air flow holes. As shown in FIGS. 6A-6D, 7, and 8A-8D, each of the inner baffle plates 168 have airflow holes that do not align with the adjacent inner baffle plate 168. The offset orientation of the airflow holes of the adjacent inner baffle plates 169 creates airflow turbulence for air passing through the system 100.

Air flow between the end baffle assemblies 169 moves slowly and in a turbulent pattern. As air flows through the baffle assembly, the contaminants in the air are exposed to the light emitted by UV-C (or other) light bulbs. The reduced air speed increases the length of time the contaminants are exposed to the UV-C light bulbs. The turbulent air flow pattern may change the radial distance a contaminant may be from the UV-C light bulb as the contaminant travels through the system 100. The increased exposure time and variable contaminant to bulb distance, creates an environment to sanitize the air. In certain embodiments, the internal surfaces of the baffle assembly 160 and main body 150 may be reflective such that the sanitizing intensity of the UV-C light is maintained even as radial distance from the UV-C bulb increases. In certain embodiments, the internal surfaces may be coated with a desired reflective material as well.

After air is sanitized by the UV-C lights, the sanitized air passes through the end baffle plate 169 toward the rear fan assembly 166. The sanitized air may be exhausted through the rear fan internal baffle 76, through the rear fan mid-baffle 75, and through the rear fan mount 71 and one or more rear fans 72 and out of the system 100 at the body assembly second end 140. As shown in FIGS. 24A-24D, the rear fan assembly 166 is of a similar structure to the front fan assembly 165. FIGS. 27A-27E illustrate the rear fan internal baffle 76, having two horizontal air passages on the top and bottom portion, and three light bulb holes on the center portion. In certain embodiments, other numbers of light bulb holes and/or air passages may also be utilized. FIGS. 26A-26D illustrate the rear fan mid-baffle 75 having a single horizontal air passage in the center portion, however, other numbers of air passages may be utilized as well. The air passages of the rear fan mid-baffle 75 and rear fan internal baffle 76 may be offset to allow air to flow through, but minimize or prevent UV-C light from passing through. The air passages may each have flanges as shown in FIGS. 26A-26D and 27A-27E. The sanitized air is exhausted from the system 100 through the rear fan mount 71 and rear fans 72.

In certain embodiments, it is desired that minimal to no UV-C light be transmitted outside the system 100. As shown in FIGS. 1A-1D, 2, and 3A-3E, the main body 150 surrounds the UV-C light bulbs. The UV-C light may be blocked from being transmitted outside the system 100 by the main body 150. At the body assembly first end 130, the front fan mid-baffle 65 and front fan internal baffle 66 may have offset cut-outs for airflow. The cut-outs may be shaped and positioned such that the front fan mid-baffle 65 and front fan internal baffle 66 block UV-C light from being transmitted out the body assembly first end 130. At the body assembly second end 140, the rear fan mid-baffle 75 and rear fan internal baffle 76 have offset cut-outs for airflow. The cut-outs may be shaped and positioned such that the rear fan mid-baffle 75 and rear fan internal baffle 76 block UV-C light from being transmitted out the body assembly second end 140.

In an embodiment, control assembly 120 may be used to control the system 100. The control assembly 120 may use the pushbutton placeholder to control the speed of the fans 62, speed of the fans 72, or both. The control assembly 120 may also be used to control the intensity of the UV lights, for example by turning one or more light bulbs off. In certain embodiments, the intensity of the UV lights may be adjusted to allow for dimming, pulsing, or brightening of each individual light bulb as well. The ballast bracket 184 may be used to hold ballast to stabilize the system 100.

FIGS. 56A-86C illustrate a system 500 in accordance with a second embodiment of the present invention. Notably, the system 500 may incorporate any of the functionality and/or components of the system 100 and/or system 8700. The system 500 may include a top tube portion 506 and a bottom tube portion 504. Within the top tube 506 and bottom tube 504 is an air baffle assembly 505, electronics assembly 507, and end cap assembly 508.

The electronics assembly 507 may include at least one fan that operates to draw air into the system 500. In an embodiment, the electronics assembly 507 may be configured to connect to a network, for example a cellular or wi-fi network. The electronics panel assembly 507 may be configured to monitor the operation of the system 500. The status of system 500 may be communicated via a network connection to a remote system. For example, parameters such as fan speed, maintenance issues, bulb life, or other parameters of system 500 may be communicated to a remote system via a network. In an embodiment, a user may control parameters of system 500 via a network through a remote computer terminal or telephone application. As shown in FIGS. 57A-57F and 70A-70C, air is drawn through intake plate 511 and passes through divider 512. Divider 512 is designed to allow airflow to pass through but block UV-C light. Divider 512 is illustrated in FIGS. 81A-81C, for example. FIG. 57F illustrates a bracket 515 that may be utilized to secure the componentry of the system 500 together. FIGS. 58A-58D illustrate the top tube 506 and lid rib(s) 517 which may be configured to couple to the top tube 506. Lid rib(s) 517 may be utilized to keep one or more mixer plates 513 (or other plates such as intake plate 532 and/or exhaust plate 534) in place within the system 500. The lid ribs 517 may include attachment mechanisms that are configured to secure the lid ribs 517 to the top tube 506, as shown in FIG. 58D In certain embodiments, the lid rib 517 may have a semicircular shape, however, in other embodiments other shapes may also be utilized. The system 500 may also include a lock bracket 518 as illustrated in FIGS. 67A-67E and 58A, 58B, and 58C. The lock bracket 518 may be secured to the top tube 506 and may be utilized to secure components of the system 500 together, as shown in FIGS. 58A-58D. The lock bracket 518 may have a shape as illustrated in FIGS. 67A-67E, however, any suitable shape may be utilized.

FIGS. 59A-59E and 60A-60D illustrate the air baffle assembly 505. The air baffle assembly 505 may include a plurality of mixer plates 513. The mixer plates 513 may have different protrusion patterns designed to mix the air and cause turbulence as air flows along through the system 500. As shown in FIGS. 68A-68D and 69A-69D, the mixer plates 513, 519 may have alternating horizontal and vertical patterns to cause air flow turbulence. For example, in FIGS. 68A-68D the mixer plates 518 may have protrusions that angle outwards and are secured to the mixer plates 513 at horizontal locations on the mixer plates 513. In FIGS. 69A-69D, the mixer plates 519 may have protrusions that angle outwards but are secured to the mixer plates 513 in a vertical fashion on the mixer plates 519. Other orientations may also be utilized for the protrusions and for how the protrusions are secured to the mixer plates 513, 519. The mixer plates 513 may include three oval shaped holes to allow for the UV-C light bulbs to pass through the mixer plates, as shown in FIG. 60A-60D. As air passes through the air baffle assembly 505, the air is exposed to the UV-C light bulbs and the air is sanitized. As shown in FIGS. 56A-56D, the sanitized air is exhausted through the end cap assembly 508. The end cap assembly 508 is designed to allow airflow to pass through but block UV-C light.

The system 500 may include a mount tab 520, as shown in FIG. 57A and FIGS. 71A-71D, which may be utilized to secure components of the system 500 together such as by affixing one or more fasteners to the mount tab 520 and coupling the mount tab 520 to the system 500, as shown in FIG. 57A. The rods 521, as shown in FIGS. 59A-59E and 72A-72C, may be utilized to secure the plates 513, 519 together and may be inserted into holes of the plates 513, 519. and secured to the system 500. The fan motor mount 522 of FIGS. 73A-73D may be utilized to secure one or more fans of the system 500 in place. The rib 523 of the system 500 is illustrated in FIGS. 74A-74C. The mount 524 of the system 500 is shown in FIGS. 75A-75E and 57A and 57B. A bracket mount 525 for use with the system 500 is illustrated in FIGS. 76A-76D. A mount 526 for use with the system 500 is illustrated in FIGS. 77A-77E. A lid rib 527 for use with the system 500 is shown in FIGS. 78A-78C. An embodiment of a divider 528 for use with the system 500 is shown in FIGS. 79A-79C. A fan motor mount 529 for use with the system 500 is shown in FIGS. 80A-80D. Another embodiment of a divider 530 for use with the system 500 is shown in FIGS. 81A-81C. A bulb mount 531 for mounting a bulb for emitting UV light is shown in FIGS. 82A-82E. An intake plate 532 for use with the system 500 is shown in FIGS. 83A-83C. An exhaust plate 533 for use with the system 500 is shown in FIGS. 84A-84C. A lock bracket 534 for use with the system 500 is shown in FIGS. 85A-85E. A rib 535 for use with the system 500 is shown in FIGS. 86A-86C. Notably, the system 500 may also incorporate any of the componentry and functionality of the system 100 as well.

In another embodiment, a method for sanitizing air is disclosed. The method may include a first step, which is taking in air from the atmosphere. The method may include a second step, which is mixing the air by passing the air through baffles. The method may include a third step, which is exposing the mixed air to UV-C light to sanitize the air. The method may include a fourth step, which is exhausting the sanitized air to the atmosphere.

As shown in FIG. 87 and referring also to FIGS. 88-89, a system 8700 and method 8800 for facilitating indoor air purification are disclosed. Notably, the system 8700 may be configured to support, but is not limited to supporting, air purification systems and services, cleaning systems and services, alert systems and services, data analytics systems and services, feedback gathering systems and services, data collation and processing systems and services, artificial intelligence services and systems, machine learning services and systems, content delivery services, cloud computing services, satellite services, telephone services, voice-over-internet protocol services (VoIP), software as a service (SaaS) applications, platform as a service (PaaS) applications, operations management applications and services, productivity applications and services, mobile applications and services, and/or any other computing applications and services. Notably, the system 8700 may include a first user 8701, who may utilize a first user device 8702 to access data, content, and services, or to perform a variety of other tasks and functions. As an example, the first user 8701 may utilize first user device 8702 to transmit signals to access various online services and content, such as those available on an internet, on other devices, and/or on various computing systems. As another example, the first user device 8702 may be utilized to access an application, devices, and/or components of the system 8700 that provide any or all of the operative functions of the system 8700. In certain embodiments, the first user 8701 may be a person, a robot, a humanoid, a program, a computer, any type of user, or a combination thereof, that may be located in a particular environment, which may include the system 100 for facilitating indoor air purification. In certain embodiments, the first user 8701 may be a person that may want to enter a particular environment, such as an office building, movie theater, apartment building, sports venue, any enclosed environment, any partially enclosed environment, any environment, or a combination thereof. Prior to entering the environment and/or while the first user 8701 is in the environment, the system 100 and/or system 8700 may be utilized to purify the air by killing and/or neutralizing viruses, bacteria, microorganisms, pathogens, and/or other potentially harmful bioburden existing in the air of the environment.

The first user device 8702 may include a memory 8703 that includes instructions, and a processor 8704 that executes the instructions from the memory 8703 to perform the various operations that are performed by the first user device 8702. In certain embodiments, the processor 8704 may be hardware, software, or a combination thereof. The first user device 8702 may also include an interface 8705 (e.g. screen, monitor, graphical user interface, etc.) that may enable the first user 8701 to interact with various applications executing on the first user device 8702 and to interact with the system 8700 and/or system 100. In certain embodiments, the first user device 8702 may be and/or may include a computer, any type of sensor, a laptop, a set-top-box, a tablet device, a phablet, a server, a mobile device, a smartphone, a smart watch, and/or any other type of computing device. Illustratively, the first user device 8702 is shown as a smartphone device in FIG. 87. In certain embodiments, the first user device 8702 may be utilized by the first user 8701 to control and/or provide some or all of the operative functionality of the system 100 and/or system 8700. For example, the first user device 8702 may include an application which may be utilized to activate the system 100, deactivate the system 100, activate or deactivate components of the system 100, obtain data measured by sensors of the system, obtain data processed by a processor of the system 100, transmit instructions to the system 100, and/or perform any of the functionality of the system 100 and/or as otherwise described herein.

In addition to using first user device 8702, the first user 8701 may also utilize and/or have access to additional user devices. As with first user device 8702, the first user 8701 may utilize the additional user devices to transmit signals to access various online services and content and/or to interact with and/or control system 100. The additional user devices may include memories that include instructions, and processors that executes the instructions from the memories to perform the various operations that are performed by the additional user devices. In certain embodiments, the processors of the additional user devices may be hardware, software, or a combination thereof. The additional user devices may also include interfaces that may enable the first user 8701 to interact with various applications executing on the additional user devices and to interact with the system 8700. In certain embodiments, the first user device 8702 and/or the additional user devices may include a computer, any type of sensor, a laptop, a set-top-box, a tablet device, a phablet, a server, a mobile device, a smartphone, a smart watch, and/or any other type of computing device, and/or any combination thereof. Sensors may include, but are not limited to, cameras, motion sensors, acoustic/audio sensors, sensors for detecting viruses, bacteria, pathogens, and/or organisms, pressure sensors, temperature sensors, light sensors, heart-rate sensors, humidity sensors, any type of sensors, or a combination thereof.

The first user device 8702 and/or additional user devices may belong to and/or form a communications network. In certain embodiments, the communications network may be a local, mesh, or other network that enables and/or facilitates various aspects of the functionality of the system 100. In certain embodiments, the communications network may be formed between the first user device 102 and additional user devices through the use of any type of wireless or other protocol and/or technology. For example, user devices may communicate with one another in the communications network by utilizing any protocol and/or wireless technology, satellite, fiber, or any combination thereof. Notably, the communications network may be configured to communicatively link with and/or communicate with any other network of the system 8700 and/or outside the system 8700.

In certain embodiments, the first user device 8702 and additional user devices belonging to the communications network may share and exchange data with each other via the communications network. For example, the user devices may share information relating to the system 100, information relating to the system 500, information relating to sanitization and/or sterilization of air in an environment, information relating to the types of pathogens being sterilized by the system 100 and/or system 500, information relating to the various components of the user devices, information associated with images and/or content accessed by a user of the user devices, information identifying the locations of the user devices, information indicating the types of sensors that are contained in and/or on the user devices, information identifying the applications being utilized on the user devices, information identifying how the user devices are being utilized by a user, information identifying user profiles for users of the user devices, information identifying device profiles for the user devices, information identifying the number of devices in the communications network, information identifying devices being added to or removed from the communications network, any other information, or any combination thereof.

In addition to the first user 8701, the system 8700 may also include a second user 8710. Much like the first user 8701, the second user 8710 may be a person that may want to enter into a particular environment of choice and may seek to have the benefit of sterilized and/or purified air in the environment. In certain embodiments, the second user 8710 may be a person that may want to control the system 100 and/or system 500. In certain embodiments, the second user device 8711 may be utilized by the second user 8710 to transmit signals to request various types of content, services, and data provided by and/or accessible by communications network 8735 or any other network in the system 8700. In further embodiments, the second user 8710 may be a robot, a computer, a humanoid, an animal, any type of user, or any combination thereof. The second user device 8711 may include a memory 8712 that includes instructions, and a processor 8713 that executes the instructions from the memory 8712 to perform the various operations that are performed by the second user device 8711. In certain embodiments, the processor 8713 may be hardware, software, or a combination thereof. The second user device 8711 may also include an interface 8714 (e.g. screen, monitor, graphical user interface, etc.) that may enable the second user 8710 to interact with various applications executing on the second user device 8711 and, in certain embodiments, to interact with the system 800. In certain embodiments, the second user device 8711 may be a computer, a laptop, a set-top-box, a tablet device, a phablet, a server, a mobile device, a smartphone, a smart watch, and/or any other type of computing device. Illustratively, the second user device 8711 is shown as a mobile device in FIG. 87. In certain embodiments, the second user device 8711 may also include sensors, such as, but are not limited to, cameras, audio sensors, motion sensors, pressure sensors, temperature sensors, light sensors, humidity sensors, any type of sensors, or a combination thereof.

In certain embodiments, the first user device 8702, the additional user devices, and/or the second user device 8711 may have any number of software applications and/or application services stored and/or accessible thereon. For example, the first user device 8702, the additional user devices, and/or the second user device 8711 may include applications for controlling and/or accessing the operative features and functionality of the system 100, applications for controlling and/or accessing any component of the system 100, applications for monitoring the status of the system 100, applications for obtaining sensor data from sensors of the system 100, media distribution and/or presentation applications, biometric applications, cloud-based applications, other types of phone-based applications, product-ordering applications, business applications, e-commerce applications, media streaming applications, content-based applications, media-editing applications, database applications, gaming applications, internet-based applications, browser applications, mobile applications, service-based applications, productivity applications, video applications, music applications, social media applications, any other type of applications, any types of application services, or a combination thereof. In certain embodiments, the software applications may support the functionality provided by the system 8700 and methods described in the present disclosure. In certain embodiments, the software applications and services may include one or more graphical user interfaces to enable the first and/or potentially second users 8701, 8710 to readily interact with the software applications. The software applications and services may also be utilized by the first and/or second users 8701, 8710 to interact with any device in the system 8700, any network in the system 8700, or any combination thereof. In certain embodiments, the first user device 8702, the additional user devices, and/or the second user device 8711 may include associated telephone numbers, device identities, or any other identifiers to uniquely identify the first user device 8702, the additional user devices, and/or the second user device 8711.

The system 8700 may also include a communications network 8735. The communications network 8735 may be under the control of a service provider, a company that controls the system 100, the first user 8701, the second user 8710 any other designated user, a computer, another network, or a combination thereof. The communications network 8735 of the system 8700 may be configured to link each of the devices in the system 8700 to one another. For example, the communications network 8735 may be utilized by the first user device 8702 to connect with other devices within or outside communications network 8735. Additionally, the communications network 8735 may be configured to transmit, generate, and receive any information and data traversing the system 8700. In certain embodiments, the communications network 8735 may include any number of servers, databases, or other componentry. The communications network 8735 may also include and be connected to a mesh network, a local network, a cloud-computing network, an IMS network, a VoIP network, a security network, a VoLTE network, a wireless network, an Ethernet network, a satellite network, a broadband network, a cellular network, a private network, a cable network, the Internet, an internet protocol network, MPLS network, a content distribution network, any network, or any combination thereof. Illustratively, servers 8740, 8745, and 8750 are shown as being included within communications network 8735. In certain embodiments, the communications network 8735 may be part of a single autonomous system that is located in a particular geographic region, or be part of multiple autonomous systems that span several geographic regions.

Notably, the functionality of the system 8700 may be supported and executed by using any combination of the servers 8740, 8745, 8750, and 8760. The servers 8740, 8745, and 8750 may reside in communications network 8735, however, in certain embodiments, the servers 8740, 8745, 8750 may reside outside communications network 8735. The servers 8740, 8745, and 8750 may provide and serve as a server service that performs the various operations and functions provided by the system 8700. In certain embodiments, the server 8740 may include a memory 8741 that includes instructions, and a processor 8742 that executes the instructions from the memory 8741 to perform various operations that are performed by the server 8740. The processor 8742 may be hardware, software, or a combination thereof. Similarly, the server 8745 may include a memory 8746 that includes instructions, and a processor 8747 that executes the instructions from the memory 8746 to perform the various operations that are performed by the server 8745. Furthermore, the server 8750 may include a memory 8751 that includes instructions, and a processor 8752 that executes the instructions from the memory 8751 to perform the various operations that are performed by the server 8750. In certain embodiments, the servers 8740, 8745, 8750, and 8760 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 8740, 8745, 8750 may be communicatively linked to the communications network 8735, any network, any device in the system 8700, or any combination thereof.

The database 8755 of the system 8700 may be utilized to store and relay information that traverses the systems 100, 500, 8700, cache content that traverses the system 100, 500, 8700, store data about each of the components in the system 100, 8700, 500 and perform any other typical functions of a database. In certain embodiments, the database 8755 may be connected to or reside within the communications network 8735, any other network, or a combination thereof. In certain embodiments, the database 8755 may serve as a central repository for any information associated with any of the devices and information associated with the system 8700. Furthermore, the database 8755 may include a processor and memory or may be connected to a processor and memory to perform the various operation associated with the database 8755. In certain embodiments, the database 855 may be connected to the servers 8740, 8745, 8750, 8760, the first user device 8702, the second user device 8711, the additional user devices, any devices in the system 8700, any process of the system 8700, any program of the system 8700, any other device, any network, or any combination thereof.

The database 8755 may also store information and metadata obtained from the system 8700, store metadata and other information associated with the first and second users 8701, 8710, store sensor data and/or content obtained from an environment that the first and/or second users 8701, 8710 are located in, store data associated with the condition and/or statuses of the systems 100, 500, store data indicating the types of pathogens, viruses, bacteria, and/or microorganisms encountered by the system 100, 500, store data relating to the purification status of air traversing the systems 100, 500, store user profiles associated with the first and second users 8701, 8710, store device profiles associated with any device in the system 8700, store communications traversing the system 8700, store user preferences, store information associated with any device or signal in the system 8700, store information relating to patterns of usage relating to the user devices 8702, 8711, store any information obtained from any of the networks in the system 8700, store historical data associated with the first and second users 8701, 8710, store device characteristics, store information relating to any devices associated with the first and second users 8701, 8710, store information associated with the communications network 8735, store any information generated and/or processed by the system 8700, store any of the information disclosed for any of the operations and functions disclosed for the system 8700 herewith, store any information traversing the system 8700, or any combination thereof. Furthermore, the database 8755 may be configured to process queries sent to it by any device in the system 8700.

Notably, as shown in FIG. 87, the system 8700 may perform any of the operative functions disclosed herein by utilizing the processing capabilities of server 8760, the storage capacity of the database 8755, or any other component of the system 800 to perform the operative functions disclosed herein. The server 8760 may include one or more processors 8762 that may be configured to process any of the various functions of the system 8700. The processors 8762 may be software, hardware, or a combination of hardware and software. Additionally, the server 8760 may also include a memory 8761, which stores instructions that the processors 8762 may execute to perform various operations of the system 8700. For example, the server 8760 may assist in processing loads handled by the various devices in the systems 8700, 100, 500 such as, but not limited to, activating and/or deactivating the systems 100, 500; gathering data from sensors of the systems 100, 500; determining statuses associated with the operation of the systems 100, 500; determining the types of pathogens, viruses, bacteria, and/or microorganisms present in the air; activating and/or deactivating the UV light emission capabilities of a lens of the system 100, 500; activating and/or deactivating the fans of the system 100, 500, and performing any other suitable operations conducted in the system 8700, 100, 500 or otherwise. In one embodiment, multiple servers 8760 may be utilized to process the functions of the system 8700, 100, 500. The server 8760 and other devices in the system 8700, may utilize the database 8755 for storing data about the devices in the system 8700 or any other information that is associated with the system 8700. In one embodiment, multiple databases 8755 may be utilized to store data in the system 8700.

Although FIG. 87 illustrates specific example configurations of the various components of the system 8700, the system 8700 may include any configuration of the components, which may include using a greater or lesser number of the components. For example, the system 8700 is illustratively shown as including a first user device 8702, a second user device 8711, a communications network 8735, a server 8740, a server 8745, a server 8750, a server 8760, and a database 8755. However, the system 8700 may include multiple first user devices 8702, multiple second user devices 8711, multiple communications networks 8735, multiple servers 8740, multiple servers 8745, multiple servers 8750, multiple servers 8760, multiple databases 8755, and/or any number of any of the other components inside or outside the system 8700. Furthermore, in certain embodiments, substantial portions of the functionality and operations of the system 8700 may be performed by other networks and systems that may be connected to system 8700.

As shown in FIG. 88, an exemplary method 8800 for facilitating indoor air purification is schematically illustrated. The method 8800 and/or functionality and features supporting the method 8800 may be conducted via an application of the system 8800, 100, 500, devices of the system 8800, 100, 500 processes of the system 8800, 100, 500 any component of the system 8800, 100, 500 or a combination thereof. The method 8800 may include steps for facilitating indoor air purification, such as by utilizing the functional capabilities of systems 100, 500. The steps of method 8800 may be performed in any desired sequence, however, in a preferred embodiment, the method 8800 may proceed as follows: At step 8802, the method 8800 may include activating a system for facilitating purification of air in an environment. For example, at step 8802, the system 100 may be activated. The system 100 may be activated by a switch of the system 100, by a control signal received from a remote device (e.g. first user device 8702), by a control signal received from a local device, by other means, or a combination thereof. In certain embodiments, the activating of the system 100 may be performed and/or facilitated by utilizing the first user 8701, the second user 8710 and/or by utilizing the first user device 8702, the second user device 8711, the server 8740, the server 8745, the server 8750, the server 8760, the communications network 8735, any component of the systems 8700, 100, 50 any combination thereof, and/or by utilizing any other appropriate program, network, system, or device.

At step 8804, the method 8800 may include drawing in air from the environment into the system 100. For example, air may be drawn into the system 100 via one or more fans of a front fan assembly of the system 100. In certain embodiments, the drawing in of the air from the environment may be performed and/or facilitated by utilizing the first user 8701, the second user 8710 and/or by utilizing the first user device 8702, the second user device 8711, the server 8740, the server 8745, the server 8750, the server 8760, the communications network 8735, any component of the systems 8700, 100, 500, any combination thereof, and/or by utilizing any other appropriate program, network, system, or device. At step 8806, the method 8800 may include facilitating passage of the air to a baffle assembly of the system 100 while ensuring that UV light emitted by an emitter of the system 100 (or 500) is blocked from escaping the system 100. In certain embodiments, the facilitating of the passage of the air to the baffle assembly may be performed by utilizing the first user device 8702, the second user device 8711, the server 8740, the server 8745, the server 8750, the server 8760, the communications network 8735, any component of the systems 8700, 100, 500, any combination thereof, and/or by utilizing any other appropriate program, network, system, or device.

At step 8808, the method 8800 may include causing mixing, turbulence, and/or a slowing down of the air as the air passes through the baffle assembly of the system 100. For example, protrusions, holes, structures, and/or other components of the baffle assembly may be utilized to facilitate mixing of the air, turbulence of the air and/or slowing down of the air so that the UV light emitted by the emitter (e.g. a bulb) may have more time and more efficacy in terms of sanitizing the air and/or killing pathogens existing in the air. In certain embodiments, the mixing, turbulence, and/or slowing down of the air may be performed and/or facilitated by utilizing the first user device 8702, the second user device 8711, the server 8740, the server 8745, the server 8750, the server 8760, the communications network 8735, any component of the systems 8700, 100, 500, any combination thereof, and/or by utilizing any other appropriate program, network, system, or device. At step 8810, the method 8800 may include exposing the mixed, turbulent, and/or slowed down air to the UV light to sanitize the air. The exposing of the air to the UV light may be performed and/or facilitated by utilizing the first user device 8702, the second user device 8711, the server 8740, the server 8745, the server 8750, the server 8760, the communications network 8735, any component of the systems 8700, 100, 500, any combination thereof, and/or by utilizing any other appropriate program, network, system, or device. At step 8812, the method 8800 may include exhausting the sanitized air out of the system 100 and into the environment. The steps of the method 8800 may be repeated continuously, at periodic intervals, and/or at selected timeframes. The method 8800 may also be utilized to monitor the performance of the system 100 (or 500). For example, the method 8800 may include monitoring the types of pathogens being sanitized by the system 100, the amount of bioburden in the air, whether components of the system 100 are deteriorating or failing, whether new components of the system 100 need to be ordered, times at which bioburden is high versus times at which bioburden is low, whether uses are in the environment that the system 100 is located in, whether the air is being sanitized effectively, sensor data obtained from sensors of the system 100, or a combination thereof. In certain embodiments, the method 8800 may include adjusting the operation of the system 100 based on the monitored conditions. For example, if it is known the users are in the environment, the method 8800 may include activating the system 100 and/or increasing the rate at which air is sanitized by the system 100. As another example, if it is known the users are not in the environment, the method 8800 may include deactivating the system 100 or reducing the rate at which air is sanitized by the system 100. If sensor data indicates humidity, temperature, pressure, and/or other conditions are outside a threshold range, the method 8800 may include transmitting alerts to systems or individuals indicating that operation of the system 100 may be compromised and they certain actions need to be taken. Notably, the method 8800 may further incorporate any of the features and functionality described for the systems 100, 500, 8700, any other method disclosed herein, and/or any other features and/or functionality described herein.

The systems and methods disclosed herein may include still further functionality and features. For example, the operative functions of the systems 8700, 100, 500 and method may be configured to execute on a special-purpose processor specifically configured to carry out the operations provided by the systems 100, 500, 8700 and method. Notably, the operative features and functionality provided by the system 8700 and method may increase the efficiency of computing devices that are being utilized to facilitate the functionality provided by the system 8700 and the various methods discloses herein. For example, by training the system 8700 over time based on data and/or other information provided and/or generated in the system 8700, a reduced amount of computer operations may need to be performed by the devices in the system 8700 using the processors and memories of the system 8700 than compared to traditional methodologies. In such a context, less processing power needs to be utilized because the processors and memories do not need to be dedicated for processing. As a result, there are substantial savings in the usage of computer resources by utilizing the software, techniques, and algorithms provided in the present disclosure. In certain embodiments, various operative functionality of the system 800 may be configured to execute on one or more graphics processors and/or application specific integrated processors.

Notably, in certain embodiments, various functions and features of the system 8700 and methods may operate without any human intervention and may be conducted entirely by computing devices. In certain embodiments, for example, numerous computing devices may interact with devices of the system 8700 to provide the functionality supported by the system 8700. Additionally, in certain embodiments, the computing devices of the system 8700 may operate continuously and without human intervention to reduce the possibility of errors being introduced into the system 8700. In certain embodiments, the system 8700 and methods may also provide effective computing resource management by utilizing the features and functions described in the present disclosure. For example, in certain embodiments, devices in the system 8700 may transmit signals indicating that only a specific quantity of computer processor resources (e.g. processor clock cycles, processor speed, etc.) may be devoted to activating and/or deactivating the systems 100, 500, utilizing the fans of the systems 100, 500, capture sensor data from sensors of the systems 100, 500, and/or performing any other operation conducted by the system 100, or any combination thereof. For example, the signal may indicate a number of processor cycles of a processor may be utilized to draw in and/or exhaust out air from and/or into an environment, and/or specify a selected amount of processing power that may be dedicated to generating or any of the operations performed by the systems 8700, 100, 500. In certain embodiments, a signal indicating the specific amount of computer processor resources or computer memory resources to be utilized for performing an operation of the system 8700 may be transmitted from the first and/or second user devices 8702, 8711 to the various components of the system 800.

In certain embodiments, any device in the system 8700 may transmit a signal to a memory device to cause the memory device to only dedicate a selected amount of memory resources to the various operations of the system 8700. In certain embodiments, the system 8700 and methods may also include transmitting signals to processors and memories to only perform the operative functions of the system 8700 and methods at time periods when usage of processing resources and/or memory resources in the system 800 is at a selected value. In certain embodiments, the system 8700 and methods may include transmitting signals to the memory devices utilized in the system 8700, which indicate which specific sections of the memory should be utilized to store any of the data utilized or generated by the system 8700. Notably, the signals transmitted to the processors and memories may be utilized to optimize the usage of computing resources while executing the operations conducted by the system 8700. As a result, such functionality provides substantial operational efficiencies and improvements over existing technologies.

Referring now also to FIG. 89, at least a portion of the methodologies and techniques described with respect to the exemplary embodiments of the system 8900 can incorporate a machine, such as, but not limited to, computer system 8900, or other computing device within which a set of instructions, when executed, may cause the machine to perform any one or more of the methodologies or functions discussed above. The machine may be configured to facilitate various operations conducted by the systems 100, 500, 8700. For example, the machine may be configured to, but is not limited to, assist the systems 100, 500, 8700 by providing processing power to assist with processing loads experienced in the systems 100, 500, 8700 by providing storage capacity for storing instructions or data traversing the systems 100, 500, 8700 or by assisting with any other operations conducted by or within the systems 100, 500, 8700. As another example, the computer system 8900 may assist with activating and/or deactivating the systems 100, 500, activating and/or deactivating sensors of the systems 100, 500, drawing in air via the fan assemblies of the systems 100, 500, transmitting data acquired by the systems 100, 500 to other devices, receiving control instructions from devices to control systems 100, 500, and/or performing any of the operations and functionality described in the present disclosure.

In some embodiments, the machine may operate as a standalone device. In some embodiments, the machine may be connected (e.g., using communications network 8735, another network, or a combination thereof) to and assist with operations performed by other machines and systems, such as, but not limited to, the first user device 8702, the second user device 8711, the server 8740, the server 8745, the server 8750, the database 8755, the server 8760, any other system, program, and/or device, or any combination thereof. The machine may be connected with any component in the system 8700 and/or systems 100, 500. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 8900 may include a processor 8902 (e.g., a central processing unit (CPU), a graphics processing unit (GPU, or both), a main memory 8904 and a static memory 8906, which communicate with each other via a bus 8908. The computer system 8900 may further include a video display unit 8910, which may be, but is not limited to, a liquid crystal display (LCD), a flat panel, a solid-state display, or a cathode ray tube (CRT). The computer system 8900 may include an input device 8912, such as, but not limited to, a keyboard, a cursor control device 8914, such as, but not limited to, a mouse, a disk drive unit 8916, a signal generation device 8918, such as, but not limited to, a speaker or remote control, and a network interface device 8920.

The disk drive unit 8916 may include a machine-readable medium 8922 on which is stored one or more sets of instructions 8924, such as, but not limited to, software embodying any one or more of the methodologies or functions described herein, including those methods illustrated above. The instructions 8924 may also reside, completely or at least partially, within the main memory 8904, the static memory 8906, or within the processor 8902, or a combination thereof, during execution thereof by the computer system 8900. The main memory 8904 and the processor 8902 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 8922 containing instructions 8924 so that a device connected to the communications network 8735, another network, or a combination thereof, can send or receive voice, video or data, and communicate over the communications network 8735, another network, or a combination thereof, using the instructions. The instructions 8924 may further be transmitted or received over the communications network 8735, another network, or a combination thereof, via the network interface device 8920.

While the machine-readable medium 8922 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

The invention claimed is:

1. A system for sanitizing air, comprising:
a main body;
a baffle assembly,
wherein the baffle assembly includes a fan assembly, an inner baffle plate, an end baffle plate, and an emitter;
wherein said fan assembly includes fans, a front fan mount plate, a mid-baffle and internal baffle to block electromagnetic waves emitted by the emitter from escaping into an environment within which the system is located,
wherein the inner baffle plate includes at least a first hole to allow air to flow through the inner baffle plate and at least a second hole,
wherein the emitter passes through the second hole of the inner baffle plate and is mounted to the internal baffle,
wherein the fans are mounted to the front fan mount plate; and
wherein the inner baffle plate, and mid-baffle include angled protrusions to alter air flow.

2. The system of claim 1, further comprising a divider, an end cap assembly, or a combination thereof, to facilitate blocking of the electromagnetic waves from escaping into the environment.

3. The system of claim 1, wherein the baffle assembly is configured to mix air drawn into the system to increase an efficacy of sterilization of the air by the electromagnetic waves.

4. The system of claim 1, further comprising a rear fan assembly configured to exhaust the air after the air has been sanitized by the system.

5. The system of claim 1, further comprising a control assembly for controlling operating of the emitter, the fan assembly, or a combination thereof.

6. The system of claim 1, further comprising an electronics panel assembly configured to monitor operation of the system.

7. The system of claim 6, wherein the electronics panel assembly is further configured to facilitate communication of the system with a remote system, device, or a combination thereof.

8. A system for sanitizing air, comprising:
a main body;
a baffle assembly,
wherein said baffle assembly includes a fan assembly, a plurality of mixer plates, and an emitter;
wherein the fan assembly includes fans and a front fan mount plate,
wherein the fans are mounted to the front fan mount plate, wherein the plurality of mixer plates include protrusions to alter air flow and at least one hole, wherein the emitter passes through the plurality of mixer plates through the at least one hole.

9. The system of claim 8, further comprising a rear fan assembly configured to exhaust air from the system into an environment.

10. The system of claim 8, wherein a subset of the mixer plates include different protrusions from another subset of the mixer plates to facilitate mixing of the air.

11. The system of claim 8, wherein the emitter is configured to emit electromagnetic waves to facilitate sanitization of the air within the main body of the system.

12. The system of claim 8, further comprising an end assembly through which the air enters the system.

13. The system of claim 8, wherein the mixer plates include a plurality of protrusions to facilitate mixing of the air, generation of turbulence of the air, slowing down the air, or a combination thereof.

14. The system of claim 8, further comprising a top tube and a bottom tube for housing components of the system.

15. A method of sanitizing air, comprising:

taking in air from an atmosphere by utilizing a fan assembly of a system;

mixing the air by passing the air through a baffle assembly of the system;

exposing the mixed air to ultraviolet light emitted by an emitter of the system to sanitize the air;

obtaining sensor data from at least one sensor of the system;

detecting viruses, bacteria, pathogens, and/or organisms utilizing the sensor data;

determining a purification status utilizing the sensor data;

adjusting a rate of sanitization of the mixed air based on the sensor data;

exhausting the sanitized air to the atmosphere;

wherein the baffle assembly includes an inner baffle plate, said inner baffle plate includes at least a first hole to allow air to flow through the inner baffle plate and at least a second hole to allow the emitter to pass through the inner baffle plate; and wherein the inner baffle plate includes angled protrusions to alter air flow.

16. The method of claim 15, further comprising facilitating turbulence of the air by utilizing the baffle assembly of the system.

17. The method of claim 15, further comprising reducing a velocity or speed of the air by utilizing the baffle assembly of the system.

18. The method of claim 15, further comprising utilizing a divider, an end cap assembly, or a combination thereof, to block the ultraviolet light from escaping the system.

19. The method of claim 15, further comprising redrawing in the air from the atmosphere into the system to further sanitize the air.

20. The method of claim 15, further comprising facilitating activation of the system, deactivation of the system, control of the system, or a combination thereof, by utilizing a device communicatively linked to the system.

* * * * *